United States Patent [19]

Hammonds et al.

[11] Patent Number: 5,057,417
[45] Date of Patent: Oct. 15, 1991

[54] COMPOSITIONS AND METHODS FOR THE SYNTHESIS OF GROWTH HORMONE RECEPTOR AND GROWTH HORMONE BINDING PROTEIN

[75] Inventors: R. Glenn Hammonds, San Francisco; David W. Leung, Foster City; Steven A. Spencer; William I. Wood, both of San Mateo, all of Calif.

[73] Assignee: Genentech, Inc., South San Francisco, Calif.

[21] Appl. No.: 62,542

[22] Filed: Jun. 12, 1987

[51] Int. Cl.⁵ .................. C12P 21/00; C12N 15/00; C12N 5/00; C07H 21/00
[52] U.S. Cl. .................. 435/69.1; 435/172.3; 435/240.2; 435/252.33; 435/317.1; 536/27; 935/70; 935/73; 935/11
[58] Field of Search ............... 536/27; 435/320, 240.2, 435/68, 172.3, 317.1, 252.33, 69.1; 935/70, 73, 11

[56] References Cited

U.S. PATENT DOCUMENTS

| | | | |
|---|---|---|---|
| 4,753,874 | 6/1988 | Carlos et al. | 435/6 |
| 4,761,371 | 8/1988 | Bell et al. | 435/68 |
| 4,775,630 | 10/1988 | Tibbetts et al. | 435/320 |
| 4,797,368 | 1/1989 | Carter et al. | 435/320 |

OTHER PUBLICATIONS

Nikaido et al., Nature 311: 631-635 (1984).
Barnard et al., Biochemistry J. 237: 885-892 (1986).
Ullrich et al., Nature 309: 418-425 (1984).
Hatakeyama et al., Nature 318: 467-470 (1985).

*Primary Examiner*—Elizabeth C. Weimar
*Assistant Examiner*—Jasemine C. Chambers
*Attorney, Agent, or Firm*—Robert H. Benson; Max D. Hensley

[57] ABSTRACT

Growth hormone receptor and growth hormone binding protein are purified enabling amino acid sequence and DNA isolates coding for growth hormone receptor and growth hormone binding protein and methods of obtaining such DNA are provided, together with expression systems for recombinant production of growth hormone receptor and growth hormone binding protein. Therapeutically useful forms of the growth hormone receptor and growth hormone binding protein and anti-receptor antibodies are described.

21 Claims, 65 Drawing Sheets

Purified Rabbit Growth Hormone Receptor (MgCl$_2$ Eluate)

Purified Rabbit Growth Hormone Receptor (Urea Eluate)

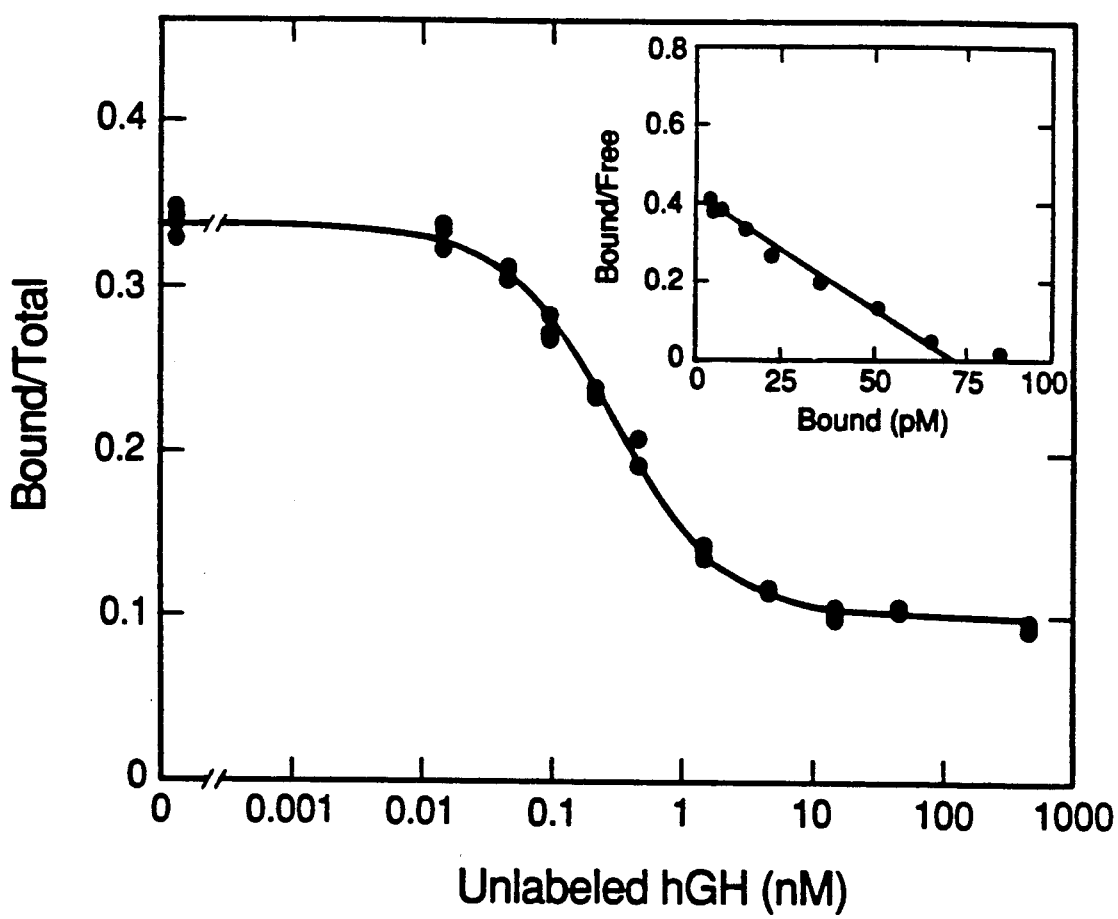
FIG. 3c Purified Rabbit Serum Binding Protein (MgCl$_2$ Eluate)

Purified Rabbit Growth Hormone Receptor
($MgCl_2$ Eluate)

Purified Rabbit Growth Hormone Receptor
(Urea Eluate)

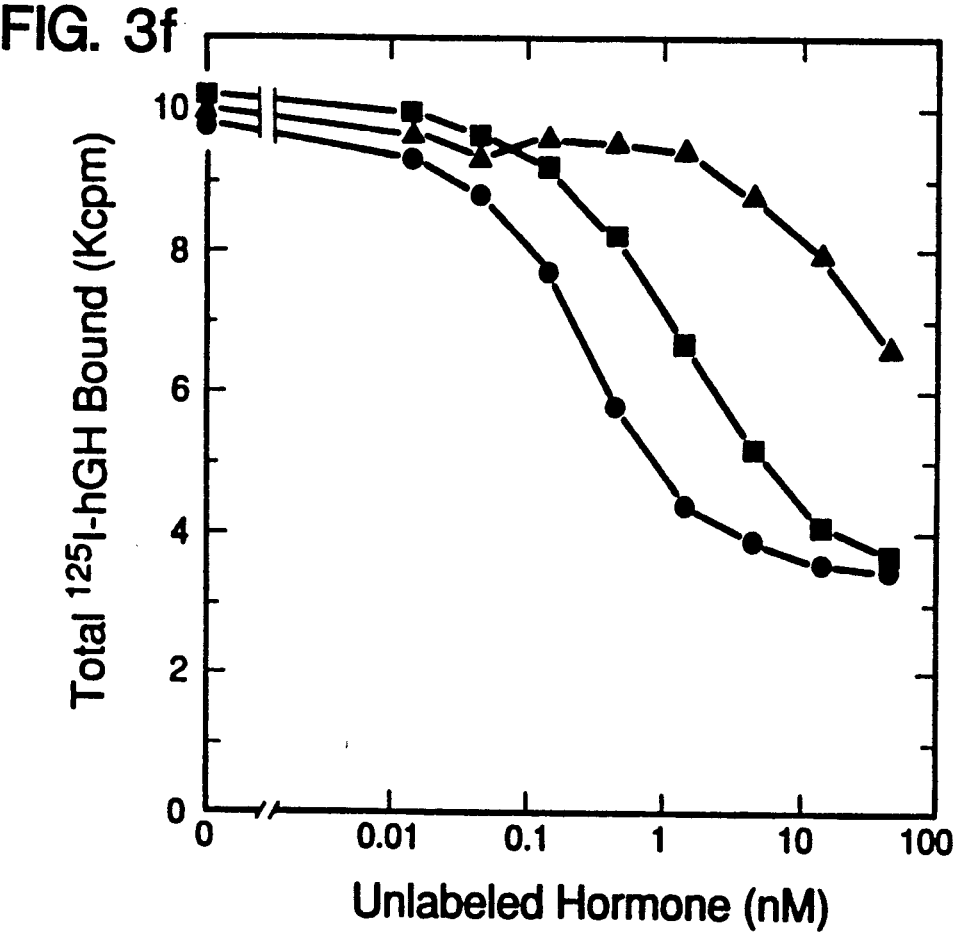
FIG. 3f
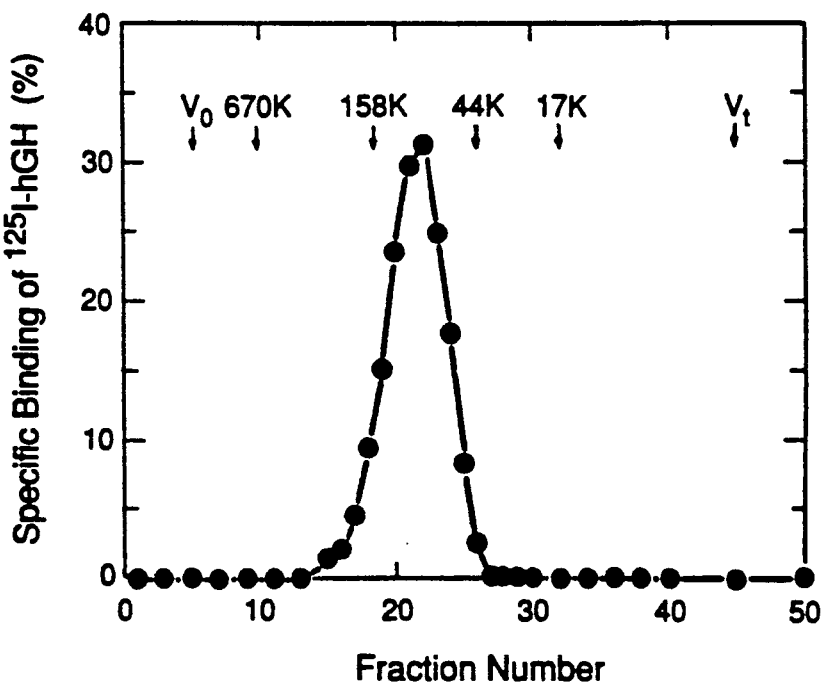
FIG. 4 S-300 Gel Filtration Column of Rabbit Serum Growth Hormone Binding Protein HPLC Separation of Rabbit Growth Hormone Receptor V8 Digest

FIG.8a-1

```
 -43                         CCG CGCTCTCTGA

-30 TCAGAGGCGA AGCTCGGAGG TCCTACAGGT

1 ATGGATCTCT GGCAGCTGCT GTTGACCTTG
 -18 M   D   L   W   Q   L   L   L   T   L

31 GCACTGGCAG GATCAAGTGA TGCTTTTTCT
  -8 A   L   A   G   S   S   D   A   F   S

61 GGAAGTGAGG CCACAGCAGC TATCCTTAGC
   3 G   S   E   A   T   A   A   I   L   S

91 AGAGCACCCT GGAGTCTGCA AAGTGTTAAT
  13 R   A   P   W   S   L   Q   S   V   N

121 CCAGGCCTAA AGACAAATTC TTCTAAGGAG
  23 P   G   L   K   T   N   S   S   K   E

151 CCTAAATTCA CCAAGTGCCG TTCACCTGAG
  33 P   K   F   T   K   C   R   S   P   E

181 CGAGAGACTT TTTCATGCCA CTGGACAGAT
  43 R   E   T   F   S   C   H   W   T   D

211 GAGGTTCATC ATGGTACAAA GAACCTAGGA
  53 E   V   H   H   G   T   K   N   L   G

241 CCCATACAGC TGTTCTATAC CAGAAGGAAC
  63 P   I   Q   L   F   Y   T   R   R   N
```

FIG.8a-2

```
271 ACTCAAGAAT GGACTCAAGA ATGGAAAGAA
 73  T  Q  E  W   T  Q  E    W  K  E

301 TGCCCTGATT ATGTTTCTGC TGGGGAAAAC
 83  C  P  D  Y   V  S  A    G  E  N

331 AGCTGTTACT TTAATTCATC GTTTACCTCC
 93  S  C  Y  F   N  S  S    F  T  S

361 ATCTGGATAC CTTATTGTAT CAAGCTAACT
103  I  W  I  P   Y  C  I    K  L  T

391 AGCAATGGTG GTACAGTGGA TGAAAAGTGT
113  S  N  G  G   T  V  D    E  K  C

421 TTCTCTGTTG ATGAAATAGT GCAACCAGAT
123  F  S  V  D   E  I  V    Q  P  D

451 CCACCCATTG CCCTCAACTG GACTTTACTG
133  P  P  I  A   L  N  W    T  L  L ecoRV
481 AACGTCAGTT TAACTGGGAT TCATGCAGAT
143  N  V  S  L   T  G  I    H  A  D

511 ATCCAAGTGA GATGGGAAGC ACCACGCAAT
153  I  Q  V  R   W  E  A    P  R  N

541 GCAGATATTC AGAAAGGATG GATGGTTCTG
163  A  D  I  Q   K  G  W    M  V  L
```

FIG.8a-3

```
571 GAGTATGAAC TTCAATACAA AGAAGTAAAT
173  E  Y  E  L    Q  Y  K     E  V  N

601 GAAACTAAAT GGAAAATGAT GGACCCTATA
183  E  T  K  W    K  M  M     D  P  I

631 TTGACAACAT CAGTTCCAGT GTACTCATTG
193  L  T  T  S    V  P  V     Y  S  L

661 AAAGTGGATA AGGAATATGA AGTGCGTGTG
203  K  V  D  K    E  Y  E     V  R  V

691 AGATCCAAAC AACGAAACTC TGGAAATTAT
213  R  S  K  Q    R  N  S     G  N  Y

721 GGCGAGTTCA GTGAGGTGCT CTATGTAACA
223  G  E  F  S    E  V  L     Y  V  T

751 CTTCCTCAGA TGAGCCAATT TACATGTGAA
233  L  P  Q  M    S  Q  F     T  C  E ncoI
781 GAAGATTTCT ACTTTCCATG GCTCTTAATT
243  E  D  F  Y    F  P  W     L  L  I

811 ATTATCTTTG GAATATTTGG GCTAACAGTG
253  I  I  F  G    I  F  G     L  T  V

841 ATGCTATTTG TATTCTTATT TTCTAAACAG
263  M  L  F  V    F  L  F     S  K  Q
```

FIG.8a-4

```
 871 CAAAGGATTA AAATGCTGAT TCTGCCCCCA
 273 Q   R  I  K   M  L  I   L  P  P claI
 901 GTTCCAGTTC CAAAGATTAA AGGAATCGAT
 283 V  P  V  P   K  I  K   G  I  D

931 CCAGATCTCC TCAAGGAAGG AAAATTAGAG
 293 P  D  L  L   K  E  G   K  L  E

961 GAGGTGAACA CAATCTTAGC CATTCATGAT
 303 E  V  N  T   I  L  A   I  H  D ecoRI
 991 AGCTATAAAC CCGAATTCCA CAGTGATGAC
 313 S  Y  K   P  E  F  H   S  D  D

1021 TCTTGGGTTG AATTTATTGA GCTAGATATT
 323 S  W  V  E   F  I  E   L  D  I

1051 GATGAGCCAG ATGAAAAGAC TGAGGAATCA
 333 D  E  P  D   E  K  T   E  E  S

1081 GACACAGACA GACTTCTAAG CAGTGACCAT
 343 D  T  D  R   L  L  S   S  D  H

1111 GAGAAATCAC ATAGTAACCT AGGGGTGAAG
 353 E  K  S  H   S  N  L   G  V  K
```

FIG.8a-5

```
1141 GATGGCGACT CTGGACGTAC CAGCTGTTGT
 363 D   G   D   S   G   R   T   S   C   C

1171 GAACCTGACA TTCTGGAGAC TGATTTCAAT
 373 E   P   D   I   L   E   T   D   F   N

1201 GCCAATGACA TACATGAGGG TACCTCAGAG
 383 A   N   D   I   H   E   G   T   S   E

1231 GTTGCTCAGC CACAGAGGTT AAAAGGGGAA
 393 V   A   Q   P   Q   R   L   K   G   E

1261 GCAGATCTCT TATGCCTTGA CCAGAAGAAT
 403 A   D   L   L   C   L   D   Q   K   N

1291 CAAAATAACT CACCTTATCA TGATGCTTGC
 413 Q   N   N   S   P   Y   H   D   A   C

1321 CCTGCTACTC AGCAGCCCAG TGTTATCCAA
 423 P   A   T   Q   Q   P   S   V   I   Q

1351 GCAGAGAAAA ACAAACCACA ACCACTTCCT
 433 A   E   K   N   K   P   Q   P   L   P

1381 ACTGAAGGAG CTGAGTCAAC TCACCAAGCT
 443 T   E   G   A   E   S   T   H   Q   A

1411 GCCCATATTC AGCTAAGCAA TCCAAGTTCA
 453 A   H   I   Q   L   S   N   P   S   S
```

FIG.8a-6

```
1441 CTGTCAAACA TCGACTTTTA TGCCCAGGTG
 463  L  S  N  I   D  F  Y   A  Q  V

1471 AGCGACATTA CACCAGCAGG TAGTGTGGTC
 473  S  D  I  T   P  A  G   S  V  V smaI
1501 CTTTCCCCGG GCCAAAAGAA TAAGGCAGGG
 483  L  S  P  G   Q  K  N   K  A  G

1531 ATGTCCCAAT GTGACATGCA CCCGGAAATG
 493  M  S  Q  C   D  M  H   P  E  M

1561 GTCTCACTCT GCCAAGAAAA CTTCCTTATG
 503  V  S  L  C   Q  E  N   F  L  M

1591 GACAATGCCT ACTTCTGTGA GGCAGATGCC
 513  D  N  A  Y   F  C  E   A  D  A

1621 AAAAAGTGCA TCCCTGTGGC TCCTCACATC
 523  K  K  C  I   P  V  A   P  H  I hindIII
1651 AAGGTTGAAT CACACATACA GCCAAGCTTA
 533  K  V  E  S   H  I  Q   P  S  L

1681 AACCAAGAGG ACATTTACAT CACCACAGAA
 543  N  Q  E  D   I  Y  I   T  T  E
```

FIG.8a-7

```
1711 AGCCTTACCA CTGCTGCTGG GAGGCCTGGG
 553 S   L   T   T   A   A   G   R   P   G

1741 ACAGGAGAAC ATGTTCCAGG TTCTGAGATG
 563 T   G   E   H   V   P   G   S   E   M

1771 CCTGTCCCAG ACTATACCTC CATTCATATA
 573 P   V   P   D   Y   T   S   I   H   I

1801 GTACAGTCCC CACAGGGCCT CATACTCAAT
 583 V   Q   S   P   Q   G   L   I   L   N

1831 GCGACTGCCT TGCCCTTGCC TGACAAAGAG
 593 A   T   A   L   P   L   P   D   K   E

1861 TTTCTCTCAT CATGTGGCTA TGTGAGCACA
 603 F   L   S   S   C   G   Y   V   S   T

1891 GACCAACTGA ACAAAATCAT GCCTTAGCCT
 613 D   Q   L   N   K   I   M   P   O

1921 TTCTTTGGTT TCCCAAGAGC TACGTATTTA

1951 ATAGCAAAGA ATTGACTGGG GCAATAACGT

1981 TTAAGCCAAA ACAATGTTTA AACCTTTTTT

2011 GGGGGAGTGA CAGGATGGGG TATGGATTCT

2041 AAAATGCCTT TTCCCAAAAT GTTGAAATAT
```

FIG.8a-8

```
2071 GATGTTAAAA AAATAAGAAG AATGCTTAAT
2101 CAGATAGATA TTCCTATTGT GCAATGTAAA
2131 TATTTTAAAG AATTGTGTCA GACTGTTTAG
2161 TAGCAGTGAT TGTCTTAATA TTGTGGGTGT
2191 TAATTTTTGA TACTAAGCAT TGAATGGCTA
2221 TGTTTTTAAT GTATAGTAAA TCACGCTTTT
2251 TGAAAAGCG AAAAAATCAG GTGGCTTTTG
2281 CGGTTCAGGA AAATTGAATG CAAACCATAG
2311 CACAGGCTAA TTTTTTGTTG TTTCTTAAAT
2341 AAGAAACTTT TTTATTTAAA AAACTAAAAA
2371 CTAGAGGTGA GAAATTTAAA CTATAAGCAA
2401 GAAGGCAAAA ATAGTTTGGA TATGTAAAAC
2431 ATTTACTTTG ACATAAAGTT GATAAAGATT
2461 TTTTAATAAT TTAGACTTCA AGCATGGCTA
                                   pstI
2491 TTTTATATTA CACTACACAC TGTGTACTGC
```

FIG.8a-9

```
2521 AGTTGGTATG ACCCCTCTAA GGAGTGTAGC
2551 AACTACAGTC TAAAGCTGGT TTAATGTTTT
2581 GGCCAATGCA CCTAAAGAAA AACAAACTCG
2611 TTTTTTACAA AGCCCTTTTA TACCTCCCCA
2641 GACTCCTTCA ACAATTCTAA AATGATTGTA
2671 GTAATCTGCA TTATTGGAAT ATAATTGTTT
2701 TATCTGAATT TTTAAACAAG TATTTGTTAA
2731 TTTAGAAAAC TTTAAAGCGT TTGCACAGAT
2761 CAACTTACCA GGCACCAAAA GAAGTAAAAG
2791 CAAAAAAGAA AACCTTTCTT CACCAAATCT
2821 TGGTTGATGC CAAAAAAAAA TACATGCTAA
2851 GAGAAGTAGA AATCATAGCT GGTTCACACT
2881 GACCAAGATA CTTAAGTGCT GCAATTGCAC
2911 GCGGAGTGAG TTTTTTAGTG CGTGCAGATG
                                    pstI
2941 GTGAGAGATA AGATCTATAG CCTCTGCAGC
```

FIG.8a-10

```
2971 GGAATCTGTT CACACCCAAC TTGGTTTTGC
3001 TACATAATTA TCCAGGAAGG GAATAAGGTA
3031 CAAGAAGCAT TTTGTAAGTT GAAGCAAATC
3061 GAATGAAATT AACTGGGTAA TGAAACAAAG
3091 AGTTCAAGAA ATAAGTTTTT GTTTCACAGC
3121 CTATAACCAG ACACATACTC ATTTTTCATG
3151 ATAATGAACA GAACATAGAC AGAAGAAACA
3181 AGGTTTTCAG TCCCCACAGA TAACTGAAAA
3211 TTATTTAAAC CGCTAAAAGA AACTTTCTTT
3241 CTCACTAAAT CTTTTATAGG ATTTATTTAA
3271 AATAGCAAAA GAAGAAGTTT CATCATTTTT
3301 TACTTCCTCT CTGAGTGGAC TGGCCTCAAA
3331 GCAAGCATTC AGAAGAAAAA GAAGCAACCT
3361 CAGTAATTTA GAAATCATTT TGCAATCCCT
3391 TAATATCCTA AACATCATTC ATTTTTGTTG
```

FIG.8a-11

```
3421  TTGTTGTTGT  TGTTGAGACA  GAGTCTCGCT

3451  CTGTCGCCAG  GCTAGAGTGC  GGTGGCGCGA

3481  TCTTGACTCA  CTGCAATCTC  CACCTCCCAC

3511  AGGTTCAGGC  GATTCCGTG   CCTCAGCCTC

3541  CTGAGTAGCT  GGGACTACAG  GCACGCACCA

3571  CCATGCCAGG  CTAATTTTTT  TGTATTTTAG

3601  CAGAGACGGG  GTTTCACCAT  GTTGGCCAGG xhoI
3631  ATGGTCTCGA  GTCTCCTGAC  CTCGTGATCC

3661  ACCCGACTCG  GCCTCCCAAA  GTGCTGGGAT

3691  TACAGGTGTA  AGCCACCGTG  CCCAGCCCTA ecoRV
3721  AACATCATTC  TTGAGAGCAT  TGGGATATCT

3751  CCTGAAAAGG  TTTATGAAAA  AGAAGAATCT

3781  CATCTCAGTG  AAGAATACTT  CTCATTTTTT hindIII
3811  AAAAAAGCTT  AAAACTTTGA  AGTTAGCTTT
```

FIG.8a-12

3841 AACTTAAATA GTATTTCCCA TTTATCGCAG hindIII

3871 ACCTTTTTTA GGAAGCAAGC TTAATGGCTG

3901 ATAATTTTAA ATTCTCTCTC TTGCAGGAAG

3931 GACTATGAAA AGCTAGAATT GAGTGTTTAA

3961 AGTTCAACAT GTTATTTGTA ATAGATGTTT

3991 GATAGATTTT CTGCTACTTT GCTGCTATGG

4021 TTTTCTCCAA GAGCTACATA ATTTAGTTTC

4051 ATATAAAGTA TCATCAGTGT AGAACCTAAT

4081 TCAATTCAAA GCTGTGTGTT TGGAAGACTA

4111 TCTTACTATT TCACAACAGC CTGACAACAT

4141 TTCTATAGCC AAAAATAGCT AAATACCTCA

4171 ATCAGTCTCA GAATGTCATT TTGGTACTTT

4201 GGTGGCCACA TAAGCCATTA TTCACTAGTA

4231 TGACTAGTTG TGTCTGGCAG TTTATATTTA

4261 ACTCTCTTTA TGTCTGTGGA TTTTTTCCTT

FIG.8a-13

```
4291 CAAAGTTTAA TAAATTTATT TTCTTGGATT

4321 CCTGATAATG TGCTTCTGTT ATCAAACACC

4351 AACATAAAAA TGATCTAAAC CAAAAAAAAA

4381 AAAAAAAAAA AAA
```

FIG.8b-1

```
-144              TTAG TATAATGTTA TCTGGTTGCA

-120 TATATGGCTA AGTGAAAAGA AAATTGAAGA

-90 GTTTCTTGAT ACAAAGCCTG GAGGGAGCTA

-60 CACGTTCAAA AATCCAACTT CTATATCAGG

-30 AACATCTGCT GGACTATTGG TCCTACAGGT

1 ATGGATCTCT GGCAGCTGCT GTTGACCGTG
 -18 M  D  L  W    Q  L  L    L  T  V

31 GCACTAGCAG GGTCAAGTGA TGCTTTTTCT
  -8 A  L  A    G  S  S  D    A  F  S

61 GGGAGTGAGG CCACACCAGC TACCCTTGGC
   3 G  S  E    A  T  P  A    T  L  G

91 AGAGCATCCG AGAGTGTGCA AAGAGTTCAT
  13 R  A  S  E    S  V  Q    R  V  H

121 CCAGGCCTGG GGACAAATTC TTCTGGGAAG
  23 P  G  L  G    T  N  S    S  G  K

151 CCCAAATTCA CCAAGTGCCG TTCACCTGAA
  33 P  K  F  T    K  C  R    S  P  E

181 CTAGAGACTT TTTCATGCCA CTGGACAGAT
  43 L  E  T  F    S  C  H    W  T  D
```

FIG.8b-2

```
211 GGGGTTCATC ATGGTTTAAA GAGCCCAGGA
 53 G  V  H  H   G  L  K    S  P  G

241 TCTGTGCAGC TGTTCTATAT TAGGAGGAAC
 63 S  V  Q  L   F  Y  I    R  R  N

271 ACTCAAGAAT GGACTCAAGA ATGGAAAGAA
 73 T  Q  E  W   T  Q  E    W  K  E

301 TGCCCTGACT ATGTTTCTGC TGGGGAGAAC
 83 C  P  D  Y   V  S  A    G  E  N

331 AGCTGTTACT TTAATTCATC CTATACCTCC
 93 S  C  Y  F   N  S  S    Y  T  S

361 ATTTGGATCC CCTACTGTAT CAAGCTAACT
103 I  W  I  P   Y  C  I    K  L  T

391 AACAATGGTG GTATGGTGGA TCAAAAGTGT
113 N  N  G  G   M  V  D    Q  K  C

421 TTCTCTGTTG AGGAAATAGT GCAACCAGAT
123 F  S  V  E   E  I  V    Q  P  D

451 CCACCCATTG GCCTCAACTG GACTTTACTG
133 P  P  I  G   L  N  W    T  L  L

481 AATGTTAGCT TAACCGGGAT TCATGCAGAT
143 N  V  S  L   T  G  I    H  A  D
```

FIG.8b-3

```
511 ATTCAAGTGC GATGGGAACC ACCACCCAAT
153 I  Q  V  R   W  E  P   P  P  N

541 GCAGATGTTC AGAAGGGATG GATAGTCTTG
163 A  D  V  Q   K  G  W   I  V  L

571 GAGTATGAAC TTCAATACAA AGAAGTCAAT
173 E  Y  E  L   Q  Y  K   E  V  N

601 GAAACTCAAT GGAAAATGAT GGACCCTGTA
183 E  T  Q  W   K  M  M   D  P  V

631 TTGTCGACAT CAGTTCCTGT GTACTCGTTA
193 L  S  T  S   V  P  V   Y  S  L

661 AGACTGGACA AAGAATATGA AGTGCGTGTG
203 R  L  D  K   E  Y  E   V  R  V

691 AGATCCAGAC AGCGAAGCTC TGAAAAATAT
213 R  S  R  Q   R  S  S   E  K  Y

721 GGCGAGTTCA GTGAGGTGCT CTATGTAACC
223 G  E  F  S   E  V  L   Y  V  T

751 CTTCCTCAAA TGAGCCCATT CACATGTGAA
233 L  P  Q  M   S  P  F   T  C  E ncoI
781 GAAGATTTCC GGTTTCCATG GTTCTTAATT
243 E  D  F  R   F  P  W   F  L  I
```

FIG.8b-4

```
 811 ATTATCTTTG GAATATTTGG ACTAACAGTG
 253  I   I  F  G    I  F  G   L  T  V

841 ATGCTATTCG TATTCATATT TTCTAAACAG
 263  M  L  F  V   F  I  F    S  K  Q

871 CAAAGGATTA AGATGCTGAT TCTGCCCCCA
 273  Q  R  I  K   M  L  I    L  P  P claI
 901 GTTCCAGTTC CAAAGATTAA AGGAATCGAT
 283  V  P  V  P   K  I  K    G  I  D

931 CCAGATCTCC TCAAGGAAGG AAAGTTAGAG
 293  P  D  L  L   K  E  G    K  L  E

961 GAGGTGAACA CAATCTTAGC CATTCAAGAT
 303  E  V  N  T   I  L  A    I  Q  D ecoRI
 991 AGCTATAAGC CTGAATTCTA CAATGATGAC
 313  S  Y  K  P   E  F  Y    N  D  D ecoRI                     claI
1021 TCTTGGGTTG AATTCATCGA GCTAGACATC
 323  S  W  V  E   F  I  E    L  D  I

1051 GATGACCCTG ATGAAAAGAC TGAGGGATCA
 333  D  D  P  D   E  K  T    E  G  S
```

FIG.8b-5

```
1081 GACACAGACC GACTTCTAAG CAACAGCCAT
 343 D  T  D  R   L  L  S    N  S  H

1111 CAGAAATCAC TTAGCGTCCT TGCAGCAAAG
 353 Q  K  S  L   S  V  L    A  A  K

1141 GATGACGACT CTGGACGAAC CAGCTGTTAC
 363 D  D  D  S   G  R  T    S  C  Y

1171 GAACCTGACA TCCTGGAGAA TGATTTCAAT
 373 E  P  D  I   L  E  N    D  F  N

1201 GCCAGTGACG GGTGCGACGG GAACTCGGAG
 383 A  S  D  G   C  D  G    N  S  E

1231 GTTGCTCAGC CTCAAAGGTT AAAAGGGGAA
 393 V  A  Q  P   Q  R  L    K  G  E

1261 GCAGATCTCT TGTGCCTTGA CCAGAAGAAT
 403 A  D  L  L   C  L  D    Q  K  N

1291 CAAAATAACT CACCTTACCA TGATGTTTCT
 413 Q  N  N  S   P  Y  H    D  V  S

1321 CCTGCTGCTC AGCAGCCTGA GGTCGTCCTA
 423 P  A  A  Q   Q  P  E    V  V  L

1351 GCAGAGGAAG ACAAACCGCG ACCACTTCTT
 433 A  E  E  D   K  P  R    P  L  L
```

FIG.8b-6

```
1381 ACTGGTGAGA TTGAATCCAC TCTTCAGGCT
 443 T  G  E  I   E  S  T    L  Q  A

1411 GCACCTTCTC AGCTCAGCAA TCCAAATTCA
 453 A  P  S  Q   L  S  N    P  N  S

1441 CTGGCAAACA TCGACTTTTA CGCCCAGGTT
 463 L  A  N  I   D  F  Y    A  Q  V

1471 AGTGACATTA CGCCGGCAGG GAGTGTGGTC
 473 S  D  I  T   P  A  G    S  V  V ecoRI
1501 CTTTCCCCAG GCCAGAAGAA CAAGGCAGGG
 483 L  S  P  G   Q  K  N    K  A  G

1531 AATTCTCAGT GTGATGCGCA TCCAGAAGTC
 493 N  S  Q  C   D  A  H    P  E  V

1561 GTCTCACTCT GCCAGACAAA CTTCATCATG
 503 V  S  L  C   Q  T  N    F  I  M

1591 GACAACGCCT ACTTCTGTGA AGCAGATGCC
 513 D  N  A  Y   F  C  E    A  D  A

1621 AAAAAGTGTA TCGCTGTGGC CCCTCATGTC
 523 K  K  C  I   A  V  A    P  H  V
```

FIG.8b-7

```
                                          hindIII
1651 GACGTCGAAT CACGTGTCGA GCCAAGCTTT
 533 D   V   E   S   R   V   E   P   S   F

1681 AACCAGGAGG ACATTTACAT CACCACAGAA
 543 N   Q   E   D   I   Y   I   T   T   E

1711 AGCCTTACCA CTACTGCCGA GAGGTCTGGG
 553 S   L   T   T   T   A   E   R   S   G

1741 ACAGCAGAAG ACGCCCCAGG TTCTGAGATG
 563 T   A   E   D   A   P   G   S   E   M

1771 CCTGTCCCAG ACTATACCTC CATTCATTTA
 573 P   V   P   D   Y   T   S   I   H   L

1801 GTACAATCTC CACAAGGCCT TGTACTCAAT
 583 V   Q   S   P   Q   G   L   V   L   N

1831 GCAGCCACCT TGCCCTTGCC TGACAAAGAG
 593 A   A   T   L   P   L   P   D   K   E

1861 TTTCTCTCAT CGTGTGGCTA CGTGAGCACA
 603 F   L   S   S   C   G   Y   V   S   T

1891 GACCAACTGA ACAAAATCTT GCCATAGCCT
 613 D   Q   L   N   K   I   L   P   O

1921 TTCTTTGATG TCCAAGAGCT TTGTATCTAA
```

FIG.8b-8

```
1951 TGGCAAAGAA TTGGCTGTGG CATGAATGCT

1981 TAAACCAAAC CAGTGTAAGG GGAATGGAAG

2011 AGTAGGTTGT GGATTCTAAA TGCCTTCTCT

2041 GAAATTTGAA ACAGGATATT AAAAAGAAAA

2071 AACTAAGAGG AATGCTTAAT CAGATAGATA

2101 TTCCTGTTGT GAACTGTAAA TATTTTAAAG

2131 AATTGTCTCA ATACTGTTT  AGTGGCAGTA

2161 ATTGTCTTCT TGTGGGTGTT AATTTTGTGA

2191 TACTAAACAT TGAATGGCTA TGTTTTTAAT

2221 GTATAGTAGA ATCATGCTTT TTGAAAAAGC
                                   pstI
2251 GAAAAATCAG GTGGCTTCTG CAGTTCAGGA

2281 GAACTGAATG AAAATCATAG CACAGACTAA

2311 TTTTTTTCTT CTTAATTAAT TGGGAGCTAA

2341 CACTATAGGT AAGAAGGCAA AAATAGTTTG
```

FIG.8b-9

```
      ecoRV
2371  GATATCTAAA ACACTTATTT TGACATAAAC

2401  TTGATAAAGA TATTTTTAAG AAGTTAAATT

2431  TCAAGCATGG CTATTTTATA TCACCCTATA

2461  CACTGTGTAC TGTAGTTCAA GAAGATTCAT

2491  CTACAGAATG TAGCAACTAC AGTCTCAAGC

2521  TGGTTTGATG CTTTTCATCA GTGCACCTAA

2551  AGAAAACACA CACAAGTGTT TTTTTACAAG

2581  GTCCTTTTTG TACCTTCCAA AACTCATTGA

2611  TTCTAAAATG ATTGTAAAAA TTTGCATATC

2641  GGAACATACT TATTTTATCT GAATTTCTAA

2671  TCAAATATTT GTTAAATTTA GAAAATTTTT

2701  AAATATTTGC ACAAATAAAC TTACATAAAT

2731  CAAAAACCAA ACAACACAAA ACTTTTCTTT

2761  ACCAAATCTT GGTTCGTGCC AGACAGCTGC

2791  ATGCGAAGAG AAGTAGAAAT CATTGCTGGT
```

FIG.8b-10

```
2821 TCACGTTGAC CACAAGACTT AAGTTCTACA
2851 GTGGCATGTG GACTGATTTA GTGCATGCAG
                                        pstI
2881 ACCATGAGAG GTAAGCTCTA TAACCTCTGC
2911 AGTAAAATCT CTTCAAATAT AACTCGATTT
2941 TATTTCATAT TTACCGAAGA GAGGAAGTTG
2971 AAGCAGGTCA AATGAAGCTA ACTGGGTAAA
3001 GGAACAGAAA TAGGTTTTGT TTCACAGCCT
3031 TTACCCAGAC ACATACATAG TCAGTATTCA
3061 TGGCAACAAG AAATAAAAGA AACAAGGTTT
3091 TCAATCCCCA CAGATAACTC AGAGTTACTT
3121 AAACTAGGAG CAGAAACTTT CTCACCAAAA
3151 TTTTTATAAG ATTTAGTTAA ACAGTAAAAG
3181 AAGATGTTTC ATCATTTTTA TTTCCCTCCA
3211 AGTAGTCCAG CCTCAAAGCA GGTAGTCAGA
3241 AAAAAAGAAA GGGGACTTGA GTAATTTGTA
```

FIG.8b-11

```
3271 GATTTTCCAA TTCCTTAATA ACCTAAGTAT

3301 CATTTTTAGA AGCATAGGGA TAGTTCCCAA

3331 AAGGATTATG AAAATGAGAA TACTTAACCA

3361 TTTTAAGAAT TTTTTATATT CTTTTTAAAG

3391 TTAGCATTCA CTTAAATAGT ATTTGCCATT hindIII
3421 TAGCTCAGAC CCCTTTAGAA AGCAAGCTTT

3451 ATGATTGGTA AGTTTTAATT CCTTCTCTCA

3481 TTCAAGAAAG ATGGTGGAAA GCTAGACCTG

3511 GGTGTTTAAA GTTACCGTG ATACTTTGTA

3541 GTAGATGTTT AATAGATTTT CTGCTACCTT

3571 GCTGCTATGG TCTTCTCCAA GAGCTACATA

3601 ATTTAGTTTC ATATACAATA TCATCACAGT

3631 AGAACCTAAT TCAACTTAAA ACTATGTGTT

3661 TGGAAGAACT ATCTTACCAT TTCACAATAG

3691 GCTAACAACA TTTCTATAGC CAAAAATAGC
```

FIG.8b-12

```
3721 TAAATACCTC AATCAGTCTC AGAATGTCAT

3751 TTTGGTACTT TGCTGGCCAC ACAAGCCATT pstI
3781 ATTCACTAGT ATGACTAGTT GTGTCCTGCA

3811 GTTTATATTT AACTTTCTTT ATGTCTGTGG

3841 ATTTTTTTCC TTCAAAGTTT AATAAATTTA

3871 TTTTCTTGAA AAAAA
```

FIG.8c-1

```
-144              TTAGTATAA TGTTATCTGGTTGCA

-120  TATATGGCTAAGTGA AAAGAAAATTGAAGA

-90   GTTTCTTGATACAAA GCCTGGAGGGAGCTA

-43                               CCGCGCTCTCTGA
-60   CACGTTCAAAAATCC AA TT TA  A    A G

-30   TCAGAGGCGAAGCTC GGAGGTCCTACAGGT
-30   AACATCTGCTG ACT ATT

1   ATGGATCTCTGGCAG CTGCTGTTGACCTTG
  1                                 G
-18   M    D  L  W  Q    L  L  L  T  L
-18                                  V

31   GCACTGGCAGGATCA AGTGATGCTTTTTCT
 31        A      G
 -8   A    L  A  G  S    S  D  A  F  S
 -8   ‾

61   GGAAGTGAGGCCACA GCAGCTATCCTTAGC
 61      G            C     C      G
  3   G  S  E  A  T    A  A  I  L  S
  3                    P     T     G
```

FIG.8c-2

```
 91 AGAGCACCCTGGAGT  CTGCAAAGTGTTAAT
 91       T  GA      G     A     C
 13 R  A  P  W  S    L  Q  S  V  N
 13          S  E       V     R  H
    _____

121 CCAGGCCTAAAGACA  AATTCTTCTAAGGA
121        GGG                GG A
 23 P  G  L  K  T    N  S  S  K  E
 23       G                   G  K

151 CCTAAATTCACCAAG  TGCCGTTCACCTGAG
151    C                              A
 33 P  K  F  T  K    C  R  S  P  E
 33

181 CGAGAGACTTTTTCA  TGCCACTGGACAGAT
181    T
 43 R  E  T  F  S    C  H  W  T  D
 43 L

211 GAGGTTCATCATGGT  ACAAAGAACCTAGGA
211    G              TT    G  C
 53 E  V  H  H  G    T  K  N  L  G
 53 G                   L     S  P
                                _____

241 CCCATACAGCTGTTC  TATACCAGAAGGAAC
241 T  TG G                TT    G
 63 P  I  Q  L  F    Y  T  R  R  N
 63 S  V                  I
    _____| T6.1 |_____
```

FIG.8c-3

```
271 ACTCAAGAATGGACT   CAAGAATGGAAAGAA
271
 73  T  Q  E  W  T    Q  E  W  K  E
 73
                           •─────•

301 TGCCCTGATTATGTT   TCTGCTGGGGAAAAC
301         C                    G
 83  C  P  D  Y  V    S  A  G  E  N
 83
     •──── V3 ────    •─────────────

331 AGCTGTTACTTTAAT   TCATCGTTTACCTCC
331                     C A
 93  S  C  Y  F  N    S  S  F  T  S
 93                            Y
     •  •────

361 ATCTGGATACCTTAT   TGTATCAAGCTAACT
361     T  C  C          C
103  I  W  I  P  Y    C  I  K  L  T
103

391 AGCAATGGTGGTACA   GTGGATGAAAAGTGT
391    A       TG            C
113  S  N  G  G  T    V  D  E  K  C
113  N        M             Q
                                  •

421 TTCTCTGTTGATGAA   ATAGTGCAACCAGAT
421           G
123  F  S  V  D  E    I  V  Q  P  D
123           E
     ──•───── T5 ──────────────────
```

FIG.8c-4

```
451 CCACCCATTGCCCTC  AACTGGACTTTACTG
451            G
133  P   P   I   A   L   N   W   T   L   L
133            G
```

```
                                              EcoRV
481 AACGTCAGTTTAACT  GGGATTCATGCAGAT
481     T   T  C        C
143  N   V   S   L   T   G   I   H   A   D
143
```

```
511 ATCCAAGTGAGATGG  GAAGCACCACGCAAT
511     T       C            C       C
153  I   Q   V   R   W   E   A   P   R   N
153                          P       P
```

```
541 GCAGATATTCAGAAA  GGATGGATGGTTCTG
541        G       G        A   CT
163  A   D   I   Q   K   G   W   M   V   L
163          V                   I
```

```
571 GAGTATGAACTTCAA  TACAAAGAAGTAAAT
571                                C
173  E   Y   E   L   Q   Y   K   E   V   N
173                                    ● 
```

```
601 GAAACTAAATGGAAA  ATGATGGACCCTATA
601     C                              G
183  E   T   K   W   K   M   M   D   P   I
183      Q                                 V
       —[T2.2]—   ● —
```

FIG.8c-5

```
631  TTGACAACATCAGTT  CCAGTGTACTCATTG
631      T G              T       G  A
193  L   T  T  S  V   P   V  Y  S  L
193      S

661  AAAGTGGATAAGGAA  TATGAAGTGCGTGTG
661     G  C     C  A
203  K  V  D  K  E   Y   E  V  R  V
203  R     L       ●       T2.1        ●

691  AGATCCAAACAACGA  AACTCTGGAAATTAT
691        G   G       G     A     A
213  R  S  K  Q  R   N   S  G  N  Y
213        R            S     E  K

721  GGCGAGTTCAGTGAG  GTGCTCTATGTAACA
721                                 C
223  G  E  F  S  E   V   L  Y  V  T
223

751  CTTCCTCAGATGAGC  CAATTTACATGTGAA
751        A            C     C
233  L  P  Q  M  S   Q   F  T  C  E
233                   P

NcoI
781  GAAGATTTCTACTTT  CCATGGCTCTTAATT
781            CGG         T
243  E  D  F  Y   F  P  W  L  L  I
243           R            F
```

FIG.8c-6

```
811  ATTATCTTTGGAATA TTTGGGCTAACAGTG
811                               A
253   I  I  F  G  I   F  G  L  T  V
253

841  ATGCTATTTGTATTC TTATTTTCTAAACAG
841          C            A
263   M  L  F  V  F   L  F  S  K  Q
263                      I

871  CAAAGGATTAAAATG CTGATTCTGCCCCCA
871              G
273   Q  R  I  K  M   L  I  L  P  P
273

ClaI
901  GTTCCAGTTCCAAAG ATTAAAGGAATCGAT
901
283   V  P  V  P  K   I  K  G  I  D
283

931  CCAGATCTCCTCAAG GAAGGAAAATTAGAG
931                            G
293   P  D  L  L  K   E  G  K  L  E
293

961  GAGGTGAACACAATC TTAGCCATTCATGAT
961                                A
303   E  V  N  T  I   L  A  I  H  D
303                                Q
```

FIG.8c-7

```
                 EcoRI
 991 AGCTATAAACCCGAA TTCCACAGTGATGAC
 991              G T        T    A
 313   S   Y   K   P   E   F   H   S   D   D
 313                           Y   N

1021 TCTTGGGTTGAATTT ATTGAGCTAGATATT
1021                C   C           C   C
 323   S   W   V   E   F   I   E   L   D   I
 323                          ─────────|V5.2|──

1051 GATGAGCCAGATGAA AAGACTGAGGAATCA
1051       C   T                    G
 333   D   E   P   D   E   K   T   E   E   S
 333       D                                G
     ─────

1081 GACACAGACAGACTT CTAAGCAGTGACCAT
1081           C                 ACAG
 343   D   T   D   R   L   L   S   D   H
 343                           N   S

1111 GAGAAATCACATA GT AACCTAGGGGTGAAG
1111 C             T    C   GT    T CA  CA
 353   E   K   S   H   S   N   L   G   V   K
 353   Q           L       V           A   A

1141 GATGGCGACTCTGGA CGTACCAGCTGTTGT
1141         A              A       AC
 363   D   G   D   S   G   R   T   S   C   C
 363       D                                Y
                                  ──────●──
```

FIG.8c-8

```
1171 GAACCTGACATTCTG GAGACTGATTTCAAT
1171                C              A
 373 E  P  D  I  L   E  T  D  F  N
 373 ─────┤T6.2├───●──────N─────────

KpnI
1201 GCCAATGACATACAT GAGGGTACCTCAGAG
1201    G        GGGTGC    C  G A  G
 383 A  N  D  I  H   E  G  T  S  E
 383    S                D  N
     ──────●──

1231 GTTGCTCAGCCACAG AGGTTAAAAGGGGAA
1231           T  A
 393 V  A  Q  P  Q   R  L  K  G  E
 393

1261 GCAGATCTCTTATGC CTTGACCAGAAGAAT
1261           G
 403 A  D  L  L  C   L  D  Q  K  N
 403

1291 CAAAATAACTCACCT TATCATGATGCTTGC
1291                    C      T  CT
 413 Q  N  N  S  P   Y  H  D  A  C
 413                             V  S

1321 CCTGCTACTCAGCAG CCCAGTGTTATCCAA
1321       G              TGAG CG   T
 423 P  A  T  Q  Q   P  S  V  I  Q
 423       A              E     V  L
```

FIG.8c-9

```
1351 GCAGAGAAAAACAAA    CCACAACCACTTCCT
1351        G   G           G G         T
 433 A  E  K  N  K     P  Q  P  L  P
 433       E  D           R        L

1381 ACTGAAGGAGCTGAG    TCAACTCACCAAGCT
1381     GT AGAT    A      C    TT  G
 443 T  E  G  A  E     S  T  H  Q  A
 443    G  E  I                 L
                                 ─────────

1411 GCCCATATTCAGCTA    AGCAATCCAAGTTCA
1411    A C TC      C                 A
 453 A  H  I  Q  L     S  N  P  S  S
 453    P  S                          N
 ──────────────────── |V5.1| ─────────────

1441 CTGTCAAACATCGAC    TTTTATGCCCAGGTG
1441     G                     C       T
 463 L  S  N  I  D     F  Y  A  Q  V
 463    A
 ───────────────────

1471 AGCGACATTACACCA    GCAGGTAGTGTGGTC
1471    T       G G          G
 473 S  D  I  T  P     A  G  S  V  V
 473

SmaI
1501 CTTTCCCCGGGCCAA    AAGAATAAGGCAGGG
1501         A   G                C
 483 L  S  P  G  Q     K  N  K  A  G
 483
```

FIG.8c-10

```
1531 ATGTCCCAATGTGAC  ATGCACCCGGAAATG
1531  AT  T  G     T  GC    T  A    G C
 493 M  S  Q  C  D     M  H  P  E  M
 493 N                 A           V

1561 GTCTCACTCTGCCAA  GAAAACTTCCTTATG
1561              G   AC      A  C
 503 V  S  L  C  Q     E  N  F  L  M
 503                   T           I

1591 GACAATGCCTACTTC  TGTGAGGCAGATGCC
1591       C                A
 513 D  N  A  Y  F     C  E  A  D  A
 513

1621 AAAAAGTGCATCCCT  GTGGCTCCTCACATC
1621          T   G      C      TG
 523 K  K  C  I  P     V  A  P  H  I
 523             A                 V

HindIII
1651 AAGGTTGAATCACAC  ATACAGCCAAGCTTA
1651  G C  C      GT  G CG           T
 533 K  V  E  S  H     I  Q  P  S  L
 533 D           R     V  E        F 1681 AACCAAGAGGACATT  TACATCACCACAGAA
1681       G
 543 N  Q  E  D  I     Y  I  T  T  E
 543
```

```
1711 AGCCTTACCACTGCT GCTGGGAGGCCTGGG
1711                A        C A    T
 553 S   L   T   T   A    A  G  R  P  G
 553                 T        E     S
     ─────────────────●──── ───────────────

1741 ACAGGAGAACATGTT CCAGGTTCTGAGATG
1741      C       G C CC
 563 T   G   E   H   V    P  G  S  E  M
 563     A       D   A
                          ──[T3]──────────

1771 CCTGTCCCAGACTAT ACCTCCATTCATATA
1771                                T
 573 P   V   P   D   Y    T  S  I  H  I
 573                                   L
     ─────────────────────

1801 GTACAGTCCCCACAG GGCCTCATACTCAAT
1801      A  T      A        TG
 583 V   Q   S   P   Q    G  L  I  L  N
 583                                V

1831 GCGACTGCCTTGCCC TTGCCTGACAAAGAG
1831     AG CA
 593 A   T   A   L   P    L  P  D  K  E
 593     A   T

1861 TTTCTCTCATCATGT GGCTATGTGAGCACA
1861                G           C
 603 F   L   S   S   C    G  Y  V  S  T
 603
```

FIG.8c-12

```
1891 GACCAACTGAACAAA    ATCATGCCTTAGCCT
1891              T     A
 613 D  Q  L  N  K      I  M  P  O
 613                          L

1921 TTCTTTGGTTTCCCA    AGAGCTACGTATTTA
1921        A G -              TT    C

1951 ATAGCAAAGAATTGA    CTGGGGCAATAACGT
1950    G         G        T    TG T C

1981 TTAAGCCAAAACAAT    GTTTAAACCTTTTTT
1980      A    C G     --------------A

2011 GGGGGAGTGACAGGA    TGGGGTATGGATTCT
1998 A    A  GA AG      A   T G

2041 AAAATGCCTTTTCCC    AAAATGTTGAAATAT
2028 -          C TG        --T     C G

2071 GATGTT------AAA    AAAATAAGAAGAATG
2055      A  AAAAAG         C       G

2095 CTTAATCAGATAGAT    ATTCCTATTGTGCAA
2085                            -  G  A C

2125 TGTAAATATTTTAAA    GAATTGTGTC--AGA
2115                              C AA T
```

FIG.8c-13

```
2153 CTGTTTAGTAGCAGT GATTGTCTTAATATT
2145            G               A    --- C

2183 GTGGGTGTTAATTTT -TGATACTAAGCATT
2172            G                A

2212 GAATGGCTATGTTTT TAATGTATAGTA-AA
2202                                        G

2241 TCACGCTTTTTGAAA AAGCGAAAAAATCAG
2232     T                        -

2271 GTGGCTTTTGCGGTT CAGGAAAATTGAATG
2261       C  A               G C

2301 CAAACCATAGCACAG GCTAATTTTTTGTTG
2291 A    T         A            TC T

2331 TTTCTTAAATAAGAA ACTTTTTTATTTAAA
2321 C  AA  T    TG G   G--------------

2361 AAACTAAAAACTAGA GGTGAGAAATTTAAA
2338 ----------------  ----------- A C

2391 CTATAAGCAAGAAGG CAAAAATAGTTTGGA
2343         G T

2421 TATGTAAAACATTTA CTTTGACATAAAGTT
2373         C        C      T           C
```

FIG.8c-14

```
2451 GATAAAGAT-TTTTT  AATAATTTAGACTTC
2403          A         G  G   A T

2480 AAGCATGGCTATTTT  ATATTACACTACACA
2433                     C  C    T
              PstI
2510 CTGTGTACTGCAGTT  -GGTATGACCCCTCT
2463            T     CAAG A   TT A

2539 AAGGAGTGTAGCAAC  TACAGTCTAAAGCTG
2493  CA A                          C

2569 GTTTAATG-TTTTGG  CCAATGCACCTAAAG
2523     G   C   CA  T  G

2598 AAAA---ACA-AACT  CGTTTTTTACAAAG-
2553     CAC   C  G   GT           G T

2623 CCCTTTTATACCTCC  CCAGACTCCTTCAAC
2583    T   G   T     A A   A    ---

2653 AATTCTAAAATGATT  GTAGTAATCTGCATT
2609 G                  AA  T      -

2683 ATTGGAATATAATTG  TTTTATCTGAATTTT
2638    C    C   CA                C

2713 TAAACAAGTATTTGT  T-AATTTAGAAAACT
2668      T  A        A            T
```

FIG.8c-15

```
2742 TTAAAGCGTTTGCAC AGATCAACTTACCAG
2698   T   ATA        A  A      -----

2772 GCACCAAAAGAAGTA AAAGCAAAAAAGAAA
2723 --   AT   TC AA    CCAA C   C C

2802 ACCTTTCTTCACCAA ATCTTGGTTGATGCC
2751    T      T                 CG

2832 AAAAAAAAATACATG CTAAGAGAAGTAGAA
2781 --  G C GC G          G

2862 ATCATAGCTGGTTCA CACTGACCAAGATAC
2809      T             GT     CA G

2892 TTAAGTGCTGCAATT GCACGCGGAGTGAGT
2839      T  A G G    T T    C  --

2922 TTTTTAGTGCGTGCA GATGGTGAGAGATAA
2867 --         A      CCA       G

PstI
2952 GATCTATAGCCTCTG CAGCGGAATCTGTTC
2895   C      A         TAA      C

2982 ACACCCAACTTGGTT TTGCTACATAATTAT
2925   A TAT    C A    AT T    T  C

3012 CCAGGAAGGGAATAA GGTACAAGAAGCATT
2955  G A  GA      ----- ----------------
```

FIG.8c-16

```
3042 TTGTAAGTTGAAGCA  AATCGAATGAATTA
2965 ----            GG  A      GC

3072 ACTGGGTAATGAAAC  AAAGAGTTCAAGAAA
2991         A G     -----------

3102 TAAGTTTTTGTTTCA  CAGCCTATAACCAGA
3011  -   G                T   C

3132 CACATACTCATTTTT  CATGATAATGAACAG
3040        AT G CAG T   TCATGGC    -

3162 AACATAGACAGAAGA  AACAAGGTTTTCAGT
3069 ---  G A T A                  A

3192 CCCCACAGATAACTG  AAAATTATTTAAACC
3096          C       G G  C       T

3222 GCTAAAAGAAACTTT  CTTTCTCACTAAATC
3126 AGG GC     ----          C   AT

3252 TTTTATAGGATTTAT  TTAAAATAGCAAAAG
3152        A    G    -    C T

3282 AAGAAGTTTCATCAT  TTTTTACTTCCTCTC
3181      T                 --A T C

3312 TGAGTGGACTGGCCT  CAAAGCAAGCATTCA
3209 CA   A T CA              G T G
```

FIG.8c-17

```
3342 GAAGAAAA-AGAAGC AACCTCAGTAATTTA
3239    A    GAGGG  T G         G

3371 GAAATCATTTTGCAA TCCCTTAATATCCTA
3269 T   ---G    C   T          -----

3401 AACATCATTCATTTT TGTTGTTGTTGTTGT
3291 --------------- ---------------

3431 TGTTGAGACAGAGTC TCGCTCTGTCGCCAG
3291 --------------- ---------------

3461 GCTAGAGTGCGGTGG CGCGATCTTGACTCA
3291 --------------- ---------------

3491 CTGCAATCTCCACCT CCCACAGGTTCAGGC
3291 --------------- ---------------

3521 GATTCCCGTGCCTCA GCCTCCTGAGTAGCT
3291 --------------- ---------------

3551 GGGACTACAGGCACG CACCACCATGCCAGG
3291 --------------- ---------------

3581 CTAATTTTTTTGTAT TTTAGCAGAGACGGG
3291 --------------- ---------------

XhoI
3611 GTTTCACCATGTTGG CCAGGATGGTCTCGA
3291 --------------- ---------------
```

FIG.8c-18

```
3641 GTCTCCTGACCTCGT GATCCACCCGACTCG
3291 --------------- ---------------

3671 GCCTCCCAAAGTGCT GGGATTACAGGTGTA
3291 --------------- ---------------

3701 AGCCACCGTGCCCAG CCCTAAACATCATTC
3291 --------------- A      GT      T

EcoRV
3731 TTGAGAGCATTGGGA TATCTCCTGAAAAGG
3306   AGA       A      GT   -C

3761 TTTATGAAAAGAAG AATCTCATCTCAGTG
3335 A         T  GA  TA  T A CATT T

HindIII
3791 AAGAATACTTCTCAT TTTTTAAAAAAGCTT
3365       TT  TAT     C   ------------

3821 AAAACTTTGAAGTTA GCTTTAACTTAAATA
3384 -----    A        A    C

3851 GTATTTCCATTTAT CGCAGACCTTTTTTA
3409         G   G   T       -CC

HindIII
3881 GGAAGCAAGCTTAAT GGCTGATAATTTTAA
3438 A            T     AT  G    G  T
```

FIG.8c-19

```
3911 ATTC--TCTCTCTTG CAGGAAGGACTATGA
3468     CT      A T   A    A  TGG   G

3939 AAAGCTAGAATTGAG TGTTTAAAGTTCAAC
3498           CC G             T C

3969 ATGTTA-TTTGTAAT AGATGTTTGATAGAT
3528 G    A  C      G              A

3998 TTTCTGCTACTTTGC TGCTATGGTTTTCTC
3558            C                C

4028 CAAGAGCTACATAAT TTAGTTTCATATAAA
3588                               C

4058 GTATCATCAGTGTAG AACCTAATTCAATTC
3618 A         CA                C T

4088 AAAGCTGTGTGTTTG GAAG-ACTATCTTAC
3648    A A             A

4117 TATTTCACAACAGCC TGACAACATTTCTAT
3678 C           T G   A

4147 AGCCAAAAATAGCTA AATACCTCAATCAGT
3708

4177 CTCAGAATGTCATTT TGGTACTTTGGTGGC
3738                               C
```

FIG.8c-20

```
4207 CACATAAGCCATTAT TCACTAGTATGACTA
3768      C

4237 GTTGTGTCTGGCAGT TTATATTTAACTCTC
3798         CT                   T

4267 TTTATGTCTGTGGA- TTTTTTCCTTCAAAG
3828               T

4296 TTTAATAAATTTATT TTCTTGGATTCCTGA
3858                            -A AAAAA

4326 TAATGTGCTTCTGTT ATCAAACACCAACAT

4356 AAAAATGATCTAAAC CAAAAAAAAAAAAAA

4386 AAAAAAAA
```

Human Growth Hormone Receptor

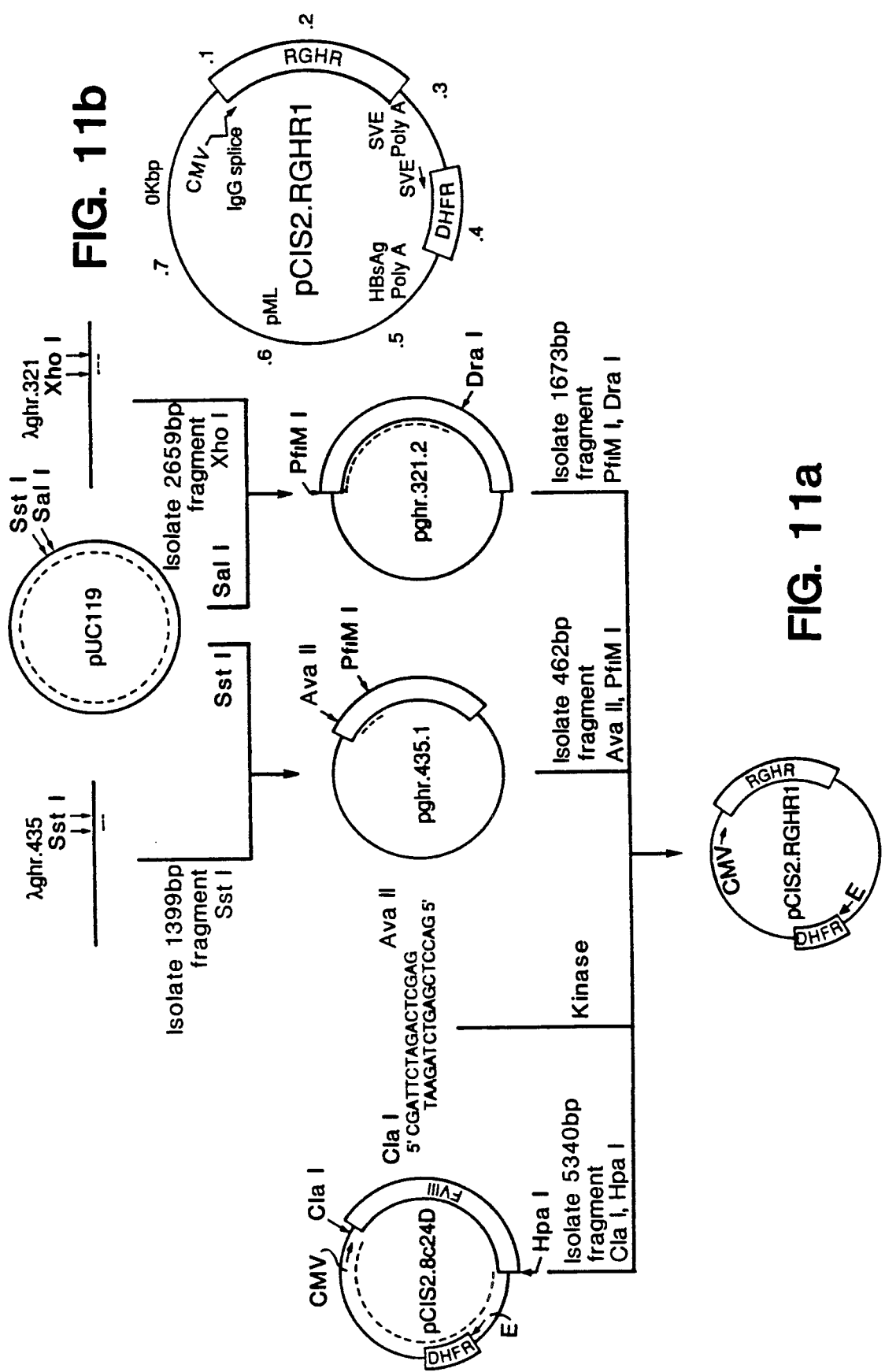

Transient Expression of Rabbit Growth Hormone Receptor in Cos Cells

Transient Expression of Rabbit Growth Hormone Receptor in Cos Cells

FIG. 14a Transient Expression of the Soluble Growth Hormone Binding Protein in 293 Cells
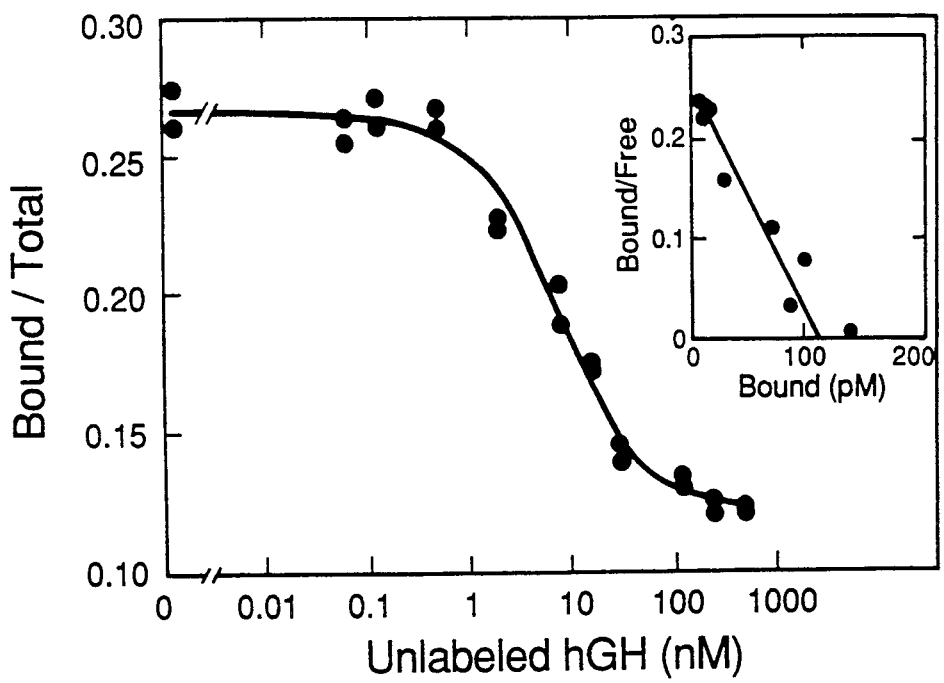
FIG. 14b Transient Expression of the Soluble Growth Hormone Binding Protein in 293 Cells
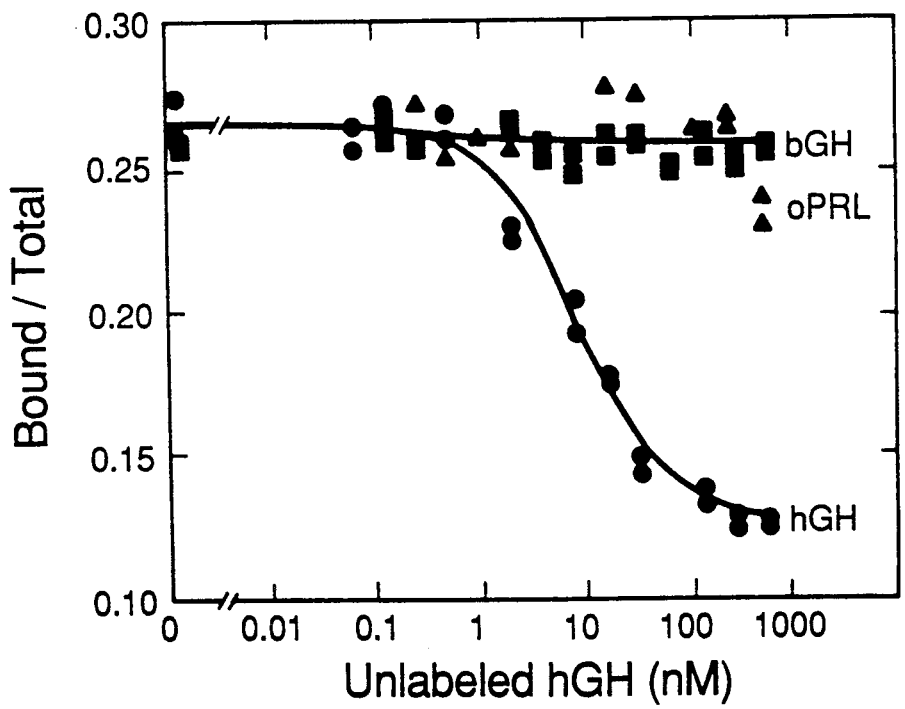

COMPOSITIONS AND METHODS FOR THE SYNTHESIS OF GROWTH HORMONE RECEPTOR AND GROWTH HORMONE BINDING PROTEIN

BACKGROUND OF THE INVENTION

This invention relates to growth hormone receptor and a novel growth hormone binding protein. The invention further relates to the synthesis of the growth hormone receptor and the growth hormone binding protein by recombinant means.

Human growth hormone (hGH) is a linear polypeptide with 191 amino acids and contains two intrachain disulfide bridges. The major biological effect of hGH is to promote growth. The organ systems affected include the skeleton, connective tissue, muscles, and viscera such as liver, intestine, and kidneys. Growth hormone exerts its action through interaction with specific receptors on cell membranes. Specific binding of growth hormone has been correlated with metabolic responses in primary cultures of adipocytes (Clemmons, D. R., et al., J. Clin. Invest. 106, 361–367[1981]; Gause, I., et al., Endocrinology 112, 1559–66[1983]). with developmental responses in a fibroblast cell line (Murphy, L. J., et al., Endocrinology 113, 750–57[1983]; Nixon, T. and Green, H. J. Cell. Physiol. 115, 291–96[1983]), and with growth responses in primary cultures of chondrocytes (Eden, S., et al., Endocrinology 112, 1127–29[1983]; Madsen, K., et al., Nature 304,545–47[1983]).

Several receptors have been cloned, for example EGF, insulin and I1-2. (See for example EP 0,192,392; EP 0,128,733; and, E.P. 0,162,699). The growth hormone receptor has been shown to be an integral membrane protein. Lectin-receptor interactions further suggest that growth hormone receptors contain a carbohydrate component associated with the extracellular domain of the receptor in conjunction with the growth hormone-binding site (Tsushima, T., at al., Biochem. J. 187, 479–92[1980]). Analysis of the growth hormone receptor by gel filtration has shown that the triton-solubilized receptor elutes with a $M_r$ of 200,000–300,000. (Waters, M. J. and Friesen, H. G. J. Biol. Chem. 254, 6815–25[1979]). It has been suggested that this technique probably overestimates the $M_r$ of the growth hormone receptor because it does not take into account the amount of Triton bound to receptor. (Hughes, J. P. et al. in Polypeptide Hormone Receptors, Posner, B. I. [ed.] [Dekker, M., N.Y.]) Recent studies have estimated the $M_r$ of the GH receptor to be in the range from 130,000 to 200,000 (rat hepatocytes, Donner, D. J. Biol Chem. 258, 2736–43[1983]; rat adipocytes, Carter-Su, C., et al., J. Biol. Chem., 259, 1099–104[1984]; and, IM-9 lymphocytes, Hughes, J. P., et al., Endocrinology 112, 1980–85[1983]). Under reducing conditions on SDS gel-electrophoresis, the $M_r$ of these receptors ranged from 108,000 to 112,000. In the absence of reducing agents, however, the GH receptor identified on rat hepatocytes migrated as a higher-$M_r$ species, suggesting that this GH receptor interacts via interchain disulfide bonds with other receptor or nonreceptor proteins (Donner, D., supra).

In contrast to the relatively high $M_r$ obtained for human and rat GH receptors in cross-linking studies, $M_r$ in the range of 50,000–67,000 have been obtained for the rabbit GH receptor in microsomal membranes (Tsushima, T., et al., FEBS Lett. 147,49–53[1982]). Additional data suggest that the GH receptor in intracellular membranes (microsomal membranes) is composed of noncovalently linked subunits, whereas the receptor on the cell surface (plasma membranes) is primarily composed of disulfide-linked subunits (Id.).

Several lines of evidence suggest the presence of two receptors in rabbit liver membranes capable of binding human growth hormone. One line of evidence is differences in binding observed when two or more GH tracers from different species are used to characterize GH receptors in the same rabbit liver preparation (Hughes, J. P., et al., Endocrinology 113,1904–6[1983]). Evidence in support of multiple classes of receptors also has been obtained from studies that have examined the binding characteristics/biological actions of cleaved forms of growth hormone (Maciag, T., et al., J. Biol. Chem. 255, 6064–70[1980]). Displacement studies using various growth hormones -rat, pig, human and bovine- and prolactin further suggest the presence of two growth hormone receptors. For example, the liver somatogenic receptor binds labelled growth hormone which label can be displaced by growth hormone but not prolactin. It was also observed that bovine or ovine prolactin can displace receptor bound human growth hormone (Waters, M. J. and Friesen, H. G., J. Biol. Chem. 254, 6815–25[1979]). Still other workers observed partial displacement by both ovine prolactin and bovine growth hormone, suggesting the presence of distinct somatogenic and lactogenic receptors, both of which bind human growth hormone. The liver may contain two types of growth hormone receptor, one with high affinity for rabbit growth hormone and relatively low affinity for human growth hormone (Hughes, J. P., Endocrinology 105, 414–20[1974]). Others suggest that the liver contains three types of receptors for hormones of the growth hormone-prolactin family, one specific for growth hormone, one specific for prolactin, and one that does not discriminate between the two (Wallis, M. et al. in Investigation of Membrane-Located Receptors eds. Reid, E et al. [Plenum Press, N.Y., 1984]).

Recently, data have accumulated suggesting the presence of a growth hormone binding protein in the serum of both humans and rabbits (Ymer, S. I. & Herrington, A. C., Mol. Cell. Endocrinol., 41, 153-161, [1985]; Herrington, A. C., et al., Proc. Annu. Meet. Endocr. Soc. Australia 28th. Adelaide, abstr. 77[1985]). Using monoclonal antibodies to the presumptive growth hormone receptor in rabbit and rat liver, there was observed a close antigenic and possible ontogenic relationship between membrane "receptor" and the cytosolic binding proteins found in the liver (Barnard, R. & Waters, M. J., J. Receptor Res. [1986]). Additional work has suggested that these cytosolic binding proteins may be newly synthesized serum binding proteins (Barnard, R. & Waters, M. J., Biochem J. 237, 885–892[1986]). The growth hormone binding protein, partially purified using hGH-affinity chromatography, was observed to be 74,000-85,000 mol, wt. and distinct from the major serum protein, human albumin (Ymer, S. I. and Herrington, A. C., Mol. and Cell. Endocr., 41:153-161 [1985]).

Many effects of growth are exerted through induction of somatomedins produced in the liver. Growth hormone binds to specific receptors on cell membranes, stimulating somatomedin generation. The net metabolic effects of growth hormone (and somatomedins) include stimulation of nucleic acid and protein synthesis, induction of positive nitrogen balance, stimulation of lipolysis, and a decrease in urea excretion. One variety of dwarfism referred to as Laron dwarfism occurs in patients in whom growth hormone is present but in whom receptors appear to be defective or absent so that somatomedin generation does not occur (Fishet et al., Isr. J. Med. Sci., 20:8-11 [1984] and Golde et al., N. Engl. J. Med., 303:1156-1159 [1980]).

Although the art has attempted to purify putative growth hormone receptors and binding proteins these preparations have been insufficiently pure to permit determination of the sequences of the growth hormone receptor and binding protein. This invention for the first time has established the precise identity of the growth hormone receptor and the ontogeny and identity of the growth hormone binding protein. It is an object of the present invention to purify the growth hormone receptor and the binding protein and DNA encoding same, and to produce useful quantities of each using recombinant DNA techniques. This and other objects of this invention will be apparent from the specification as a whole.

SUMMARY OF THE INVENTION

Objects of this invention have been accomplished by a method comprising: identifying and cloning the gene which codes for mammalian growth hormone receptor or binding protein; incorporating that gene into a recombinant DNA vector; transforming a suitable host with the vector including that gene; expressing the mammalian growth hormone receptor and binding protein in such a host; and recovering the mammalian growth hormone receptor or binding protein that is produced. Similarly, the present invention makes it possible to produce human growth hormone receptor or binding protein and/or derivatives thereof by recombinant techniques, as well as providing products and methods related to such human growth hormone receptor and binding protein.

The present invention is directed to the compositions and methods of producing mammalian growth hormone receptor and binding protein via recombinant DNA technology, including: 1) the isolation and purification and structural identity of growth hormone receptor and binding protein; 2) the discovery and identity of the entire DNA sequence of the growth hormone receptor and the 5' and 3' flanking regions thereof as well as DNA encoding the binding protein; 3) the construction of cloning and expression vehicles comprising said DNA sequence, enabling the expression of the mammalian receptor or binding protein, as well as met, fusion or N-terminal conjugates thereof; and, 4) viable cell cultures genetically altered by virtue of their containing such vehicles and capable of producing mammalian growth hormone receptor or binding protein. Yet another aspect of this invention are new compounds, including deoxyribonucleotides and ribonucleotides which are utilized in hybridizing with DNA encoding growth hormone receptor and binding protein.

Still another aspect of the present invention is growth hormone receptor or binding protein which is essentially pure as defined herein, exhibits specific activity beyond that obtained before this invention and is in sufficient purity that N-terminal amino acid sequence can be obtained. In addition, depending upon the method of production, the growth hormone receptor and binding protein hereof may contain associated carbohydrate to a greater or lesser extent or composition compared with material obtained from its in vivo physiological milieu, i.e. blood and/or tissue.

The growth hormone receptor and binding protein of this invention includes mature growth hormone receptor and binding protein, pre-growth hormone receptor and binding protein and growth hormone receptor and binding protein derivatives including (a) fusion proteins wherein growth hormone receptor or binding protein or any fragment thereof is linked to other proteins or polypeptides by a peptide bond at the amino and/or carboxyl terminal amino acids of growth hormone receptor or binding protein; (b) growth hormone receptor and binding protein fragments in which any amino acid from the signal sequence is the amino-terminal amino acid of the fragment; (c) variants of growth hormone receptor or binding protein, or fragments thereof, wherein one or more amino acid residues are substituted, inserted or deleted; and/or (d) methionyl or modified methionyl (such as formyl methionyl or other blocked methionyl species) amino-terminal addition derivatives of the foregoing proteins, fragments or variant.

Recombinant growth hormone receptor and binding protein thereof are purified and then combined for therapeutic use with physiologically innocuous stabilizers and excipients, sterile filtered and placed into dosage form as by lyophilization in dosage vials or storage in stabilized aqueous preparations.

The mammalian growth hormone receptor and modified binding protein may be useful in the treatment of various pathological disorders, e.g. gigantism and acromegaly associated with growth hormone excess provided the modified binding protein has a higher affinity for growth hormone. Thus, growth hormone receptor and binding protein compositions are administered to animals in therapeutically effective doses to reduce excessive circulating levels of growth hormone. The novel DNA of this invention or DNA which hybridizes thereto may also be used to screen children exhibiting retarded growth for defects in the growth hormone receptor, e.g. Laron dwarfism. Growth hormone binding protein and derivatives thereof are useful in the treatment of pathological disorders associated with growth hormone deficiency. Growth hormone binding protein could increase the in vivo stability and efficacy of growth hormone. Thus growth hormone and growth hormone binding protein would be administered in a composition to promote growth in growth hormone deficient patients. Suitable dosages will be apparent to the physician in the therapeutic context. Growth hormone receptor and binding protein are useful in affinity purification of growth hormone or in receptor binding assays. These assays would be an improvement over presently available immunoassays.

BRIEF DESCRIPTION OF THE DRAWINGS

FIG. 3. (d-f) Hormone binding competition curves for the liver GH receptor MgCl$_2$ (d) and urea (e) eluates and the serum binding protein MgCl$_2$ eluate (f). $^{125}$I-hGH was the tracer and human GH ( ), bovine GH ( ) and ovine prolactin (Δ). The competing ligands. Each measurement in triplicate.

FIG. 4. Binding activity profile for the serum binding protein fractions from the sephacryl S300 gel filtration column. A single peak of activity at approximately 96kD was observed.

FIG. 8a. DNA and translated amino acid sequence of the human growth hormone receptor cDNA clone. Selected restriction sites are also shown.

FIG. 8a-1 through FIG. 8a-13 depict the DNA and translated amino acid sequence in order.

FIG. 8b. DNA and translated amino acid sequence of the rabbit growth hormone receptor cDNA clone. Selected restriction sites are also shown.

FIG. 8b-1 through FIG. 8b-12 depict the DNA and translated amino acid sequence in order.

FIG. 8c. Homology of the DNA and amino acid sequences of the human and rabbit growth hormone receptors. Line 1. human DNA sequence; line 2, differences for the rabbit DNA sequence; line 3, the human translated amino acid sequence; and line 4, differences for the rabbit amino acid sequence. The DNA sequences are numbered starting with the 1 at the initiating ATG; the protein sequence with the 1 at the mature N-terminal phenylalanine. DNA sequence analysis was performed by the dideoxy chain termination method using fragments cloned in the pUC 118/119 vectors.

FIG. 8c-1 through FIG. 8c-20 depict the DNA and amino acid sequences in order.

FIG. 9. Blot hybridization of the rabbit growth hormone receptor mRNA. 5 μg of rabbit liver RNA was electrophoresed in a 1% agarose gel containing 2.2M formaldehyde, transferred to nitrocellulose and hybridized to a $^{32}$P labelled probe prepared from equal amounts of a 844 bp XbaI-SspI and a 1297 bp SspI fragment spanning the entire coding region of the rabbit growth hormone receptor derived from the rabbit growth hormone receptor expression vector pCIS2.RGHR1.

FIG. 10. Schematic of the human growth hormone receptor. The hydropathy plot is from the method of Kyte and Doolittle, J. Mol. Biol., 153.105-132 (1982) with a window of 10 residues. The potential N-linked glycosylation sites are Asn-X-(Ser Thr). The homology with the rabbit receptor is for exact matches over a window of 10 amino acids.

FIG. 11a. Construction of the rabbit growth hormone receptor expression plasmid, pCIS2.RGHR1.

FIG. 11b. Map of the rabbit growth hormone receptor expression plasmid, pCIS2.RGHR1.

FIG. 12. (a-c) Construction of an expression vector for human soluble growth hormone binding protein.

FIG. 13. (a, b) Growth hormone binding to the rabbit receptor expressed in mammalian cells COS-7 monkey kidney cells were transfected with pCIS2. RGHR1 by the calcium phosphate precipitation method. (a) Cell membranes were prepared and assayed for binding competition between $^{125}$I-hGH and unlabelled hGH, Scatchard plot (insert) of the same data. (b) Binding competition curves with $^{125}$I-hGH and unlabelled hGH ( ), bovine growth hormone ( ), or ovine prolactin (Δ) as the competing ligands.

FIG. 14a. Growth hormone binding to the human soluble growth hormone binding protein. 293 human kidney cells were transfected with pCIS2.sHGHR by the calcium phosphate method. Culture medium from the cells was assayed for binding competition between $^{125}$I-hGH and unlabelled hGH; insert, Scatchard plot of the same data.

FIG. 14b. Binding competition between $^{125}$I-hGH and unlabelled hGH ( ), bovine growth hormone (+), or ovine prolactin (X).

DETAILED DESCRIPTION

Figures 1A, 1B:
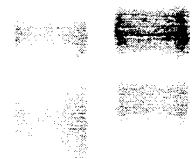
FIG. 1a. Silver-stained 9.5% SDS polyacrylamide gel of the affinity purification steps for the liver GH receptor. Approximately 1 μg total protein per lane; samples reduced except as noted. The arrow indicates the top of the resolving gel. Lane 1—affinity column load; lane 2—flow-through; lane 3—wash; lane 4—urea; lane 5—$MgCL_2$ eluate; lane 6—non-reduced $MgCL_2$ eluate.
FIG. 1b. Immunoblot with anti-receptor monoclonal antibody #5 of reduced liver GH receptor ($MgCl_2$) eluate, showing preferential staining of the 130 kD band plus two weaker bands around 100 kD. Lane 1—starting with frozen liver (note degradation); Lane 2—starting with fresh liver.

As used herein, growth hormone receptor and growth hormone binding protein and derivatives thereof refers to nonimmune polypeptides capable of recognizing and selectively interacting, that is binding, with growth hormone. Such binding may be established using, for example, displacement studies as described herein.

Included within the scope of growth hormone receptor and growth hormone binding protein as those terms are used herein are growth hormone receptor and binding protein having native glycosylation and the amino acid sequences, in the case of rabbit and human growth hormone receptor, as set forth in FIGS. 8a and 8b, and in the case of the growth hormone binding protein the amino acid sequence of at least about the first 190 amino acids from the amino terminal end extending to at least about 250 amino acids, analogous growth hormone receptor and binding protein from other animal species such as bovine, porcine and the like, deglycosylated or unglycosylated derivatives of such growth hormone receptor and binding protein, amino acid sequence variants of growth hormone receptor and binding protein and in vitro-generated covalent derivatives of growth hormone receptor and binding protein. Ordinarily growth hormone receptor and binding protein polypeptides will be about from 40 to 100 percent homologous to the sequence in FIGS. 8a and 8b, preferably 75 to 90 percent homologous. All of these forms of growth hormone receptor and binding protein will bind growth hormone.

Pre-growth hormone receptor and binding protein is a species of receptor and binding protein included within the foregoing definition. It is characterized by the presence in the molecule of a signal (or leader) polypeptide which serves to posttranslationally direct the protein to a site inside or outside of the cell. Generally, the signal polypeptide (which will not have growth hormone binding capability in its own right) is proteolytically cleaved from a residual protein having growth hormone binding activity as part of the secretory process in which the protein is transported into the host cell periplasm or culture medium. The signal peptide may be microbial or mammalian, including the native 18 amino acid presequence, but it preferably is mammalian.

Amino acid sequence variants of growth hormone receptor and binding proteins of FIGS. 8a and 8b fall into one or more of three classes: substitutional, insertional or deletional variants. The variants ordinarily are prepared by site specific mutagenesis of nucleotides in the DNA encoding the growth hormone receptor and binding protein, hereby producing DNA encoding the variant, and thereafter expressing the DNA in recombinant cell culture. However, variant growth hormone receptor and binding protein fragments having up to about 100-150 residues may be conveniently prepared by in vitro synthesis. Amino acid sequence variants are ordinarily characterized by the predetermined nature of the variation, but such variants include naturally occurring allelic or interspecies variation of the growth hormone receptor and binding protein amino acid sequence. The variants typically exhibit the same qualitative biological activity as the naturally-occurring analogue, although variants also are selected in order to modify the characteristics of growth hormone receptor and binding protein as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed growth hormone receptor and binding protein variants screened for the optimal combination of desired activity. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. Obviously, the mutations that will be made in the DNA encoding the variant growth hormone receptor and binding protein must not place the sequence out of reading frame and preferably will not create complementary regions that could produce secondary mRNA structure (EP 75,444A).

Substitutional variants are those in which at least one residue in the FIG. 8a and b sequence has been removed and a different residue inserted in its place. Such substitutions generally are made in accordance with the following Table 1 when it is desired to finely modulate the characteristics of growth hormone receptor and binding protein.

TABLE 1

| Original Residue | Exemplary Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu., val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in growth hormone receptor and binding protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A major class of substitutional or deletional variants are those involving the transmembrane and/or cytoplasmic regions of growth hormone receptor. The cytoplasmic domain of growth hormone receptor is the sequence of amino acid residues commencing at about amino acid 271 in FIGS. 8a,b and continuing for approximately 350 additional residues. In the rabbit and human sequence the Lys-Gln-Gln-Arg-Ile-Lys domain (residues at about 270 through 276) is believed to serve as a stop transfer sequence; the electropositive character provided by the basic residues act, together with the transmembrane region described below, to bar transfer of growth hormone receptor through the cell membrane.

The transmembrane region of growth hormone receptor is located in the human sequence at about residues 247-269 and in the rabbit sequence at the analogous location. This region is a highly hydrophobic domain, which is the proper size to span the lipid bilayer of the cellular membrane. (See hydropathy profile in FIG. 10). It is believed to function in concert with the cytoplasmic domain to anchor the recognition and binding portion of growth hormone receptor, i.e. growth hormone binding protein, in the cell membrane.

Deletion or substitution of either or both of the cytoplasmic and transmembrane domains will facilitate recovery of recombinant growth hormone binding protein from the growth hormone receptor by reducing its cellular or membrane lipid affinity and improving its water solubility. In the case of growth hormone receptor the cytoplasmic or transmembrane domains may be deleted to facilitate recovery of recombinant growth hormone receptor by reducing its cellular or membrane lipid affinity and improving its water solubility so that detergents will not be required to maintain the growth hormone receptor in aqueous solution. Preferably, both the cytoplasmic and transmembrane domains are deleted.

The cytoplasmic and/or transmembrane (C-T) deleted or substituted growth hormone binding protein can be synthesized directly in recombinant cell culture or as a fusion with a signal sequence, preferably a host-homologous signal. For example, in constructing a procaryotic expression vector, the C-T domains are deleted and the bacterial alkaline phosphatase. STII or heat stable enterotoxin II leaders replace the naturally occurring 18 amino acid signal, while in yeast, invertase, alpha factor or acid phosphatase leaders may be used. In mammalian cell expression a mammalian cell viral secretory leader may be used, for example the herpes simplex gD signal. When the secretory leader is "recognized" by the host, the host signal peptidase is capable of cleaving a fusion of the leader polypeptide fused at its C-terminus to growth hormone binding protein, i.e., C-T deleted growth hormone receptor. One advantage of growth hormone binding protein is that it is capable of being secreted into the culture medium. This variant is water soluble and does not have an appreciable affinity for cell membrane lipids, thus considerably simplifying its recovery from recombinant cell culture.

Substitutional or deletional mutagenesis is employed to eliminate N- or O-linked glycosylation sites. Alternatively, unglycosylated growth hormone receptor and binding protein is produced in recombinant prokaryotic cell culture. Deletions of cysteine or other labile residues also may be desirable, for example in increasing the oxidative stability of the growth hormone receptor and binding protein. Deletions or substitutions of potential proteolysis sites, e.g. Arg Arg, is accomplished by deleting one of the basic residues or substituting one by glutaminyl or histidyl residues.

Insertional amino acid sequence variants of growth hormone receptor and binding proteins are those in which one or more amino acid residues are introduced into a predetermined site in the target growth hormone receptor and binding protein. Most commonly, insertional variants are fusions of heterologous proteins or polypeptides to the amino or carboxyl terminus of growth hormone receptor and binding protein. Immunogenic growth hormone receptor and binding protein derivatives are made by fusing an immunogenic polypeptide to the target sequence by cross-linking in vitro or by recombinant cell culture transformed with DNA encoding the fusion. Such immunogenic polypeptides preferably are bacterial polypeptides such as trpLE, beta-galactosidase and the like, together with their immunogenic fragments.

DNA encoding growth hormone receptor and binding protein is obtained from other sources than rabbit or human by a) obtaining a cDNA library from the liver of the particular animal, b) conducting hybridization analysis with labelled DNA encoding human growth hormone receptor and binding protein or fragments thereof (usually, greater than 100 bp) in order to detect clones in the cDNA library containing homologous sequences, and c) analyzing the clones by restriction enzyme analysis and nucleic acid sequencing to identify full-length clones. If full length clones are not present in the library, then appropriate fragments may be recovered from the various clones and ligated at restriction sites common to the clones to assemble a full-length clone.

Growth hormone receptor and binding protein includes amino acid sequence mutants, glycosylation variants and covalent or aggregative conjugates with other chemical moieties. Growth hormone receptor and binding protein include covalent derivatives prepared by linkage of functionalities to groups which are found in the growth hormone receptor and binding protein amino acid side chains or at the N, or C-termini, by means known in the art. These derivatives may, for example, include: aliphatic esters or amides of the carboxyl terminus or residues containing carboxyl side chains, O-acyl derivatives of hydroxyl group-containing residues, and N-acyl derivatives of the amino terminal amino acid or amino-group containing residues, e.g. lysine or arginine. Acyl groups are selected from the group of alkyl-moieties (including C3 to C18 normal alkyl), thereby forming alkaloyl aroyl species.

A major group of derivatives are covalent conjugates of growth hormone receptor and binding protein or their fragments with other proteins or polypeptides. These derivatives are synthesized in recombinant culture as N, or C-terminal fusions or by the use of difunctional agents known per se for use in cross-linking proteins to insoluble matrices through reactive side-groups. Preferred growth hormone receptor and binding protein derivatization sites with cross-linking agents are at cysteine and lysine residues. Preferred agents are M-Maleimidobenzoyl succinimide ester and N-hydroxysuccinimide.

Covalent or aggregative derivatives are useful as immunogens, reagents in immunoassay or for affinity purification procedures of growth hormone or other binding ligands. For example, growth hormone receptor and binding protein is insolubilized by covalent bonding to cyanogen bromide-activated Sepharose by methods known per se or adsorbed to polyolefin surfaces (with or without glutaraldehyde cross-linking) for use in the assay or purification of anti-growth hormone receptor and binding protein antibodies or growth hormone. Growth hormone receptor and binding protein also is labelled with a detectable group, e.g., radioiodinated by the chloramine T procedure, covalently bound to rare earth chelates or conjugated to another fluorescent moiety for use in diagnostic assays.

Compositions comprising growth hormone receptor and binding protein may include such substances as the stabilizers and excipients described below, predetermined amounts of proteins from the cell or organism that served as the source of DNA encoding the growth hormone receptor and binding protein, proteins from other than the growth hormone receptor and binding protein source cells or organisms, and synthetic polypeptides such as poly-L-lysine. Recombinant growth hormone receptor and binding protein which is expressed in allogeneic hosts of course will be expressed completely free of gene source proteins. Expression of human growth hormone receptor or binding protein in CHO or other nonhuman higher mammalian cells results in a composition where the receptor is not only free of biological adventitious agents but also human proteins.

DNA which encodes growth hormone receptor and binding protein is obtained by chemical synthesis, by screening reverse transcripts of mRNA from placental cells or cell line cultures, or by screening genomic libraries from any cell. Also included within the scope herein is nucleic acid which may not encode the receptor or binding protein but which nonetheless is capable of hybridizing with DNA encoding the receptor or binding protein under low stringency conditions.

This DNA is covalently labelled with a detectable substance such as a fluorescent group, a radioactive atom or a chemiluminescent group by methods known per se. It is then used in conventional hybridization assays. Such assays are employed in identifying growth hormone receptor and binding protein vectors and transformants as described in the examples infra, or for in vitro diagnosis such as detection of the aberrant growth hormone receptor and binding protein DNA or mRNA in tissue samples.

The present invention provides novel growth hormone receptor and binding protein compositions. In one embodiment the growth hormone receptor or binding protein is "essentially pure" meaning that growth hormone receptor or binding protein produced by the invention means free of biological adventitious agents normally associated with growth hormone receptor or binding protein in its in vivo physiological milieu as for example when growth hormone receptor or binding protein is obtained from blood and/or tissues by extraction and purification. Examples of such biological adventitious agents are bacteria, fungi, mycoplasma, proteins and viruses, e.g. of recent note is the AIDS virus.

In a further embodiment growth hormone receptor produced by the method of the instant invention has a specific activity of greater than about 3000 pmoles/mg while the growth hormone binding protein has a specific activity of at least about 10,000 pmoles/mg.

In yet another embodiment preparation of growth hormone receptor or binding protein are provided such that amino acid sequence can be obtained of said receptor or binding protein.

In general, prokaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (F−, λ−, prototrophic, ATTC No. 27325), acilli such as *Bacillus subtilus*, and other enterobacteriaceae such as *Salmonella typhimurium* or *Serratia marcescans*, and various pseudomonas species may be used.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., Gene 2: 95 [1977]), pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., "Nature", 275: 615 [1978]; and Goeddel et al., "Nature" 281: 544 [1979]), alkaline phosphatase, the tryptophan (trp) promoter system (Goeddel "Nucleic Acids Res." 8: 4057 [1980] and EPO Appln. Publ. No. 36,776) and hybrid promoters such as the tac promoter (H. de Boer et al., "Proc. Natl. Acad. Sci. USA" 80: 21–25 [1983]). However, other functional bacterial promoters are suitable. Their nucleotide sequences are generally known, thereby enabling a skilled worker operably to ligate them to DNA encoding growth hormone receptor and binding protein (Siebenlist et al., "Cell" 20: 269 [1980]) using linkers or adaptors to supply any required restriction sites. Promoters for use in bacterial systems also will contain a Shine-Dalgarno (S.D.) sequence operably linked to the DNA encoding growth hormone receptor and binding protein.

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example, (Stinchcomb, et al., Nature 282: 39 [1979]; Kingsman et al, Gene 7: 141 [1979]; Tschemper et al., Gene 10: 157 [1980]) is commonly used. This plasmid already contains the trpl gene which provides a selection marker for a mutant strain of yeast lacking the ability to grow in tryptophan, for example ATCC no. 44076 or PEP4-1 (Jones, Genetics 85: 12 [1977]).

Suitable promoting sequences for use with yeast hosts include the promoters for 3-phosphoglycerate kinase (Hitzeman et al., "J. Biol. Chem." 255: 2073 [1980]) or other glycolytic enzymes (Hess et al., "J Adv. Enzyme Reg." 7: 149 [1968]; and Holland, "Biochemistry" 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the transcribed mRNA.

Preferred promoters controlling transcription from vectors in mammalian host cells may be obtained from various sources, for example, the genomes of viruses such as: polyoma. Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment Greenaway, P. J., et al., Gene 18: 355-360 (1982). Of course, promoters from the host cell or related species also are useful herein.

Transcription of a DNA encoding growth hormone receptor and binding protein by higher eukaryotes is increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins, L. et al., PNAS 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding growth hormone receptor and binding protein. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol Cell. Biol. 5: 410-413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the vectors of this invention encoding growth hormone receptor and binding protein in higher eukaryotes include: monkey kidney CV1 line transformed by SV40 (COS-7, ATCC CRL 1651); human embryonic kidney line (293, Graham, F. L. et al. J. Gen Virol. 36: 59 [1977]); baby hamster kidney cells (BHK, ATCC CCL 10); chinese hamster ovary-cells-DHFR (CHO, Urlaub and Chasin, PNAS (USA) 77: 4216, [1980]); mouse sertoli cells (TM4, Mather, J. P., Biol. Reprod. 23: 243-251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI38, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44-68 [1982]).

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456-457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform E. coli K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Growth hormone receptor and binding protein or anti-growth hormone receptor is prepared for administration by mixing growth hormone receptor and binding protein or anti-growth hormone receptor having the desired degree of purity with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using gel electrophoresis described by Maniatis, T. et. al., *Molecular Cloning* pp. 133-134 (1982).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loon that would impede insertion of another DNA fragment at the restriction site. Procedures and reagents for dephosphorylation are conventional. Maniatis, T. et al., *Molecular Cloning* pp. 133-134 (1982). Reactions using BAP are carried out in 50 mM Tris a 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 μg of approximately equmolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in 10 mM MgCl$_2$, 1 mM dithiothreitol 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

EXAMPLE 1

Growth Hormone Receptor Purification a) hGH Affinity Gel Preparation

The affinity gel was prepared largely as described by Roy, S. K. et al., J. Chromatog. 303:225–228 (1984). 0.96 g glceryl controlled-pore glass was suspended in 10 ml 0.1% sodium m-periodate in distilled water and agitated 30 min, at room temp., then washed quickly with 2×10 ml cold distilled water. 10 mg hGH in 9.3 ml phosphate-buffered saline pH 7.4 were added to the activated gel along with approximately 5 mg sodium cyanoborohydride. The mixture was rotated slowly overnight a: 4° C., at which time a protein assay of the supernatant indicated 85% coupling. Remaining reactive sites were blocked by adding 5 ml 2M ethanolamine-HCl pH 8 with approximately 5 mg sodium cyanoborohydride and rotating at 4° C. for 48 hrs. The gel was then washed on a sintered glass funnel with three cycles of alternating pH 4 sodium acetate plus 0.5M NaCl and pH 8.5 Tris-HCl plus 0.5M NaCl, 50 ml for each wash. This was followed by 50 ml 50 mM Tris-HCl plus 0.1% Triton X-100 (Tris-Triton), 20 ml 6M urea in Tris-Triton, 50 ml Tris-Triton, 20 ml 5M MgCl$_2$ in Tris-Triton, 30 ml Tris-Triton, 13 ml 4.5M urea in Tris-Triton (flow stopped for 30 min.) and finally 200 ml Tris-Triton. The gel contained approximately 3.5 mg hGH/ml of gel and was stored at 4° C. in Tris-Triton plus 0.02% sodium azide.

b) Liver Receptor Extraction

The growth hormone (GH) receptor was purified from rabbit liver by membrane solubilization in Triton-X100 and GH affinity chromatography. The purification was monitored by the assay of specific, high-affinity $^{125}$I-human growth hormone (hGH) binding to the receptor. Overall the receptor was purified 59,000 fold with a yield of 30% largely by the use of affinity chromatography. The purified material had a major band at 130 kD on reduced SDS gel electrophoresis that was identified as the receptor (see below). At this stage the receptor was estimated to be 40% pure based on SDS gel analysis and a maximum theoretical specific binding of 7,700 pmoles/mg assuming 1 mole of hormone binding per 130 kD receptor. The high affinity binding constant for hGH to the purified receptor is $Ka = 30 \times 10^9 M^{-1}$ (see below, FIG. 3).

The purification followed the procedure of Waters and Friesen (J. Biol. Chem., 254:6815–6825 [1979]) with several important improvements and modifications. First, proteolysis of the receptor was prevented by the use of freshly obtained rabbit liver and by the extensive use of protease inhibitors during the purification. Purification from frozen rabbit liver or aging of the purified receptor gave little loss in binding activity but when analyzed by SDS gel electrophoresis, the isolated material contained little of the 130 kD band and much more of a broad band of 50–60 kD. This proteolysis is the likely explanation for the 50-67 kD size reported by others for rabbit liver receptor. Molecular weights of about 110 kD have been reported based on cross linking experiments for the growth hormone receptor from IM-9 lymphocytes (Asakawa, K. et. al., Biochem J. 238, 379–386 [386]); rat adipocytes (Carter-su, C. et. al., J. Biol. Chem 259, 1099–1104 [1986]); and rat hepatocytes (Donner, D., J. Biol. Chem. 258, 2736–2743 [1983]).

The second major improvement was optimization of the GH affinity column. The column was reduced in size to minimize non-specific binding and the more stable support, glycerol controlled pore glass was used in combination with a more stable coupling method. (Roy S. K., supra). This column support allowed the use of extensive washes including 4.5M urea (in which only 11% of the activity eluted, Table 1). MgCl$_2$ elutions of the affinity column gave a 12.500-fold purification.

The 130 kD SDS gel band was identified as the receptor by immunoblotting (FIG. 1b). Several anti-receptor monoclonal antibodies had previously been characterized, but only one, Mab5, bound well to the SDS denatured and reduced receptor. This antibody strongly labelled the 130 kD band as well as two sharp bands at about 100 kD (FIG. 1b). Several lower molecular weight bands, presumably degradation products also became visible upon longer development. Mab5 had been previously shown to precipitate the receptor binding activity from solubilized membranes (Barnard, R. et. al., Endocrinology 115, 1805–1813 [1984]). Two other monoclonal antibodies, Mab7 and 263 which bind near the hormone binding site also specifically bind the 130 kD band but the signal produced upon immunoblotting the reduced receptor is much weaker. SDS gel electrophoresis of the non-reduced receptor gave a high molecular weight complex that barely entered the gel (FIG. 1a) and which did not resolve into bands even at a low percentage of acrylamide. Significant GH binding activity was not recovered from the reduced and SDS denatured material.

Young (2 kg) female New Zealand White rabbits were anesthetized and their livers removed and immediately placed in ice-cold buffer containing 0.3M sucrose, 10 mM tri-HCl and 1 mM EDTA pH 7.4. Processing times were minimized by using only 3–4 rabbits for each preparation. The livers were weighed, cut into small (≦0.5 cm) pieces and suspended in 5 volumes (v/w) fresh ice-cold sucrose buffer containing 30,000 kallikrein inhibitor units (KIU) per liter of aprotinin and 2 mM phenylmethylsulfonyl fluoride (PMSF). The PMSF was dissolved in 5 ml isopropanol and added immediately before use. The suspension was homogenized (Tekmar model SDT-1810 homogenizer with SDT-182EN probe) at high speed until uniform (approx. 2 min.), while maintaining the temperature below 4° C. Benzamidine hydrochloride, dissolved in a small amount of 50 mM Tris-Cl pH 7.4, was added to 10 mM and mixed, then the homogenate was centrifuged at 14,000×g (Sorval GS3 rotor 9000 rpm) for 20 min. at 4° C. The supernatant was filtered through a fiberglass screen to remove the fat layer which sometimes formed on the surface then centrifuged at 142,000×g (Beckman 45 Ti rotor, 35,000 rpm) for 60 min. at 4° C. The top fat layer and clear supernatant were discarded and the pellet resuspended in 1.5 volumes (based on original liver weight) of room temperature 50 mM Tris-HCl pH 7.4 containing 1% Triton X-100 (TX-100), 50,000 KIU/l aprotinin, 7 μg/ml each of pepstatin and leupeptin, 1 mM PMSF and 1 mM α-aminoacetonitrile. The pellet was briefly homogenized (Tekmar) at ¼ speed until uniform (approximately 30 sec.) then placed on a magnetic stirrer at room temperature. Benzamidine hydrochloride was added to 10 mM and the suspension stirred at moderate speed for 20 min. The extract was centrifuged at 235,000×g (Beckman 45 Ti rotor, 45,000 rpm) for 90 min. at 4° C. The resulting clear red extract was carefully removed with a 50 ml syringe, taking care not to disturb the pellet or withdraw the small fay layer on the surface. To this extract were added PMSF to 1 mM, NaCl to 150 mM and $MgCl_2$ to 12 mM. This solution was loaded onto the affinity column.

c) Affinity Chromatography

The ice-cold liver membrane extract was loaded at 18 ml/hr onto a 1 ml hGH affinity column at 4°–8° C. The column was then washed with 10 ml ice-cold 1% TX-100 in 50 mM Tris-HCl pH 7.4 at 18 ml/hr, 50 ml ice-cold 1% TX-100 plus 0.5M NaCl in 50 mM Tris-HCl pH 7.4 at 150 ml/hr and finally with 10 ml ice-cold Tris-Triton at 150 ml/hr. The column was warmed to room temperature and eluted with 5 ml room temperature 4.5M urea in Tris-Triton by allowing 1 ml to flow into the column and stopping the flow for 10 min. This was repeated for the next 3 ml, each time waiting 10 min., then the final 1 ml was allowed to flow through followed by 2 ml Tris-Triton. The urea fractions were collected together into 5 ml ice-cold Tris-Triton containing 10 mM benzamidine HCl. The column was then eluted with 5 ml room temperature 4.5M $MgCl_2$ in Tris-Triton (actual pH approx. 5) followed by 2 ml Tris-Triton. This eluate was also collected into 5 ml cold Tris-Triton containing 10 mM benzamadine-HCl. The urea and $MgCl_2$ eluates were dialyzed at 4° C. against 2×1 liter of the same buffer, then stored at −80° C.

Some samples of the $MgCl_2$ eluate were acetylated at this stage by adding solid guanidine-HCl to the dialyzed sample to a final concentration of 5.3M and adjusting the pH to 8.5 with 1M sodium hydroxide. Dithiothreitol (DTT) was added to 10 mM, then the solution was sealed in a tube under nitrogen and stored in the dark overnight at 4° C. In subdued light, iodoacetic acid dissolved in 1M NaOH (approximately pH 7.5) was added to the sample to 50 mM final concentration and the pH adjusted to 8–8.5. The sample was purged with nitrogen and incubated in the dark at room temperature for 25 min. 2-mercaptoethanol was then added to 1% (V/V) and the sample dialyzed at 4° C. in the dark against 2×1 liter Tris-Triton containing 10 mM benzamide-HCl.

EXAMPLE 2

Growth Hormone Binding Protein Purification

The GH serum binding protein was purified 400,000 fold with a 14% yield by a two step procedure starting with frozen rabbit serum. The procedure used a GH affinity column like that used for the liver receptor followed by a gel filtration column under non-reducing conditions which removed a contaminant that comigrated with the serum binding protein on reduced SDS gel electrophoresis. The final material was judged to be greater than 70% pure based on SDS gel analysis and a maximum theoretical binding of 20,000 pmoles/mg assuming 1 mole of GH binding per 51 kD.

The serum binding protein was purified in a similar fashion to the liver receptor. 500 ml frozen rabbit serum was allowed to thaw at 4° C., during which time aprotinin was added to 50,000 KIU/l and benzamidine-HCl (dissolved in 10 ml 50 mM Tris-HCl pH 7.4) was added to 10 mM. Once the serum was thawed, PMSF was added to 2 mM and $MgCl_2$ to 12 mM, then the serum was centrifuged at 16,000×g (Sorval GSA rotor, 10,000 rpm) at 4° C. for 20 min. The supernatant was filtered through Whatman 541 filter paper to remove floating fat particles then placed in an ice bath and loaded onto the affinity column as described above. Cross-contamination with the liver receptor was prevented by using a separate affinity column. The column was washed with 15 ml ice-cold 50 mM Tris-HCl pH 7.4 at 18 ml/hr, 50 ml ice-cold Tris-Triton containing 0.5M NaCl at 150 ml/hr and 10 ml ice-cold 50 mM Tris-HCl pH 7.4 at 150 ml/hr. Elution was performed as described above except the elution buffers contained no TX-100. However, TX-100 was retained in the dilution and dialysis buffers to reduce potential losses during dialysis. Dialyzed fractions were stored at −80° C.

The presence of a contaminant which runs just at the top of the binding protein band on SDS gels made it necessary to include a gel filtration step before electroelution. A 1×47 cm Sephacryl S300 column was equilibrated at room temperature with 50 mM Tris-HCl pH 7.4 containing 0.15M NaCl and 0.02% $NaN_3$. The dialyzed $MgCl_2$ eluate from the affinity column was concentrated at 4° C. to approximately 0.5 ml with a Centricon 30 concentrator (Amicon) and layered onto the gel filtration column. The binding protein was eluted at room temperature at a flow rate of 6 ml/hr. 0.5 ml fractions were collected and assayed for binding activity, then pooled based on the assay results and an SDS gel of the fractions.

EXAMPLE 3

Growth Hormone Binding Assays a) Protein Radiolabeling

Human growth hormone was iodinated by the lactoperoxidase method (Thorell, J. I. et al., Biochem. Biophys. Acta, 251:363–369 [1971]). 10 µl hGH (1 mg/ml in 5 mM sodium phosphate pH 7.4), 20 µl 0.3M sodium phosphate pH 7.0, 5 µl lactoperoxidase (35 µg/ml in 0.1 M sodium phosphate pH 7.0) and 10 µl carrier-free $Na^{125}I$ (100 mCi/ml) were combined, then 25 µl 0.65 mM $H_2O_2$ were added to start the reaction. After 5 min., the reaction was stopped by adding 0.5 ml phosphate buffered saline (PBS) pH 7.4 containing 0.1% (w/v) BSA and 0.02% (w/v) sodium azide. Monomeric $^{125}I$-hGH was isolated on a 1.5×45 cm Sephadex G-75 column equilibrated with the same buffer. Approximately 2.5 ml fractions were collected into tubes containing 0.5 ml PBS with 3% (w/v) BSA and 0.02% (w/v) sodium azide. To avoid dimer contamination, only the peak and descending fractions of the hGH peak were pooled and stored at −20° C. Specific activity, calculated by the method of Greenwood et al. (Biochem J. 89:114–123 [1963]), varied from 44–144 µCi/µg.

For iodination of the purified receptor or binding protein the iodogen method was used (Fraker, P. J. et al., Biochem. Biophys. Res. Commun., 80:849–857 [1978]) Polypropylene tubes (12×75 mm) were coated with 10 µl of a 1 mg/ml iodogen solution in chloroform. Just before use the tubes were rinsed with distilled water and 50–100 µl of protein solution in Tris-Triton were added along with 5 µl (0.5 mCi) $Na^{125}I$. The reaction mixture was incubated on ice for 20 min. then transferred to 1 ml ice-cold acetone and incubated on ice for 20 min. The precipitated protein was centrifuged at 16,000×g for 10 min. and the supernatant discarded. The pellet was washed with 1 ml of ice-cold acetone and centrifuged as before. The pellet was dissolved in Tris-Triton and stored at −80° C. Specific activity was not determined but 0.2–0.5% of the total $^{125}$I counts were acetone precipitable.

b) hGH Binding Assays

For routine determinations of recoveries, a dilution assay based on the procedure described by Herrington & Veith (Endocrinology 101:984–987 [1977]) was used. In this, sequential twofold dilutions in assay buffer (50 mM Tris-HCl plus 10 mM MgCl$_2$ or CaCl$_2$ plus 0.1% bovine serum albumin plus 0.02% sodium azide pH 7.4) were made for each sample in 12×75 mm polypropylene tubes. Approximately 30,000 cpm of $^{125}$I-hGH were added per tube, either in the presence or absence of 1 μg/ml (final concentration) unlabeled hGH. Final volume per tube was 0.5 ml. Samples were normally assayed in duplicate. The tubes were incubated overnight at room temperature then the assay was terminated by adding 0.5 ml 0.1% bovine γ-globulin and 1 ml 30% (w/v) polyethylene glycol 8000 (both at 4° C. in phosphate buffered saline containing 0.02% sodium azide), mixing thoroughly and centrifuging at 4000×g (Sorval HS4 rotor, 5000 rpm) for 20 min at 4° C. The supernatants were discarded and the pellets drained inverted then γ-counted for 1 min. Specific binding was determined by subtracting the counts in the samples containing excess unlabeled hGH from the counts in the equivalent samples without unlabeled hGH. Specific binding in the 1–10% range varied linearly with receptor concentration, so recoveries were calculated for samples diluted to this range as:

$$\text{relative yield} = \frac{B_1 \cdot V_1 \cdot D_1}{B_2 \cdot V_2 \cdot D_2}$$

where B is specifically bound counts. V is the sample volume and D is the dilution factor.

For the serum binding protein, the assay was performed as above except monoclonal antibody 263 (Barnard, R. et al., Biochem. J. 231:459–468 [1985]) was included at 1/2000 final dilution during the incubation to make the hGH-binding protein complex precipitable by polyethylene glycol.

For Scatchard (Ann. N.Y. Acad. Sci. 51:660–672 [1949]) analysis, assays were performed as above except that samples were in triplicate at each unlabeled hormone concentration, the incubation time was at least 18 hrs at room temperature and unlabeled hormones were added to the assay samples over the range of 0 to 10,000 ng/ml. Using the Scatchard method, the concentration of binding sites (pM) was determined. (See for example FIG. 3a). These competition curves were analyzed with the program LIGAND (Munson, P. J., and Rodbard, D., Anal. Biochem. 107:220–239 [1980]) modified locally to run on a VAX (Digital Equipment) computer.

c) Protein Assays

Protein concentrations were measured by the Bradford, M., Anal. Biochem. 72:248–254 (1976) method using bovine serum albumin (BSA) as the standard. For samples where the protein was too dilute to detect by the Bradford et al. method and where detergent caused a high background, the samples and standard were extensively dialyzed against 1 mM HCl plus 0.1% TX100 at 4° C. to remove interference by Tris then assayed by the Fluorescamine method using a BSA standard. (Bohlen, R. et al., Arch. Biochem. Biophys. 155:213–220 [1973]). For very dilute samples, the modified fluorescamine method of Stowell et al., Anal. Biochem. 85:572–580 (1978) was used. This involved hydrolysis of the samples and standard in 2N NaOH at 100° C. for 24 hrs, partial neutralization with HCl and determination of free amino groups in the hydrolysate using the normal fluorescamine assay protocol. To reduce the dilution caused by addition of NaOH and HCl, concentrated reagents were used instead of those specified by Stowell et al. Fluorescence was measured on a Perkin-Elmer model 650-105 spectrofluorometer with excitation at 390 nm and emission at 480 nm. Hydrolysis increased the assay sensitivity approximately 7 fold over the non-hydrolyzed samples.

EXAMPLE 4

Protein Sequence Determination

Figure 5:
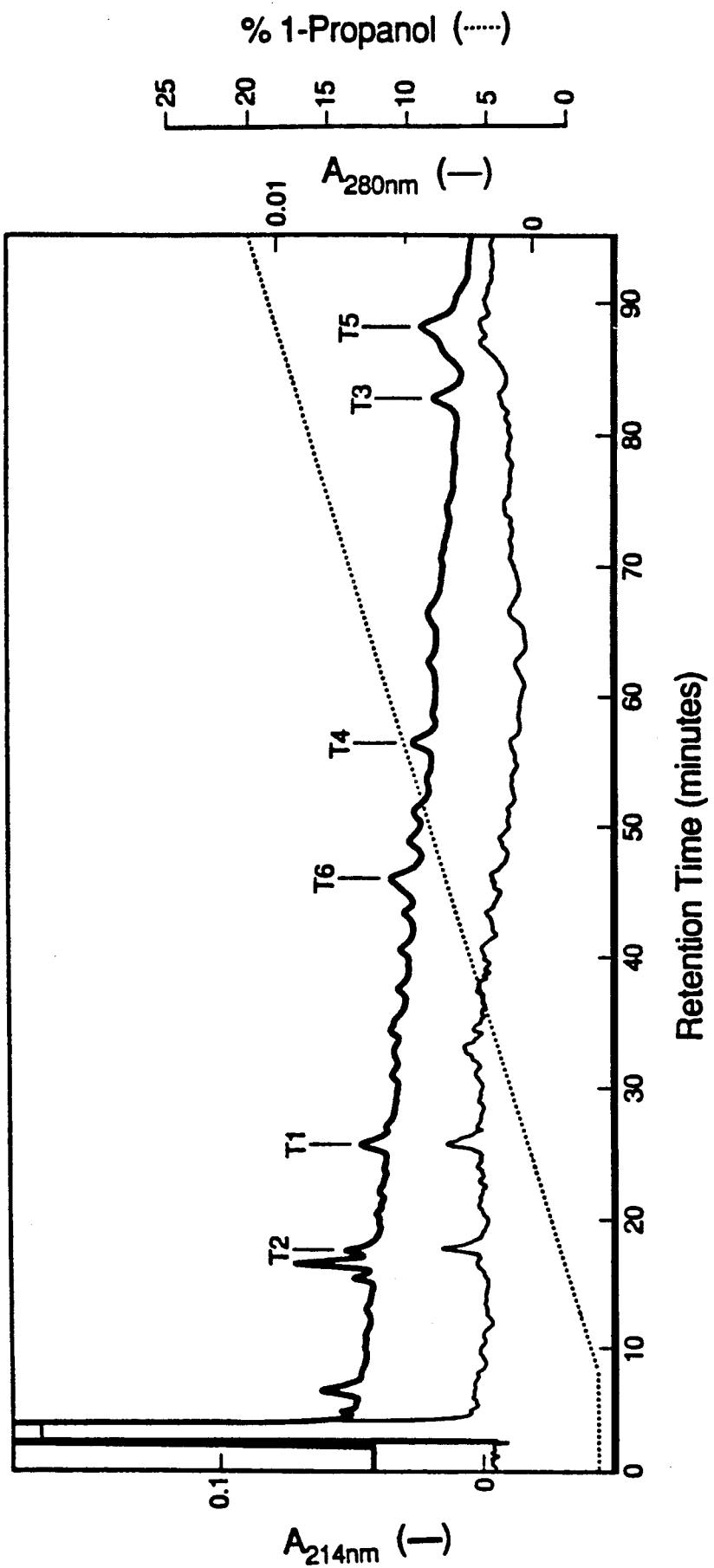
FIG. 5. Reverse phase HPLC separation of a trypsin digest of purified 130 kD liver GH receptor. Peaks T1-T6 were sequenced (see table V and text). Synchrom RP-P (C18) 4.6×100 mm column, 0.5 ml/min flow rate.

Electroeluted 130 Kd protein was digested with trypsin by dissolving the protein in 50 mM Tris-HCl pH 7.4 containing 0.1% (v/v) TX-100 and adding TPCK-trypsin dissolved in 10 mM CaCl$_2$ (0.3 mM final concentration) to 1% w/w of the 130 kD protein. The sample was incubated overnight at 37° C., then a second 1% (w/w) aliquot of TPCK-trypsin was added. After 6 hrs more at 37° C., the sample was frozen and stored at −20° C. Digestion was confirmed by SDS-PAGE. Tryptic peptides were isolated on reverse-phase HPLC using a 4.6×100 mm Synchrom RP-P C18 column. The digestion mixture was diluted with an equal volume of 50 mM Tris-HCl pH 7.6 containing 8M urea and 25 mM DTT, then injected onto the column equilibrated with 1% 1-propanol plus 0.1% trifluoroacetic acid (TFA). Peptides were eluted over 58 or 116 min with a linear 1–30% 1-propanol gradient. Flow rate was 0.5 ml/min. Peak collection was based on absorbance at 214 nm and 280 nm (FIG. 5).

Figure 6:
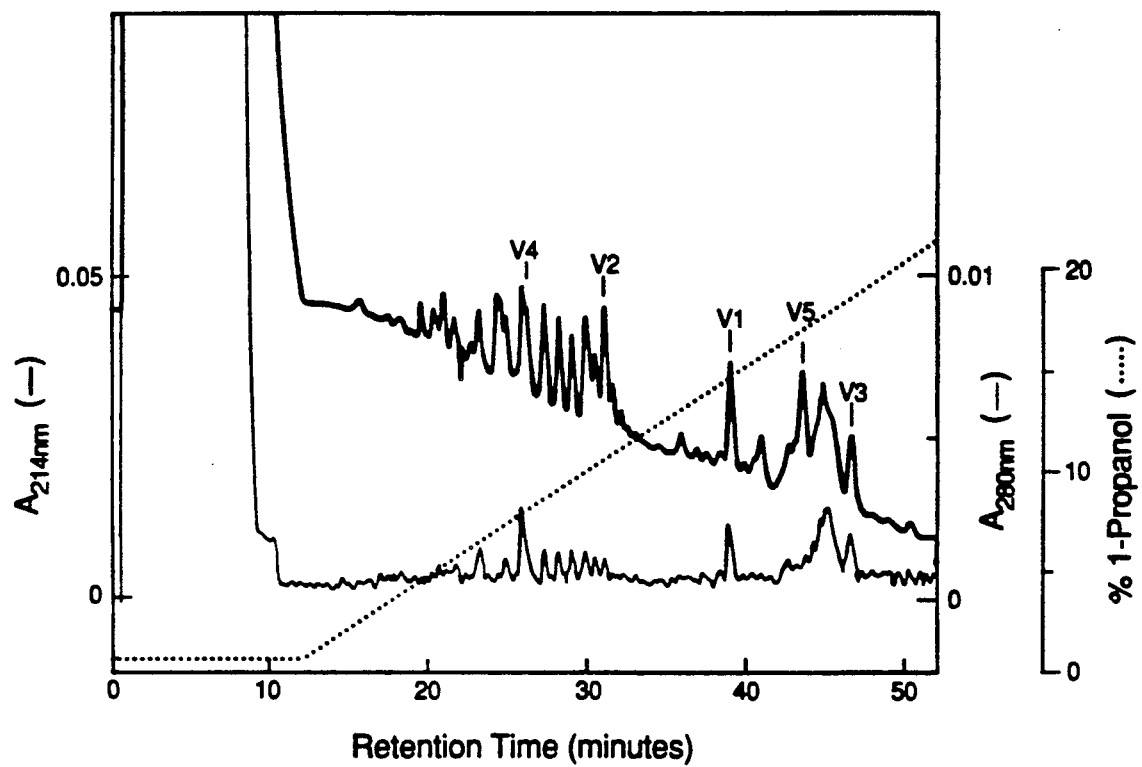
FIG. 6. Reverse phase HPLC separation of V8 digest of purified liver GH receptor. Peaks V1-V5 were sequenced (see Table V and text). Brownlee BU-300 (C4) 2.1×100 mm column; 0.5 ml/mm flow rate.

Digestion with *S. aureaus* V8 protease was performed by dissolving the electroeluted reduced and carboxymethylated 130 Kd protein in 0.1M ammonium bicarbonate pH 8.0 containing 0.1% (v/v) TX-100 and adding 2% (w/w) protease. After 3 hr at 37° C., an additional 2% (w/w) protease was added and the sample digested overnight at 37° C. Digestion was confirmed by SDS-PAGE. The sample was then dried under vacuum and redissolved in 20 mM Tris-HCl pH 8.0 containing 7M guanidine HCl and 20 mM DTT. This solution was injected onto a 2.1×100 mm Brownlee RP-300 C4 reverse-phase HPLC column equilibrated with 1% 1-propanol and 0.1% TFA, and peptides were eluted over 58 min. with a linear 1–30% 1-propanol gradient. Flow rate was 0.5 ml/min. Peaks were collected as above (FIG. 6).

Samples for amino acid sequencing were dried under vacuum and redissolved in 70% formic acid. They were then loaded into an Applied Biosystems, Inc. model 470A vapor phase sequencer and analyzed by sequential Edman degradation.

For amino acid composition determination, samples were dried in Pyrex tubes, redissolved in 6M HCl and hydrolyzed for 24 hr. at 110° C. in evacuated tubes. Samples were analyzed on a Beckman model 6300 amino acid analyzer.

a) Glycosidase Digestion

Neuraminidase digestion was performed by acetone precipitation (add 5 volumes acetone, incubate 30 min. at −20° C., centrifuge at 4° C. for 5 min, at 16,000×g, discard supernatant and vacuum dry the pellet) of an aliquot of $^{125}$I-labeled 130 Kd receptor in the presence of 200 KIU aprotinin and redissolving in 50 ml neuraminidase solution (1 U/ml in 50 mM sodium acetate pH 5.5 containing 154 mM NaCl and 4 mM $CaCl_2$). This mixture was incubated at 37° C. overnight, then the protein was acetone precipitated again and redissolved in Laemmli sample buffer containing 10 mM DTT.

N-glycanase digestion followed the protocol supplied with the enzyme. An aliquot of $^{125}$I-130 Kd receptor was precipitated as above and redissolved in 10 μl 0.5% SDS containing 0.1M 2-mercaptoethanol. This solution was heated 3 min, at 100° C., then 10.8 μl 0.55M Tris-HCl pH 8.6, 3 μl 100 mM 1,10 phenanthroline in methanol and 5 μl 7.5% NP-40 detergent were added and mixed. 0.5 μl N-glycanase (250 U/ml) was added and the sample incubated at 37° C. overnight. The protein was then acetone precipitated and redissolved in Laemmli sample buffer containing 10 mM DTT.

b) Affinity Cross-Linking

A 0.5 ml sample of affinity purified serum binding protein was dialyzed at 4° C., against 2×150 ml 25 mM HEPES buffer pH 7.6. Two 100 μl samples were diluted with 390 μl 25 mM HEPES pH 7.5 containing 10 mM $MgCl_2$ and 0.05% BSA, and 1 μl 1 mg/ml hGH was added to one sample. 10 μl $^{125}$I-hGH (395,000 cpm) were added to each tube and the samples incubated 4 hrs. at room temperature. The samples were then diluted with 0.4 ml of the same buffer, cooled on ice and 100 μl 11 mM disuccinimidyl suberate in acetone added. After 30 min. at 0° C. 10 μl 1M glycine in 25 mM HEPES pH 7.2 were added to quench the reaction. 12 μl aliquots (approximately 5000 cpm) were acetone precipitated and loaded (non-reduced) onto a 9.5% SDS gel. (Small aliquots were used to prevent overloading the gel with BSA.) The finished gel was silver stained, dried and autoradiographed at −80° C. using Kodak X-Omat AR film and an intensifier screen.

Considerable effort went into optimizing the affinity purification step. Early efforts using Affigel-10 (Bio-Rad) as the affinity support resulted in purification of less than 1000 fold and recovery of only 15–20% of the binding activity. The low apparent recovery was found to result from hGH bleeding off the column during elution. Since this condition could not be corrected by extensive washing, an alternative support glyceryl controlled-pore glass (CPG), was used in conjunction with a more stable coupling chemistry (Roy et al., supra). Tests with $^{125}$I-hGH coupled to this support showed that only minor release of the ligand occurred. Furthermore, the receptor bound more tightly when this support was used, thus allowing extensive washing with buffer and elution of impurities with 4.5M urea before elution of the receptor with 4.5M $MgCl_2$. With the Affigel column, the receptor and impurities all eluted with urea. Use of the CPG support doubled the recovery of binding and increased the receptor purity at least 10 fold.

Reduction in the column size also increased the purity, since non-specific binding was found to be proportional to the column volume. A 1 ml column was more than adequate to bind all the receptor in 4 rabbit livers or 500 ml of rabbit serum.

c) Liver Receptor Purification

The results of the rabbit liver growth hormone receptor (GHR) purification are summarized in Table I and a SDS gel of the affinity purification steps is shown in FIG. 1a. The affinity step produced a purification of 12,500 fold and resulted in receptor of about 40% purity based on the apparent reduced molecular weight of 130 kD for the major protein. This protein was found to be quite sensitive to proteases and was preserved only by keeping the preparations as cold as possible, adding liberal amounts of protease inhibitors—especially to the TX-100 extract—and working quickly. This sensitivity to proteolysis could explain previous reports of a lower molecular weight for this receptor.

On a non-reduced SDS gel, the 130 kD band disappeared-along with most of the lower molecular weight bands—and only a diffuse band at the top of the resolving gel was seen. This indicates that the extracted receptor is in a disulfide-bonded complex and that many of the lower molecular weight bands are either disulfide-bonded to the receptor or are fragments of it. It also explains why these other proteins were retained by the affinity column. When run non-reduced on a gel with a lower percentage acrylamide, this complex produced only a diffuse smear of protein with no defined molecular weight.

TABLE I

| Purification of Growth Hormone Receptor from Rabbit Liver | | | | | |
|---|---|---|---|---|---|
| Fraction | Total Protein, mg | Total High-Affinity Binding Sites, pmoles | Specific Activity pmoles/mg | Fold Purification | Yield |
| Liver Homogenate | 40,000* | — | — | — | — |
| 14,000 g Supernatant | 19,000 | 970 | 0.051 | 1 | 100% |
| 142,000 g Pellet | 4,400 | 795 | 0.18 | 3.5 | 82% |
| Affinity load | 2,500 | 595 | 0.24 | 4.7 | 62% |
| Urea eluate | 0.14 | 110 | 790 | 15,500 | 11% |
| $MgCl_2$ eluate | 0.097 | 290 | 3000 | 58,800 | 30% |

*Starting with 220 g fresh liver.

d) Growth Hormone Binding Protein Purification

Figure 2A:
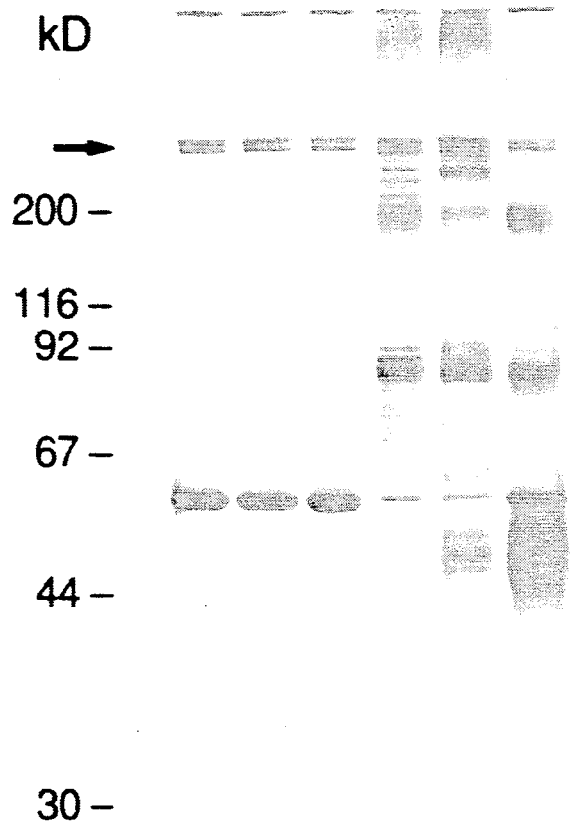
FIG. 2a. Silver-stained 9.5% SDS polyacrylamide gel (non-reduced) of the affinity purification steps and S300 pool for the serum binding protein. Approximately 1 μg total protein per lane. The arrow indicates the top of the resolving gel. Lane 1—affinity column load; lane 2—flow through; lane 3—wash; lane 4—urea eluate; lane 5—MgCl$_2$ eluate; lane 6—S300 pool.

Table II summarizes the purification of the rabbit growth hormone binding protein and FIG. 2a shows an SDS gel of the affinity column fractions and the final S300 pool. The affinity column purified the growth hormone binding protein 63,000 fold and produced material approximately 16% pure based on the apparent molecular weight (non-reduced) of 51 kD. The major contaminant appeared to be immunoglobulins and other high molecular weight proteins, many of which were removed by the S300 column. The binding activity clearly coincided with the diffuse band around 51 kD.

The urea eluate contained a larger proportion of the binding activity than was seen in the liver preparation, and was essentially equivalent to the $MgCl_2$ eluate in total binding. However, since it was considerably less pure than the $MgCl_2$ eluate, the urea eluates were saved for later repurification on the affinity column.

TABLE II

Purification of Growth Hormone Binding Protein from Rabbit Serum

| Fraction | Total Protein, mg | Total Binding Sites, pmoles | Specific Activity pmoles/mg | Fold Purification | Yield |
|---|---|---|---|---|---|
| Affinity load | 24,000* | 1200 | 0.050 | 1 | 100% |
| Urea eluate | 0.87 | 430 | 494 | 9,900 | 36% |
| MgCl₂ eluate | 0.15 | 470 | 3,130 | 63,000 | 39% |
| S300 Pool | 0.0086 | 170 | 19,800 | 396,000 | 14%** |

*Starting with 500 ml of serum.
**The yield for this step is lower in this example than normal. Usually two preparations were pooled at the MgCl₂ eluate stage and run together to reduce fixed losses.

e) Characterization of the Affinity Column Eluates—Liver Receptor

Figure 3A:
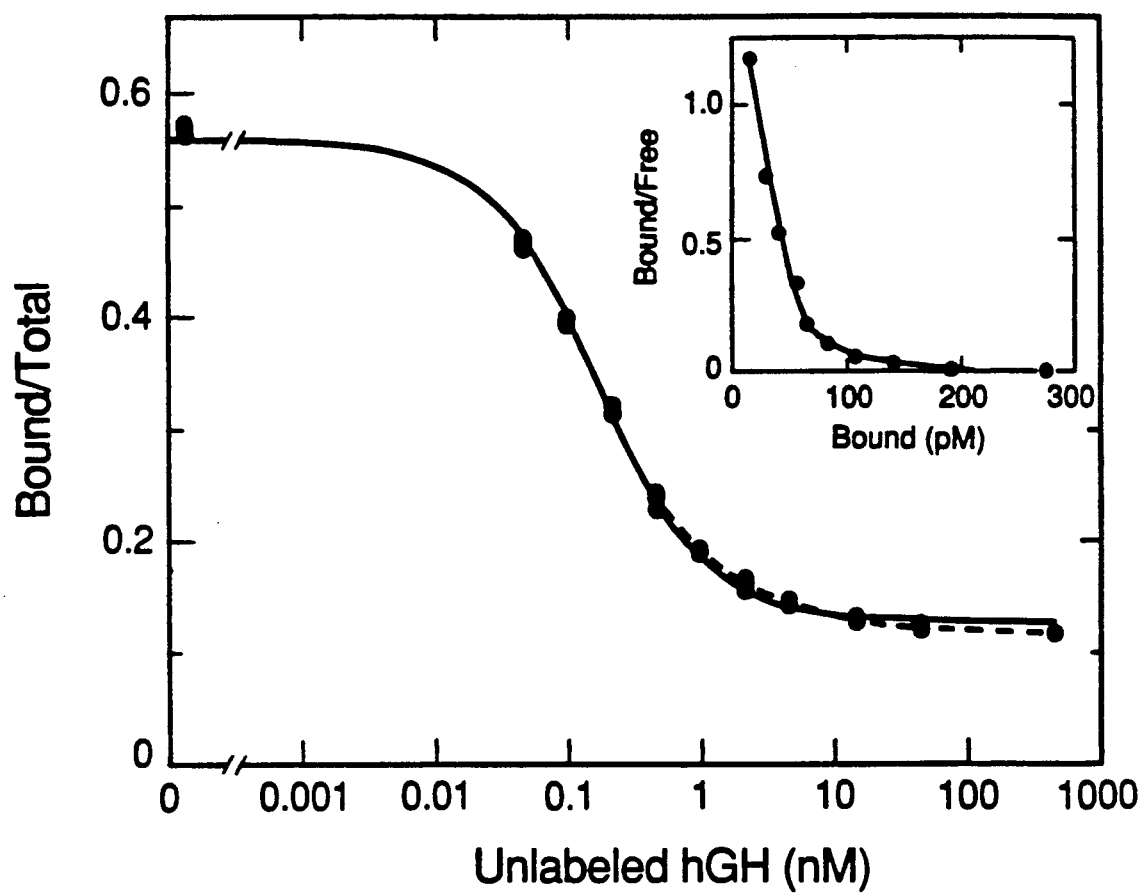
FIG. 3. (a-c). Binding competition curves and Scatchard plots (insets) for the liver GH receptor MgCl$_2$ (a) and urea (b) affinity column eluates and the serum binding protein MgCl$_2$ eluate (c). Each measurement in triplicate; 32,000 cpm $^{125}$I-hGH per tube. Single site (-) and two site (---) fits to the data are shown for the liver receptor fractions.
Figure 3B:
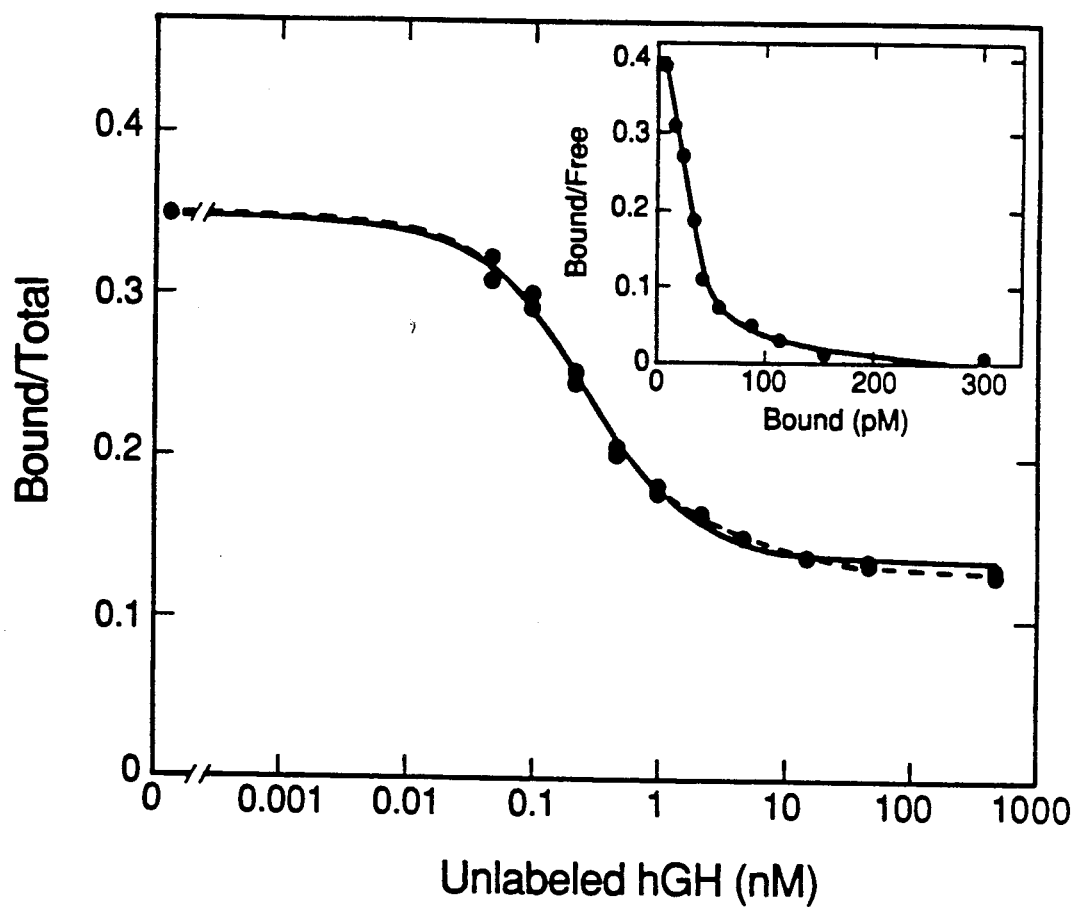
Figure 3D:
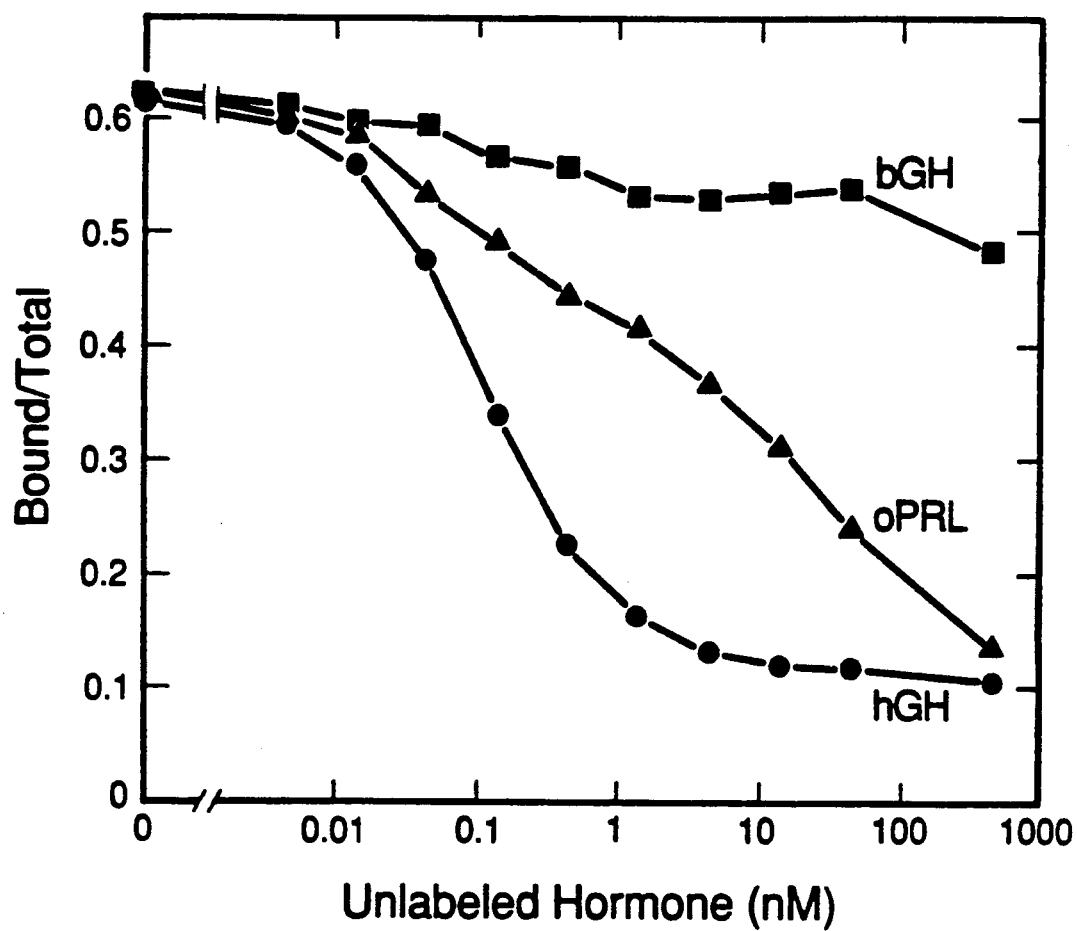
Figure 3E:
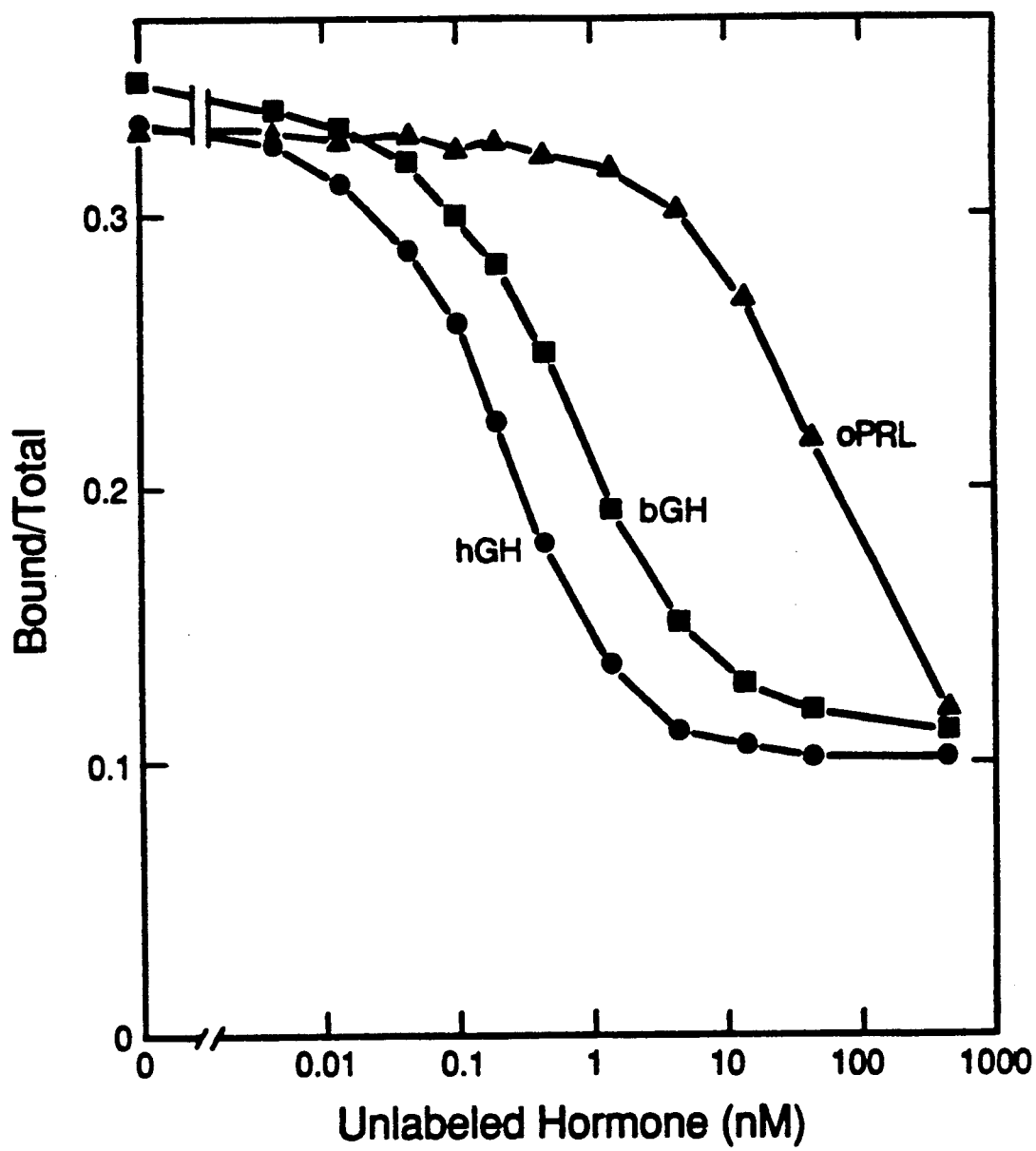

Scatchard analysis of binding competition experiments using $^{125}$I-hGH as the tracer and unlabeled hGH as the competing ligand showed a small but definite curvature when both the urea and the MgCl$_2$ eluates were tested (FIG. 3a, b). Using a two-site model, association constants for the high-affinity sites were $K_A = 9.8 \times 10^9 M^{-1}$ for the urea eluate and $28 \times 10^9 M^{-1}$ for the MgCl$_2$ eluate. The association constant for the urea eluate was consistently lower than for the MgCl$_2$ eluate. For the lower-affinity sites, $K_A \sim 10^8 M^{-1}$ for both. Since the effect of these sites is small, the value of the association constant is poorly determined.

Competition experiments using $^{125}$I-hGH as the tracer and human GH (hGH), bovine GH (bGH) or ovine prolactin (O-PRL) showed clear differences between the urea and MgCl$_2$ eluates. For the urea eluate, $^{125}$I-hGH was displaced somewhat less well by bGH than hGH and poorly by O-PRL. This is characteristic of the so-called somatogenic receptor in rabbit liver.

For the MgCl$_2$ eluate, the results (FIG. 3d) were surprising in that bGH displaced about 20% of the tracer at a low concentration but could not displace the remainder even at very high concentrations (1 μg/ml). The extent of competition by bGH varied from 15–70% depending on the receptor concentration and assay incubation time. O-PRL could fully displace the tracer at high concentrations but was about 40 fold less effective than hGH. The shape of the O-PRL displacement curve also indicated that more than a single class of binding site was involved. These results suggest that the MgCl$_2$ eluate contains at least two classes of hGH binding site, one displaceable by bGH and one not. Since neither was readily displaced by O-PRL, they do not seem to represent classical lactogenic receptor. Both eluates contained a major protein at 130 kD, so this was the most likely candidate for the protein containing the hGH binding site.

f) Characterization of the Liver Receptor

The 130 kD protein was only observed upon reduction of the purified receptor and separation on a denaturing gel system. Since this treatment abolished binding activity, it was necessary to establish the relationship between the 130 kD protein and the binding activity by indirect means.

Several anti-receptor monoclonal antibodies (Barnard, R. et al., Biochem. J., 231:459–468 [1985]) were tried against the denatured receptor but only MAb 5 gave a strong response FIG. 1b shows an immunoblot of the MgCl$_2$ eluate with MAb 5. Fresh liver shows binding predominantly to the 130 kD protein as well as to two sharp bands at around 100 kD. Longer development showed weak binding to several lower molecular weight bands as well. A monoclonal antibody of the same class directed to an unrelated protein (tissue plasminogen activator) showed no response. Lane 1 is the same as lane 2 except starting with frozen liver obtained commercially; substantial degradation is apparent in this material.

Immunoblotting with inhibitory antibodies 263 and 7 gave a weak response. Immunoprecipitation with MAb 263 precipitated the 130 kD protein along with many of the smaller proteins, again showing these proteins are associated. Similarly, affinity cross-linking produced a strong radioactive band at the top of the gel similar to that seen on a non-reduced gel. This is probably due to cross-linking of the disulfide-bonded proteins, making reduction ineffective at dissociating them.

In a hormone blot with SDS-solubilized rabbit liver membranes Haeuptle et al., J. Biol. Chem. 258:305–314 (1983) showed specific binding of $^{125}$I-hGH to a band in the 50–67 kD region and another in the 130–140 kD region range. Our results were similar when degraded affinity purified material was used in that the main binding activity was seen at around 50 kD. For crude membrane extracts, considerable specific binding above 100 kD was also seen but a high diffuse background (displaceable by hGH) made it difficult to distinguish individual bands. Affinity purified receptor showed specific binding mainly at the top of the gel when run non-reduced; this activity was destroyed upon reduction.

g) Glycosidase Digestion

Digestion of $^{125}$I-labeled 130 kD receptor with N-glycanase and neuraminidase indicated the presence of N-linked carbohydrate with some terminal sialic acid. Neuraminidase alone reduced the 130 kD protein to a sharp band at about 116 kD on reduced SDS gels while N-glycanase produced a diffuse band between 90–100 kD. Combined digestion was similar to N-glycanase alone. No effort was made to demonstrate the presence of O-linked sugars.

Characterization of Affinity Column Eluates—Growth Hormone Binding Protein

Scatchard analysis of the urea and MgCl$_2$ eluates from the affinity column (FIG. 3c) using $^{125}$I-hGH as the tracer and unlabeled hGH as the displacing ligand showed a single class of binding site in both. The association constants were within experimental error ($K_A = 5.5 \times 10^9 M^{-1}$ for urea and $5.7 \times 10^9 M^{-1}$ for MgCl$_2$), so it is possible the high percentage of binding which elutes with urea (compared to the membrane receptor) is due to the lower binding affinity of the binding protein for hGH and not to subpopulations of binding proteins with different binding affinities. For the MgCl$_2$ eluate, displacement of $^{125}$I-hGH by bGH and O-PRL (FIG. 3f) showed the characteristics expected for a somatogenic receptor, i.e., bGH was approximately 6 fold less effective than hGH and O-PRL was approximately 170 fold less effective than hGH.

Characterization of Growth Hormone Binding Protein

The apparent molecular weight of the binding protein on Sephacryl S300 (FIG. 4) is 96 kD. Since the apparent molecular weight on non-reducing SDS gels is around 51 kD, the protein may form a non-covalent dimer at the concentrations used on the S300 column.

Figure 2B:
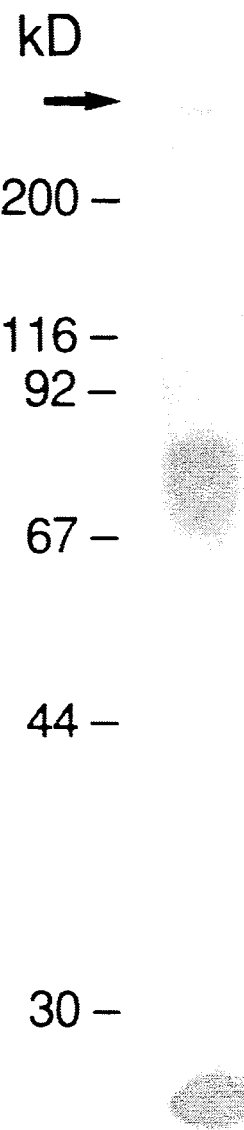
FIG. 2b. Autoradiogram of a 9.5% SDS polyacrylamide gel of $^{125}$I-hGH cross linked to the serum binding protein with disuccinimidyl suberate in the absence (−) or presence (+) of 1 μg/ml unlabeled hGH The complex at 75 kD comprises the 51 kD serum binding protein and hGH of 22 kD for hGH.

Affinity cross-linking of $^{125}$I-hGH to the binding protein using disuccinimidyl suberate produced a single diffuse band on a non-reducing SDS-gel (FIG. 2b) with an apparent molecular weight of 75 kD. Subtracting 22 kD for hGH gives 53 kD for the binding protein. No other specific binding was found in serum.

The cross-linking and gel filtration results indicate that the diffuse band at 51 kD on non-reducing SDS gels is the serum binding protein. This was confirmed by electroeluting SDS gel slices containing this band and the surrounding region and testing the eluates for binding activity. Substantial activity (representing at least 10% of the load) was recovered only from the 51 kD band.

Digestion with N-glycanase confirmed the presence of N-linked sugars on the 51 kD protein. The digest reduced the 51 kD protein to several bands in the 40-49 kD range. These may represent incomplete deglycosylation or partially degraded forms of the binding protein.

h) Sequence and Composition—Membrane Receptor

Composition results for electroeluted reduced and carboxymethylated 130 kD receptor are shown in Table III. The number of each amino acid assuming a total molecular weight of 72 kD is shown in Table III. Computation of the best fit of integral residue values to the data gave an estimated molecular weight of 72 kD, with a second minimum at 116 kD. The glycosidase data indicate the protein molecular weight is below 100 kD, so the lower molecular weight estimate is the more probable value.

TABLE III

| 0 | | Estimated Total Number of Each Amino Acid |
|---|---|---|
| 1 | Asp | 68.89 |
| 2 | Thr | 37.43 |
| 3 | Ser | 56.20 |
| 4 | Glu | 90.13 |
| 5 | Pro | 48.28 |
| 6 | Gly | 44.39 |
| 7 | Ala | 45.06 |
| 8 | Cys | 18.25 |
| 9 | Val | 42.82 |
| 10 | Met | 9.94 |
| 11 | Ile | 24.38 |
| 12 | Leu | 64.49 |
| 13 | Tyr | 20.77 |
| 14 | Phe | 27.01 |
| 15 | His | 13.04 |
| 16 | Lys | 39.35 |
| 17 | Arg | 24.49 |
| 18 | Asn | — |
| 19 | Gln | — |
| 20 | Trp | — |
| 21 | total | 674.92 | i) N-Terminal Sequence

The N-terminal sequence for the 130 kD receptor was determined three times, twice on electroeluted 130 kD receptor (carboxymethylated and not) and once on the complete MgCl$_2$ eluate from the affinity column. In all three cases, two sequences were obtained (Table IV) with a low level of other residues present in the less purified sample. The minor sequence (sequence 2 in Table IV) was ubiquitin (Schlesinger, D.H. et al., Biochemistry 14:2214-2218 [1975]), a protein which has been found attached to other cell-surface proteins (Siegelman, M. et al., Science 231:923-829 [1986]; Yarden, Y. et al., Nature 323: 226-232 [1986]) but whose function there is unknown. The abundance of ubiquitin was variable, but from the sequencing yields appeared to be 20-50% the level of the major sequence.

TABLE IV

| Amino Terminal Sequence For Liver Receptor | |
|---|---|
| 1) F—S—G—S—E—A—X—P—A—T—L—G—R—A—S—E (positions 5, 10, 15) | initial yield = 23 pmoles |
| 2) M—Q—I—F—V—K—T—L—T—G—K—X—I (positions 5, 10) | initial yield = 10 pmoles |

The major sequence comprising 16 amino acids did not correspond to any previously known protein. Residue 7 was not identified initially but was later found from the cDNA sequence to be Thr. Ubiquitin also has a Thr-7 but the recovery on this cycle seemed too low to represent the sum from both proteins. This may indicate that Thr-7 on the receptor is modified.

TABLE V

| Tryptic and V8 Peptides from 130 kD Liver GH Receptor | | | |
|---|---|---|---|
| | | Approximate Initial Yield | Sequence Position |
| Trypsin Peptides | | | |
| T2: | ($^I_E$)V K E($^Y_T$)($^E_Q$)V K mixture sequence[1] | | |
| T2.1: | L D K E Y E V R | 27 pmoles | 204–211 |
| T2.2: | E V N E T Q W K | 41 pmoles | 180–187 |
| T3: | ($^S_D$)[2]G T A E D A P G S E M P V P D Y | 10 pmoles | 561–577 |
| T4: | V E P S F N Q E D I Y I T T E S L T T[T][3](A)(E) | 25 pmoles | 538–559 |
| T5: | [C]F[S]V E E I V Q (P) | 12 pmoles | 122–131 |
| T6.1: | S P G S V($^Q_E$)($^L_D$)($^F_I$)Y I R | 30 pmoles | 60–70 |
| T6.2: | T(S)(C)($^Y_E$)($^E_A$)(P)($^D_L$)($^I_F$)[L]($^E_L$)N D F N A[S]D | 10 pmoles | 369–385 |
| V8 Peptides | | | |
| V3: | [W]K[E][C]P(D)(Y)V[S](A)(G)(E)(N)[S][C](Y)F | — pmoles | 80–96 |
| V5.1: | (S)T L Q A A P S Q L S N P N S L A N I D F Y | 10 pmoles | 448–469 |

TABLE V-continued

Tryptic and V8 Peptides from 130 kD Liver GH Receptor

| | | Approximate Initial Yield | Sequence Position |
|---|---|---|---|
| V5.2: | (F)I E L D I D D | 5 pmoles | 327–334 |

[1]Mixture was finally resolved from the cDNA sequence. The absence of Asn on Cycle 3 may indicate carbohydrate is attached at this position in T2.2.
[2]Parentheses indicate uncertainty in the sequencing data. Where two residues are shown, the one found in the cDNA sequence is on top.
[3]Brackets indicate residues not called or incorrectly called. The residue indicated is from the cDNA sequence.

j) Tryptic Peptides

The reverse-phase HPLC chromatogram (FIG. 5) produced unusually broad peaks. The reason for this is unclear, since another protein digested under the same conditions ran normally. Contaminants in the TX-100 also produced interfering peaks in the region of interest but these could be excluded by comparison to a blank run.

Six peptides (T2–T6.2, Table V) were analyzed for amino acid sequence. T1 gave no usable sequence and T2 and T6 were mixtures. Where the protein sequence was ambiguous or incorrect, the correct residue from the cDNA sequence is shown.

T2 contained two major peptides plus minor contaminants. T2.1 is unusual in that it contains a Lys residue. Apparently the flanking acid groups were able to retard tryptic cleavage at this site. T2.2 contains a potential N-linked glycosylation site. Since Asn was not seen on cycle 3 despite strong signals for the flanking residues, it is likely that this Asn is glycosylated.

k) V8 Peptides

The reverse-phase HPLC chromatogram for the V8 digest is shown in FIG. 6. Once again contaminants in the TX-100 produced interfering peaks. Amino acid sequencing was performed on five peptides (V1–V5). only two of which gave usable sequence (Table V).

Conditions of the digestion favored cleavage only at Glu residues. Other factors apparently restricted cleavage to a subset of the available sites since both V3 and V5.2 contained internal Glu residues.

k) N-Terminal Sequence, Growth Hormone Binding Protein

The gel electroeluted 51 kD serum binding protein produced one major and two minor sequences upon amino acid sequence analysis (Table VI). The major sequence clearly corresponded to the N-terminal sequence of the membrane bound receptor. By subtracting this known sequence and comparing the remaining residues to the cDNA sequence for the receptor, those sequences represented trypsin-like cleavages at Arg 13 and 20. Because of this, it was possible to confirm the sequence identity between the serum and membrane bound forms out to residue 37, with only occasional gaps caused mainly by the high background (especially glycine) on the early cycles. Ubiquitin was not observed in this preparation.

TABLE VI

Amino-terminal Sequences for the Liver Receptor and Serum Binding Protein

| | | | | | 5 | | | | | 10 | | | | | 15 | | | | 20 | | | |
|---|---|---|---|---|---|---|---|---|---|---|---|---|---|---|---|---|---|---|---|---|---|---|
| GHR: | F | S | G | S | E | A | [T] | P | A | T | L | G | R | A | S | E | [S | V | Q | R | V | H | P |
| SBP1: | X[2] | X | X | S | E | A | T | P | A | T | L | G | R | A | S | E | S | V | Q | X | V | H | P |
| SBP2: | — | — | — | — | — | — | — | — | — | — | — | — | X | X | E | (S)[3] | V | Q | R | V | H | P |
| SBP3: | — | — | — | — | — | — | — | — | — | — | — | — | — | — | — | — | — | — | — | X | X | P |
| | | 25 | | | | 30 | | | | | 35 | | | | | | | | | | | | |
| GHR: | G | L | G | T | N | S | S | G | K | P | K | F | T | K] | | | | | | | | | |
| SBP2: | G | X | X | T | X[4] | S | S | G | K | P | K | F | T | | | | | | | | | | |
| SPB3: | X | L | X | T | X[4] | S | S | G | K | P | K | F | X | K | | | | | | | | | |

[1]Residues in [ ] were determined from the cDNA sequence.
[2]X represents residues which could not be called. A high glycine background obscured this residue on the first several cycles.
[3]( ) represents residues whose presence was uncertain.
[4]The absence of Asn could indicate N-linked carbohydrate at this position.

The filter used for N-terminal sequencing was removed and the residual protein digested with cyanogen bromide, then sequenced again. Comparison of this mixture sequence with the cDNA sequence of the 130 kD receptor confirmed the presence of peptides starting at Met-117 and Met-189. The peptide starting at Met-236 may also have been present but it was more difficult to detect. No other CNBr peptides were found, suggesting that the sequence extends no farther than the transmembrane domain. Efforts are underway to determine the C-terminal residue. These are complicated by the relatively small amount of protein available and the lack of suitable chemical methods to perform C-terminal digestions at the picomole level.

EXAMPLE 5

Isolation of Growth Hormone Receptor Clones

Three approaches were undertaken to isolate clones of the growth hormone receptor. Prior to obtaining highly purified protein, monoclonal antibodies (Barnard et al., supra) to the rabbit liver receptor were used to screen both L-cells transfected with genomic rabbit DNA as well as rabbit liver cDNA clones in a λgt11 vector. No receptor clones were isolated by either of these two approaches.

Figure 7:
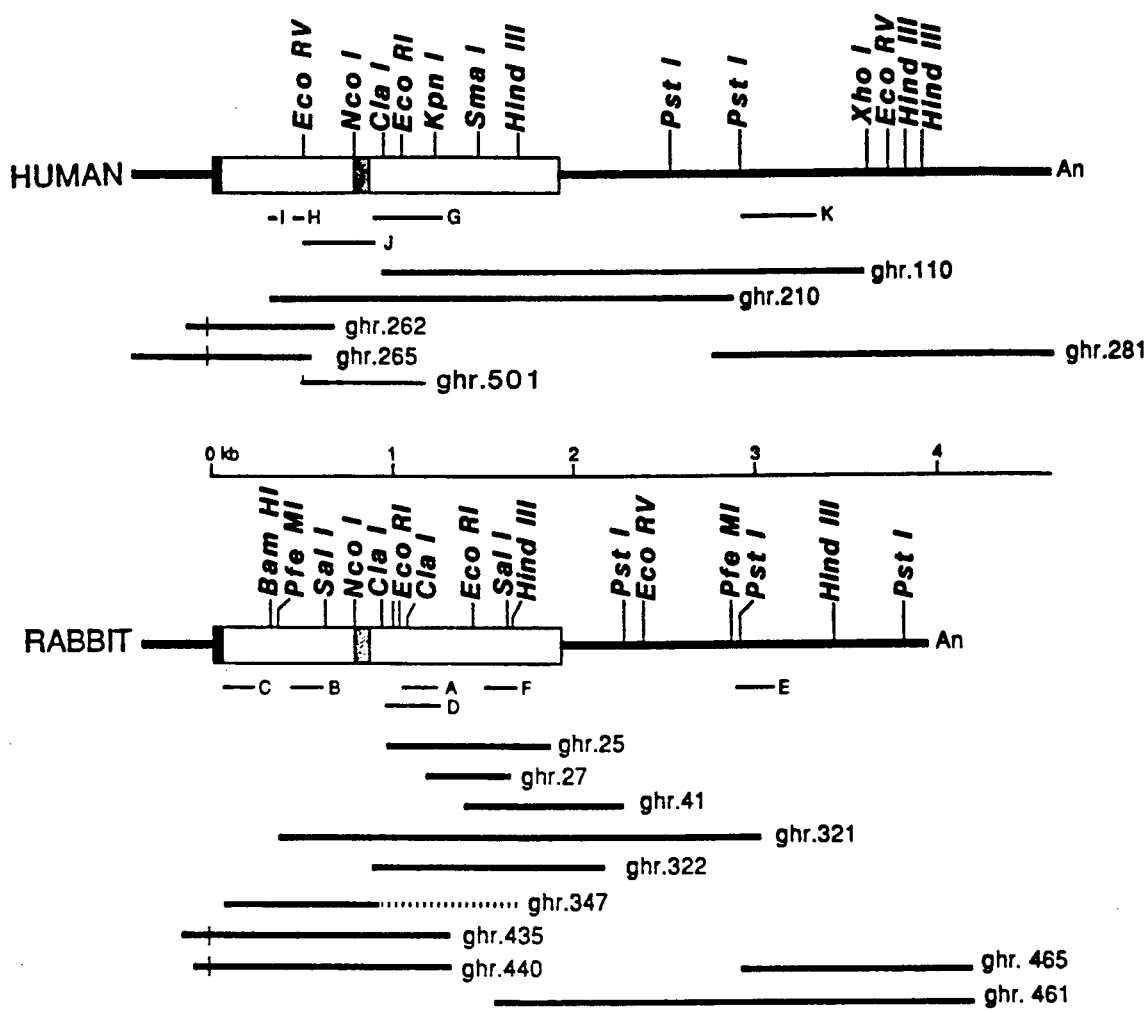
FIG. 7. Maps of the cloned cDNA's for the human and rabbit growth hormone receptors. The open box is the coding region of the mRNA. The filled part of the box is the signal sequence; the stippled part is the transmembrane domain. The regions lettered A.K are probes and oligonucleotide primers used in the cDNA cloning described below. The individual cDNA clones are labelled ghr.25-465. As noted in the text, the clones diverge 5' of the bar show on clones ghr.262, 265, 435, and 440. The 3' divergence of clone ghr.347 is noted by the dotted line.

Growth hormone receptor clones were isolated by screening a rabbit liver cDNA library with an oligonucleotide probe based on protein sequence data. A single-sequence, 57-mer probe based on the 19 residue amino acid sequence of a tryptic fragment of the receptor was used to screen rabbit liver cDNA clones in a λgt10 vector. From a screen of $1.0 \times 10^5$ oligo-dT and $1.0 \times 10^5$ random primed clones, 2 and 27 positive clones were identified. A number of these clones were mapped and sequenced (FIG. 7, ghr.25, ghr.27, and ghr.41). The translated DNA sequence matched exactly the amino acid sequence of the tryptic fragment used for the probe, and the probe contained a match with the cloned DNA sequence of two 14 base regions separated by a single mismatch. The tryptic fragment is located near the C-terminal end of the protein starting at amino acid 538 (FIG. 8). Clones of the entire coding and 3' untranslated regions were isolated by rescreening the same libraries with fragment probes starting from the initial set of clones.

Human growth hormone receptor clones were isolated by screening a human liver cDNA library with a restriction fragment probe from one of the first rabbit clones isolated (ghr.27). Overlapping clones of the entire human coding and 3' untranslated regions were isolated from oligo dT, random, and specifically primed liver cDNA libraries. FIG. 7 shows the map of a selected number of both the rabbit and human cDNA clones. The complete DNA and translated protein sequences of both cDNA's is shown in FIG. 8.

Hybridizations were performed in 20% formamide, 5×SSC, 50 mM sodium phosphate (pH 7), 40 μg/ml sonicated salmon testis DNA. 5×Denhardt 20% dextran sulfate overnight at 42° C., and washed in 1×SSC at 42° C., except as noted below. Fragment probes were $^{32}$P-labelled by primed synthesis (Feinberg, A. P., Vogelstein, B., Analyt. Biochem. 132:6–13 [1983]); oligonucleotide probes were $^{32}$P end-labelled.

Poly A+ rabbit liver RNA was prepared from a male New Zealand white rabbit by the LiCl precipitation method (Cathala, G. et al., DNA 2:329–335 [1983]) followed by oligo-dT cellulose chromatography (Maniatis, T. et al., Molecular Cloning [1982]). Two hundred eighty-two micrograms of poly A+ RNA were obtained from 6 grams of liver. Oligo-dT and random primed cDNA's were prepared from 2 μg of poly A+ rabbit RNA with reagents from Amersham Inc. These cDNA preparations were cloned with a λgt10 vector (Huynh, T. V. et al., in DNA Cloning, Vol. I, Glover, D. M. (ed.) Oxford, IRL Press [1985]) and hemikinased linkers as described (Wood, W. et al., Nature 312:330–337 [1984]). From 20 ng of oligo-dT and 10 ng of random-primed linked cDNA, $2 \times 10^6$ and $1 \times 10^6$ primary clones were obtained and amplified.

These two libraries were screened with the probe ghr.3, 5'-GTGGAGCCATCCTTCAACCAGGAG-GACATCTACATCACCACAGAGTCCCTGAC-CACC, a 57 base synthetic oligonucleotide based on the 19 amino acid tryptic fragment T4 of the receptor. Hybridizations were performed as above with 20% formamide and washed in 1×SSC at 42° C. Clones ghr.25, ghr.27, and ghr.41 were isolated from the random-primed library.

The oligo-dT (760,000 clones) and random (800,000 clones) rabbit libraries were rescreened with a 5'-restriction fragment from ghr.25 (probe A). Eight positive oligo-dT and 100–300 random primed positive clones were identified. Clone ghr.321 from the oligo-dT library was completely sequenced. The same plating of the oligo-dT primed library was rescreened with a 5'-restriction fragment from ghr.321 (probe B). Seven positive clones were identified of which ghr.347 is shown.

To facilitate isolation of long clones including the 5'-end of the gene and to take advantage of the high frequency of positive clones in the random-primed rabbit library, the longer inserts from this library were isolated and recloned. The library was grown as a pool of phage, the cDNA inserts cut out with Xho (a site in the cloning linker), and the long inserts (greater than 1.5 kbp) isolated from an acrylamide gel. These fragments were recloned in λgt10 with XhoI to EcoRI linkers. $2 \times 10^6$ primary clones were obtained for this library. (The representation of this library is difficult to assess due to the pooled growth of the library to obtain DNA.) One million one hundred thousand clones from this library were screened both with probe B (above) and with a 5' restriction fragment from ghr.347 (probe C). Clones positive with both probes were identified of which ghr.435, and ghr.440 are shown.

To obtain clones of the rabbit 3' untranslated region. 200,000 oligo-dT primed rabbit cDNA clones were screened with a restriction fragment from ghr.321 (probe E). The hybridization was performed in 50% formamide and the filters washed in 0.2×SSC at 60° C. Fifteen positive clones were obtained. DNA from seven of these was denatured, spotted on nitrocellulose and hybridized to a dT$_{40}$ oligonucleotide probe to isolate clones with a terminal poly A sequence. The hybridization was in 20% formamide and the blots were washed in 3.0M tetramethylammonium chloride at 65° C. Three of the 7 clones were positive and two (ghr.46 and 465) are shown.

The initial human growth hormone receptor clones were isolated from an adult liver cDNA library. This library contained oligo-dT primed clones in a λgt10 vector. One million cDNA clones were screened with a restriction fragment from the rabbit clone (ghr.27, probe D). The hybridization was performed in 20% formamide and the filters washed in 1×SSC at 42° C. Twenty-eight positive clones were identified of which clone ghr.110 is shown. The same plating of the oligo-dT primed library was rescreened with a 5'-primed restriction fragment from ghr.110 (probe G). Twelve additional positive clones were identified of which λghr.210 is shown.

To isolate clones containing the 5' end of the human receptor, two additional cDNA libraries were constructed from adult human liver mRNA as described above. One library was randomly primed, the other specifically primed with the 15-mer ghr.5 (5'ATTGCGTGGTGCTTC, primer H). One million, one hundred thousand primary clones from the random library and 360,000 primary clones from the specifically primed library were screened with two probes. One probe, the 27-mer ghr.6 5'CATTGCTAGTTAGCTT-GATACAATAAG (probe I) was hybridized in a 20% formamide and washed in 3.0M tetramethylammonium chloride (Wood, W. I. et al. PNAS [USA] 82:1585–1588 [1985]). The other probe (probe C, above was hybridized in 20% formamide and washed in 1×SSC at 42° C. Two positives were found from the random library and nine from the specifically primed library. Clones ghr.262 (from the random library) and ghr.265 (from the specifically primed library) are shown.

To obtain a second clone for the human cDNA region between clone ghr.110 and ghr.262, one million clones from the random-primed human cDNA library were screened with a restriction fragment from ghr.210 (probe T). The hybridization was in 50% formamide and the filters were washed in 0.2×SSC at 60° C. Four positive clones were obtained and one (ghr.501) was characterized by sequencing the DNA insert.

To obtain clones of the human 3' untranslated region, 200,000 oligo-dT primed library clones were screened with a restriction fragment from ghr.110 (probe K). The hybridization was performed in 50% formamide and the filters washed in 0.2×SSC at 60° C. Eleven positive clones were obtained and one (ghr.501) of the three of these tested positive with an oligo-dT probe (as described above for the rabbit 3' end clones).

Two independent clones have been isolated for all the coding and for much of the untranslated regions of both the rabbit and human cDNA's. The DNA sequence of these pairs of clones match with the exception of a few simple base differences and some considerable divergence in the 5' untranslated region (noted in Table VII below). Only two of the differences affect an amino acid. In the human receptor a G to T difference in ghr.501 changes serine 357 to an isoleucine, and in the rabbit receptor an A to G difference in ghr.440 changes alanine (−8) to a threonine. Both are conservative substitutions.

TABLE VII

Single Base Pair Differences in the Growth Hormone Receptor cDNA Clones

| Location (bp) | Change | Comments |
|---|---|---|
| HUMAN | | |
| 558 | A in ghr.210, G in ghr.262 and .501 | No amino acid change |
| 1124 | G in ghr.210 and .110, T in ghr.501 | Ser in ghr.210 and .110, Ile in ghr.501 |
| 2436 | C in ghr.210, T in ghr.110 | In 3' untranslated |
| RABBIT | | |
| 31 | G in ghr.435, A in ghr.440 | Ala in ghr.435 Thr in ghr.440 |
| 2066 | G in ghr.321, A in ghr.322 | In 3' untranslated |
| 2102 | T in ghr.321 and 322, C in ghr.41 | In 3' untranslated |
| 3878 | G in ghr.465, GG in ghr.461 | At poly A site |

DNA sequences beyond eleven base pairs 5' of the putative initiating ATG diverge completely in most of the clones isolated. Of the six human and three rabbit cDNA clones that include this 5' region, only two pairs are similar. The two human clones shown in FIG. 7 (ghr.262 and ghr.265) are identical in this 5' region, and one rabbit clone (ghr.435) and one human clone (ghr.244, not shown) are about 80% homologous. The remaining five clones are unique. Probably these clones are due to multiple differentially spliced RNA's at the 5' end of both these genes. The observation that clones from two different species isolated from a number of different cDNA libraries diverge at the same point suggests that this is not some unusual cloning artifact. Whether these differentially spliced clones are biologically significant will await further experimentation.

Two independent rabbit clones diverge from the others 3' of bp 877 (one, ghr.347, is shown in FIG. 7). The divergent sequence of these two clones matches identically. The translated amino acid sequence of these two clones diverge from the others beginning 4 residues C-terminal of the putative transmembrane domain (see below), followed by four new amino acids before encountering a stop codon. Thus, these two clones would encode a protein containing the extracellular growth hormone binding domain, the transmembrane domain, and a truncated cytoplasmic domain of only 8 residues.

Figure 9:
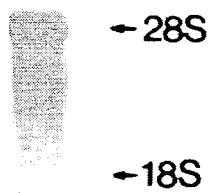

Two of the rabbit (ghr.461 and 465) and one human cDNA clone (ghr.281) contain poly A+ tracts at the 3' ends. These are preceded by AATAAA (human) and CATAAA (rabbit) poly A+ addition signals. Blot hybridization of poly A+ rabbit liver RNA with a full-length rabbit probe shows one main hybridizing band of ~4700 bp approximately the size of the cloned cDNA (FIG. 9).

Figure 10:
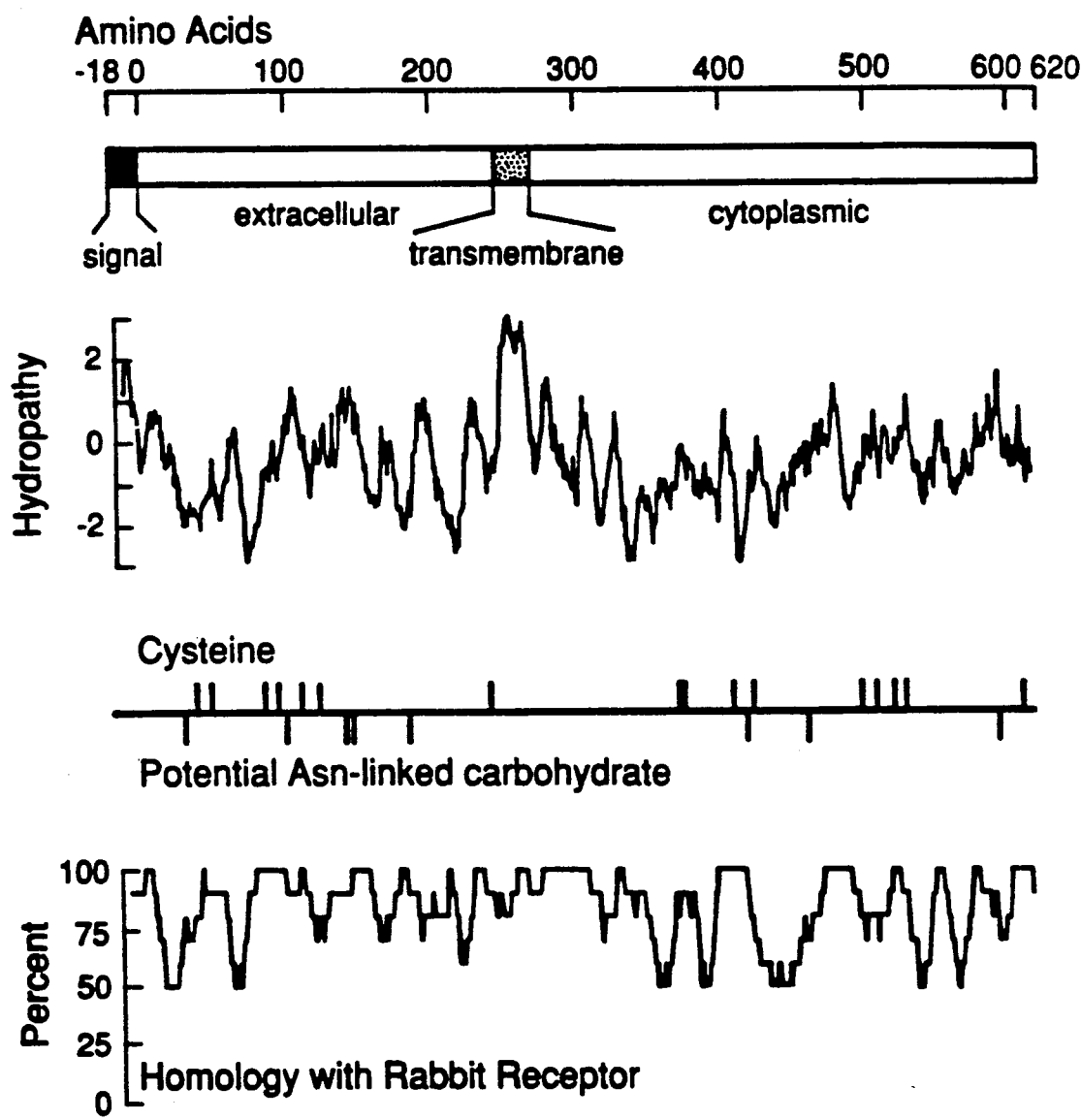

Both the rabbit and human receptor clones contain an open reading frame of 638 amino acids. All of the 10N-terminal, tryptic, and V8 peptide sequences determined for the purified rabbit receptor are present in this translated sequence (see Tables IV and V). The amino acid sequence found for the N-terminal of the rabbit receptor is preceded by 18 amino acids beginning with a methionine. The DNA sequence surrounding the ATG encoding this methionine matches the consensus sequence expected for a translation initiation site. The following 18 amino acids contain a hydrophobic core flanked by charged residues indicative of a membrane signal sequence. Thus the mature form of the receptor would be expected to be 620 amino acids with a translated molecular weight of 70 kD. This is somewhat smaller than the 130 kD molecular weight determined by SDS gel analysis for the purified rabbit liver receptor even accounting for covalently attached ubiquitin (~9 kD). Since a number of cDNA clones for both the human and rabbit receptor have been isolated, the apparent discrepancy in molecular weight is probably due to glycosylation or an SDS gel artifact or both. A hydropathy plot of the human sequence (FIG. 10) shows only a single major hydrophobic region of about 24 residues centrally located in the molecule. This hydrophobic region is expected to be a transmembrane domain which separates the extracellular, N-terminal, growth hormone binding domain from the intracellular, C-terminal, signaling domain. The potential N-linked glycosylation sites (Asn-X-[Ser/Thr]) as well as the location of the cysteine residues are also shown in FIG. 10. There are no obvious regions with a high serine or threonine content often indicative of O-linked glycosylation.

The rabbit and human protein sequences are highly homologous throughout with 84% identity overall (FIGS. 8 and 10). The two sequences can be aligned without any insertions or deletions. The homology extends throughout the molecules including even the transmembrane domain. Computer assisted searches for homology to other known proteins in several data bases has shown no clear homology to any other proteins. The receptor contains no internally repeated domains and no particularly cysteine rich regions in the extracellular domain as has been found with some other receptors (FIG. 10). The seven extracellular cysteines are conserved between the human and rabbit sequences. There are seven conserved and three non-conserved cysteines in the intracellular domain.

The soluble growth hormone binding protein found in rabbit serum has the same N-terminal amino acid sequence as the receptor. There are two potential sites for trypsin-like proteolytic cleavage of the rabbit receptor that could release the extracellular growth hormone binding domain in a soluble form. One site is the alternating arginine, neutral amino acid sequence found starting at arginine 211. The other is at arginine 246 which immediately precedes the transmembrane domain. While the human sequence lacks this second site, some type of proteolytic cleavage before the transmembrane domain would be expected to liberate the extracellular binding domain.

EXAMPLE 7

Expression of Growth Hormone Receptor

A full-length cDNA for the rabbit growth hormone receptor was assembled in a mammalian expression vector containing a cytomegalovirus promoter and the other functions necessary for high level expression in mammalian cells (U.S. patent application Ser .No. 06/907,185, filed Sept. 12, 1986). FIG. 11a shows the construction of this expression plasmid, pCIS2.RGHR1. First the 5' and 3' ends of the cDNA were subcloned into pUC119 from the λ cloning vectors. The 1399 bp SstI fragment of λghr.435 was cloned into the SstI site of pUC119 to generate pghr 435.1, and the 2659 bp XhoI fragment λghr.321 was cloned into the compatible SalI site of pUC119 to generate pghr.321.2. The SstI and XhoI site in the λ clones were in the cloning linkers. The final expression plasmid was constructed with the ligation of four fragments: 1) the 5340 bp ClaI, HpaI fragment of pCIS2.8c24D (U.S. patent application Ser. No. 06/907,185, supra) contains the vector; 2) a short ClaI/AvaII synthetic linker shown in FIG. 11a; 3) the 462 bp AvaII, PflMI fragment of pghr.435.1 containing the 5' end of the cDNA; and 4) the 1673 bp PflMI, DraI fragment of pghr.321.2 containing the 3' end of the cDNA. The final vector, pCIS2 RGHR1 is shown in FIG. 11b.

Figure 12A:
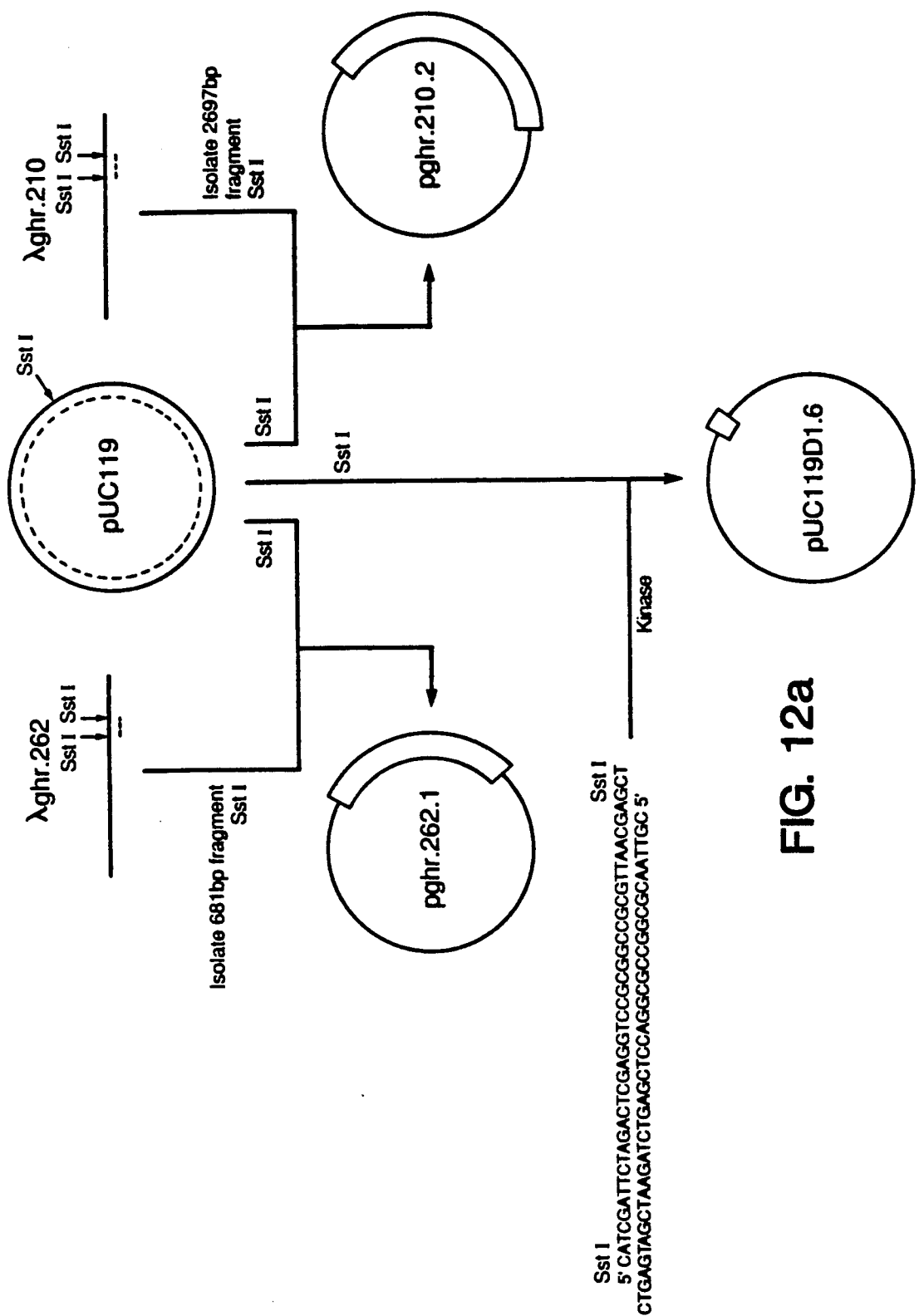
Figure 12B:
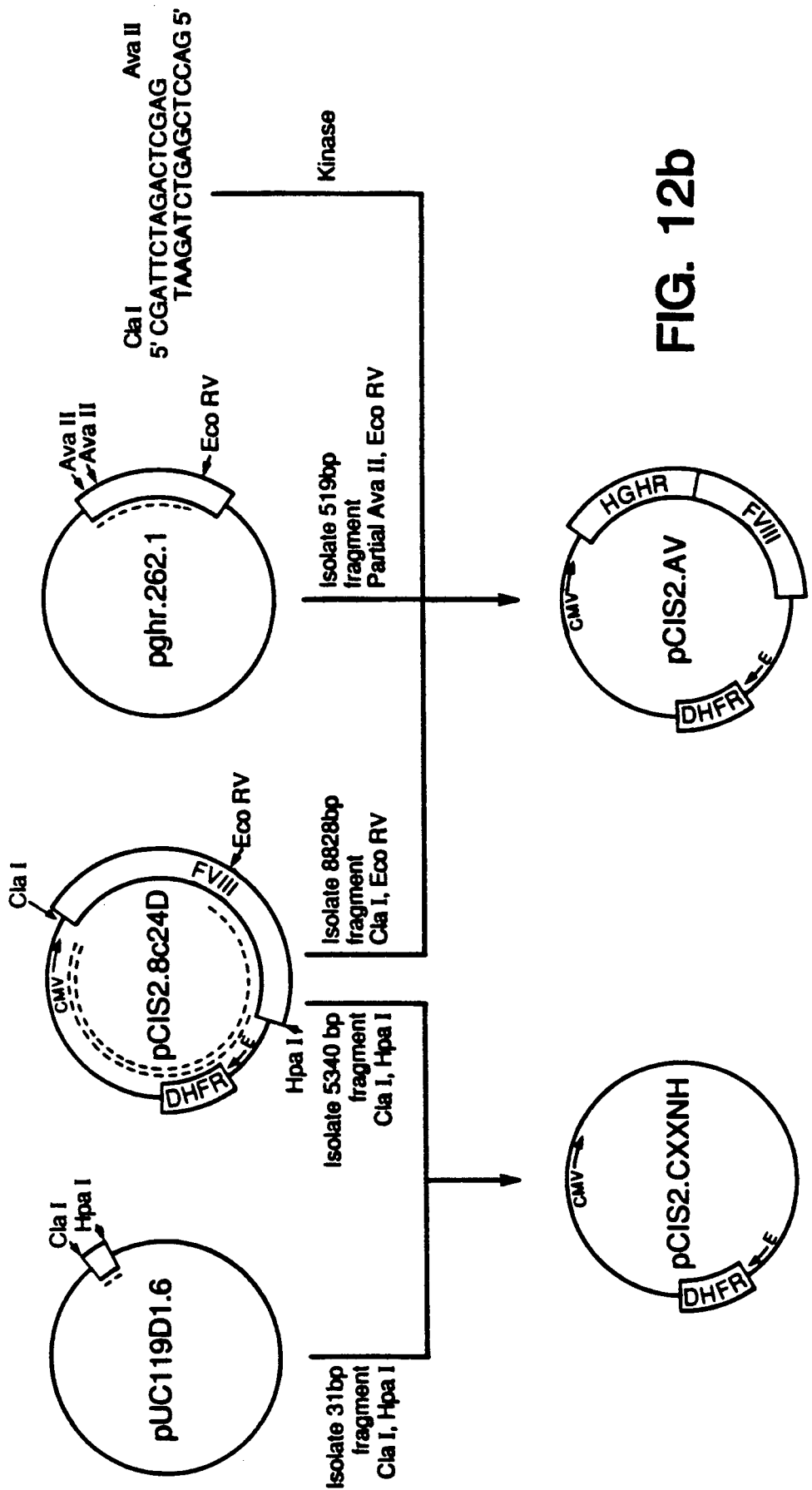
Figure 12C:
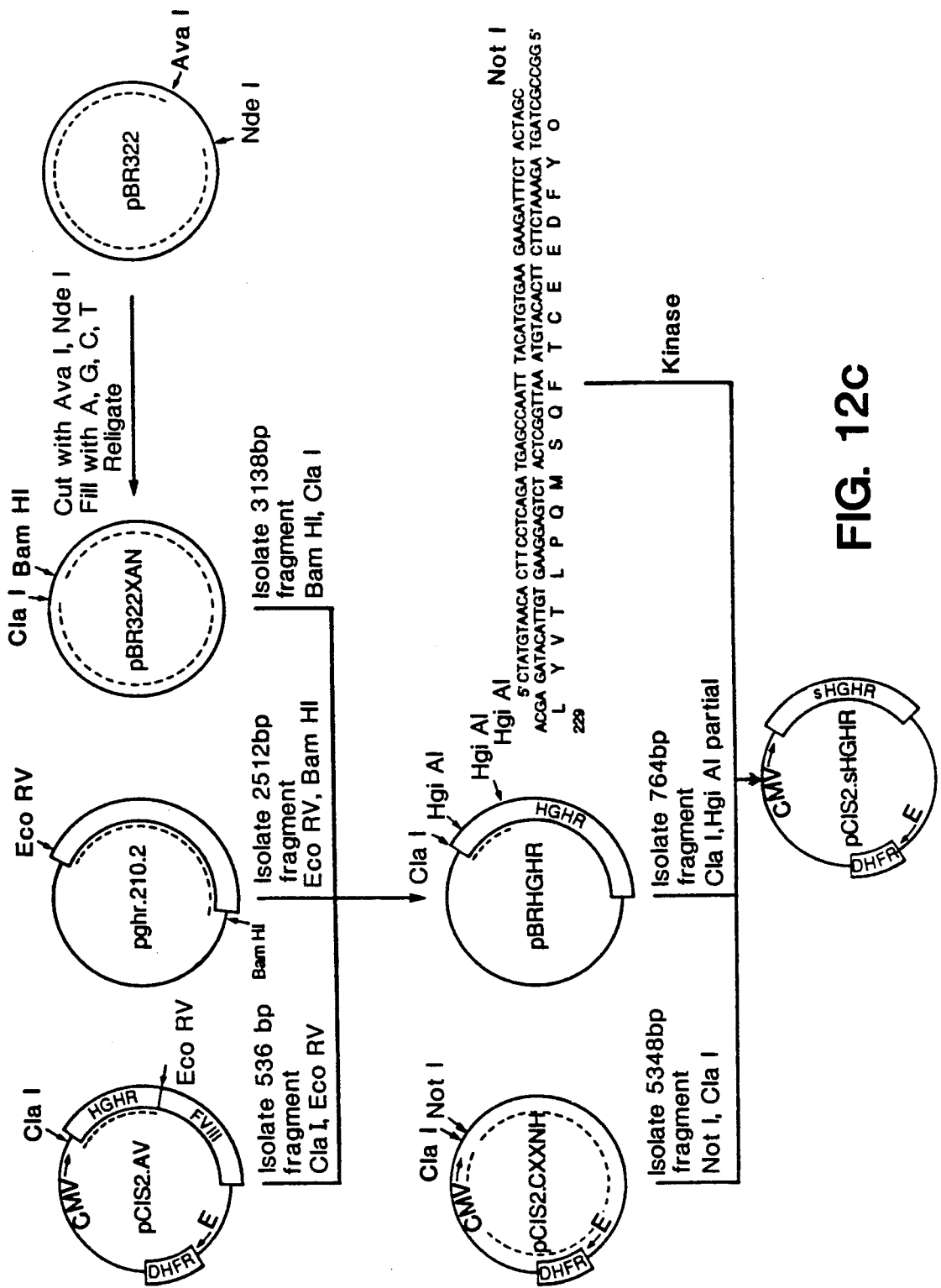

The construction of an expression vector for soluble form of the human receptor is shown in FIG. 12a-c. This vector is designed to secrete from mammalian cells the extracellular growth hormone binding domain of the receptor. This protein is functionally equivalent to the growth hormone binding protein we have purified above from rabbit serum.

First (FIG. 12a), the front and back of the human receptor λ cDNA clones were subcloned in pUC119 using the SstI sites in the cloning linkers. The 681 bp SstI fragment of λght.262 generates pghr.262.1, and the 2697 bp SstI fragment of λght.210 generates pghr.210.2. In addition a synthetic oligonucleotide with SstI ends was cloned in pUC119 at the SstI site to generate pUC119D1.6.

Second (FIG. 12b), the 31 bp ClaI, HpaI fragment of pUC119D1.6 (from the synthetic oligonucleotide) was ligated to the 5340 bp ClaI, HpaI fragment of pCIS2.8c24D (U.S. Ser. No. 06/907,185, supra) to generate the general vector, pCIS2.CXXNH. In addition three fragments were ligated to generate the 5' end of the gene: 1) 8828 bp ClaI, EcoRV fragment of pCIS2.8c24D containing the vector; 2) the 519 bp partial AvaII, EcoRV fragment of pghr 262.1 containing the 5' end of the gene; and 3) a ClaI, AvaII synthetic oligonucleotide shown in FIG. 12b. This 3 part ligation generates the plasmid pCIS2.AV.

Third (FIG. 12c), a shortened version of pBR322 was constructed by cutting with AvaI and NdeI, filling with all four nucleotides and religating. The resulting vector, pBR322XAN, was used in the ligation of three fragments: 1) 3188 bp BamHI, ClaI fragment of pBR322XAN; 2) 2512 bp EcoRV, BamHI fragment of pghr.210.2 containing the 3' end of the cDNA; and 3) 536 bp ClaI, EcoRV fragment of pCIS2.AV containing the 5' end of the gene. This three part ligation gives the plasmid pBRHGHR. The final soluble form expression plasmid was constructed by the ligation of three fragments: 1) 5348 bp NotI, ClaI fragment of pCIS2.LXXNH containing the expression vector; 2) 746 bp ClaI, partial HgiAI fragment of pBRHGHR containing the requisite portion of the cDNA; and 3) an HgiAI, NotI synthetic oligonucleotide that puts a stop codon immediately following the extracellular, growth hormone binding domain of the receptor cDNA. This three part ligation generates the expression plasmid pCIS2.sHGHR.

Figure 13A:
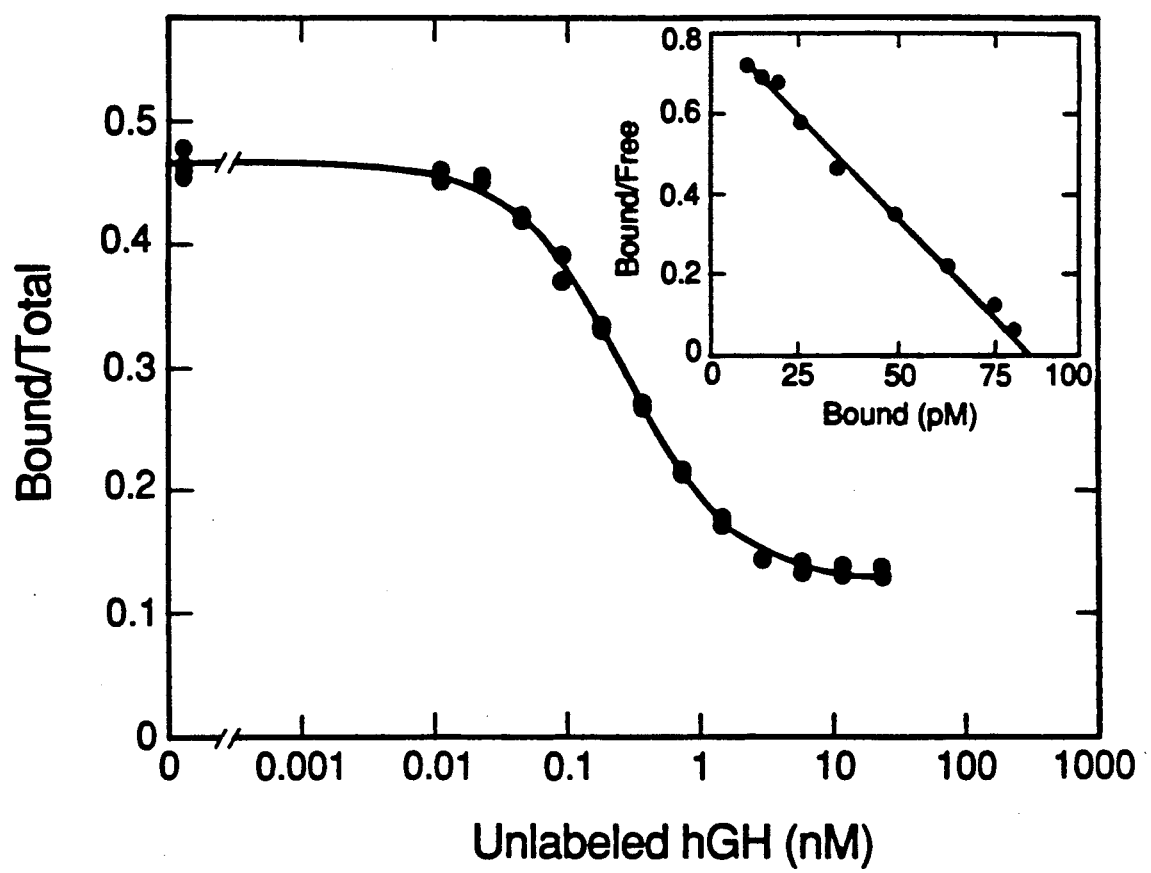

Transient transfection of the plasmid pCIS2.RGHR1 in COS-7 monkey kidney cells resulted in the expression of the receptor in cell membranes (FIG. 13a). Binding experiments with $^{125}$I-labelled growth hormone show that the expressed receptor has an affinity of $10 \times 10^9 M^{-1}$ comparable with that of the purified rabbit receptor ($28 \times 10^9 M^{-1}$). About 200,000 copies of the receptor are expressed per cell. Small amounts of high affinity growth hormone binding activity are also found in the culture medium from these cells. This soluble binding activity appears to represent the same proteolytically cleaved extracellular domain of the receptor found in rabbit serum.

Figure 13B:
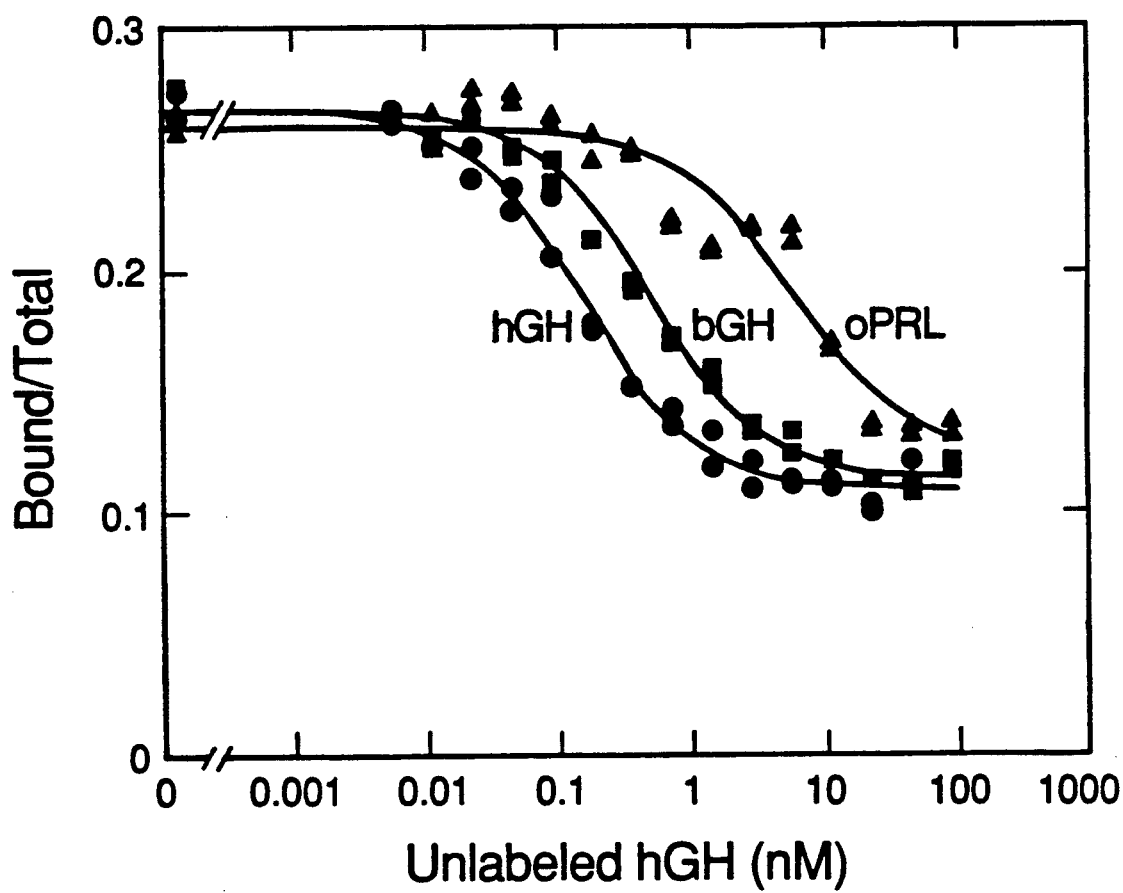

FIG. 13b shows the displacement of $^{125}$I-hGH from the expressed rabbit receptor with bovine growth hormone and ovine prolactin. As expected for the rabbit somatogenic receptor, all three cold hormones displaced $^{125}$I-hGH completely; however, for 50% displacement about 3-5 fold higher concentrations of bovine growth hormone and about 100 fold higher concentrations of ovine prolactin are required.

A similar transient transfection but in 293 cells was performed with the plasmid pCIS2.sHGHR, to secrete the soluble form of the human receptor. FIG. 14a shows the assay of specific growth hormone binding activity in the supernatents of these transfected cells. As expected, the binding activity is secreted in a soluble form with this expression vector. The binding constant is $2.2 \times 10^9 M^{-1}$ only slightly lower than that for the natural rabbit growth hormone binding proteins ($Ka = 6 \times 10^9 M^{-1}$). FIG. 14b shows the displacement of $^{125}$I-hGH from this expressed material with bovine growth hormone and ovine prolactin. As expected, for the human receptor (Lesniak J. Biol. Chem., 249:1661-1667 [1974]) the two hormones do not displace the $^{125}$I-hGH even at high concentrations.

EXAMPLE 8

Serum Binding Protein used for Growth Hormone Deficiency

Serum binding protein may be used to increase the in vivo stability and efficacy of growth hormone (GH). Therapeutic administration of growth hormone and binding protein would increase effects for a given dose schedule and extend the period between required injections.

It has been shown (Bauman, G, et al., J. Clin. Endocrinol. Metab. 64: 657-660 [1987]) that injection of human GH (hGH) complexed with partially purified human serum binding protein has a significantly longer half-life in vivo than hGH injected by itself, and that the degradation rate is lower. It has also been found that hGH complexed to certain antibodies has a much greater potency in vivo than free hGH.

Neither of these complexes would be suitable as a pharmaceutical due to the possibility of adverse reactions to the impurities in the binding protein preparation or to the antibodies used to make the complex. The essentially pure growth hormone binding protein of this invention administered in a composition with growth hormone will not be immunogenic and will show the same benefits as the preparations described earlier without possible adverse reactions due to the introduction of foreign proteins.

The dose of the serum binding protein to be given in conjunction with hGH would be in the range of 1-10 molar equivalents of the hGH being given. It can be anticipated that the dose of hGH required for efficacy in this combination therapy can be reduced by perhaps ½ to 1/5 the currently used range, and that the number of doses per week could also be reduced.

EXAMPLE 9

Serum Binding Protein as Diagnostic

The serum binding protein may be used in developing a diagnostic for children with normal levels of GH but subnormal growth rates. One such group, Laron dwarfs, has recently been shown to lack a functional serum binding protein (Bauman, G. et al., Clinical Research 35:582A [1987]; and Daughaday, W. H. et al. Clinical Research 35:646A [1987]). Since we have shown the growth hormone binding protein to be part of the liver receptor involved in stimulating growth, these children are unlikely to respond to standard growth hormone therapy. Such a defect can be diagnosed using the binding protein to assess the status of the patient's liver receptors. At some point it may also be possible to treat patients with absent and defective receptors, and so it would be desirable to have screening assays to determine the nature of the defect, since this could alter the therapy employed. While the GH binding assay is useful to some extent, it cannot distinguish between an absence of binding protein or the production of a defective binding protein incapable of binding GH. Also normal binding alone may not be sufficient, since other parts of the receptor may be defective.

Therefore, a multi-step screening process would be used. Antibodies to the binding protein would be obtained. Animals are immunized against the binding protein or to selected fragments thereof in conjugate form with such proteins as keyhole limpet hemoganin (KLH), bovine serum albumin (BSA), soybean trypsin inhibitor (STI) or bovine thyroglobulin (BT) by combining 1 mg or 1 µg of binding protein or conjugate (for rabbit or mice, respectively) with 3 volumes of Freund's complete adjuvant and injecting the solution intradermally at multiple sites. Booster shots of 1/5 to 1/10 the original amount of conjugate in Freund's complete adjuvant by subcutaneous injection at multiple sites are given one month after the initial immunization. Animals are bled one to two weeks following the booster and the serum assayed for anti-growth hormone receptor. Animals are boosted until the titer plateaus. Monoclonal antibodies are prepared by recovering spleen cells from immunized animals and immortalizing the cells in conventional fashion, e.g. by fusion with myeloma cells or by EB virus transformation and screening for clones expressing the desired antibody. Such an antibody could be incorporated into a standard immunoassay (ELISA, RIA, etc ) to determine the level of binding protein in the serum. In its simplest form, this assay would indicate if normal amounts of liver receptors are present, but it could be further refined by judicious selection of monoclonal antibodies to distinguish normal from defective types of binding protein. If the binding protein proved normal, then a further screen comparing the correct gene sequence to the patient's DNA using standard restriction mapping techniques could be used to identify defects in other portions of the receptor.

EXAMPLE 10

DNA as Diagnostic

The cDNA for the human growth hormone receptor can be used to screen patients for genetic defects in the gene itself. One possibly receptor defective population, Laron dwarfs, has been described. This screening can be accomplished in at least two ways. First, restriction fragment length polymorphism (RFLP) in the gene can be identified. These can then be used to follow a defective gene in affected families. Methods for performing this kind of gene analysis and RFLP's have been described for other genes (Gitschier et al., Nature 312:326-330 [1984] and Gitschier et al., Nature 314:738-740 [1985]). Second, the precise nature of certain defects in the growth hormone receptor gene can be identified by cloning of the receptor DNA from an affected individual and DNA sequencing. Once identified, these specific gene defects can be easily identified by genome blot hybridization under low stringency conditions on affected individual's (as for example in his child's) DNA by direct oligonucleotide hybridization. Methods for these techniques have been described in detail (Gitschier et al., Nature 315:427-430 [1985]; Gitschier et al., Science 232:1415-1416 [1986]).

EXAMPLE 11

Growth Hormone Receptor and Binding Protein Assay of Growth Hormone

Both the serum binding protein and the intact receptor can be used to assay GH. Current assays are of two types. To measure GH levels, an antibody assay is generally employed. This is simple but suffers from the disadvantages that an antibody may not recognize GH complexed to other proteins and cannot distinguish active from inactive GH. The latter requires a bioassay involving removing the pituitary from rats, injecting them with the GH preparation and measuring weight gain and tissue growth. While this gives an indication of activity of the GH, it is slow, cumbersome and requires large amounts of the GH preparation. Also efficacy in rats may not always be a good indicator of efficacy in hormones of other species.

Therefore we propose to develop two types of GH assays using purified recombinant serum binding protein for one and the membrane-bound reconstituted into mammalian cells for the second.

The assay using the serum binding protein would indicate whether GH is present which is capable of binding to the GH receptor. This could be implemented in several ways. For instance, the serum binding protein could be coupled to a 96 well microtiter plate and deletions of the samples containing GH incubated with the bound receptor in the presence of a fixed amount of authentic GH with biotin coupled to it. After a 4-6 hr incubation, the solutions would be removed and the plates washed to remove unbound GH. Adding avidin coupled to horse radish peroxidase (HRP) and incubating would form a complex with the GH-biotin. Again the plate would be washed and HRP substrate added. Color would develop most in wells containing samples with no GH. As the sample continued incubating amounts of GH, the biotin-GH would bind at decreasing levels, hence the color development would be less.

This would give a dose-dependent response which could be calibrated using authentic GH of known concentrations. This type of assay would have the advantages of a radioreceptor assay, specificity for active ligand capable of binding to the receptor, sensitivity and the simplicity of an ELISA antibody assay without the disadvantages of either (i.e. radioactive tracer, not specific for active protein).

An assay for GH bioactivity could also be developed using the intact (membrane-bound) receptor. In this case, the full length receptor would be incorporated into a mammalian cell line capable of producing a significant biological response (e.g., release of IGF-1) upon stimulation of the GH receptor. These cells would then be incubated with the GH preparation and the amount of IGF-1 released could be measured by ELISA. This would be an assay for bioactive GH (as opposed to denatured or inhibitory) which would be much faster than the hypophysectomized assay (2-3 days vs. 2-3 weeks) and which would allow measurement of activity on the receptor from the specie of interest.

We claim:

1. A DNA isolate encoding human or rabbit growth hormone receptor.

2. A DNA isolate encoding human or rabbit growth hormone binding protein.

3. Purified nucleic acid encoding functional growth hormone receptor or growth hormone binding protein which is capable of hybridizing with nucleic acid encoding human or rabbit growth hormone receptor under low stringency conditions comprising incubating or washing with about 0.15M sodium chloride and 0.015M sodium citrate at about 32°–50° C., or its equivalent.

4. The nucleic acid of claim 3 wherein said low stringency conditions further comprise incubating with about 20% formamide, 0.75M sodium chloride/0.075M sodium citrate, 50 mM sodium phosphate (pH 7) at 42° C., followed by incubating or washing with about 0.15M sodium chloride/0.015M sodium citrate at 42° C.

5. The isolate of claim 1 wherein the isolate is free of human or rabbit growth hormone receptor introns.

6. The isolate of claim 2 wherein the isolate is free of human or rabbit growth hormone binding protein introns.

7. A recombinant expression vector comprising the DNA of claim 1.

8. A recombinant expression vector comprising the DNA of claim 2.

9. A composition comprising a cell transformed with the recombinant expression vector of claim 7.

10. A composition comprising a cell transformed with the recombinant expression vector of claim 8.

11. The composition of claim 9 wherein the cell is a mammalian cell.

12. The composition of claim 9 wherein said cell is *E. coli*.

13. The composition of claim 10 wherein the cell is a mammalian cell.

14. A process for producing human and rabbit growth hormone receptor comprising constructing a vector which includes DNA encoding human or rabbit growth hormone receptor, transforming a host cell with said vector, culturing said transformed cell and recovering said receptor from the culture.

15. A process for producing human and rabbit growth hormone binding protein comprising constructing a vector which includes DNA encoding human or rabbit growth hormone binding protein, transforming a host cell with said vector, culturing said transformed cell and recovering said binding protein from the culture.

16. The process of claim 14 wherein the host cell is a eukaryotic cell.

17. The process of claim 15 wherein the host cell is a eukaryotic cell.

18. The process of claim 16 wherein the eukaryotic cell is a human embryonic kidney cell line.

19. The process of claim 17 wherein the eukaryotic cell is a human embryonic kidney cell line.

20. The process of claim 16 wherein the eukaryotic cell is a chinese hamster ovary cell line.

21. The process of claim 17 wherein the eukaryotic cell is a chinese hamster ovary cell line.

* * * * *